United States Patent
Inoue

(10) Patent No.: US 6,270,520 B1
(45) Date of Patent: *Aug. 7, 2001

(54) APPLIANCE TO BE IMPLANTED, METHOD OF COLLAPSING THE APPLIANCE TO BE IMPLANTED AND METHOD OF USING THE APPLIANCE TO BE IMPLANTED

(76) Inventor: Kanji Inoue, 98-13 Miyazaki-cho Simogamo, Sakyo-ku, Kyoto-shi, Kyoto 606-0802 (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/310,980

(22) Filed: May 13, 1999

Related U.S. Application Data

(62) Continuation-in-part of application No. 08/898,427, filed on Jul. 22, 1997, now Pat. No. 5,925,076, which is a division of application No. 08/765,216, filed as application No. PCT/JP96/01347 on May 17, 1996, now Pat. No. 5,843,162.

(30) Foreign Application Priority Data

May 19, 1995 (JP) .......................... PCT/JP95/00972

(51) Int. Cl.$^7$ ...................................... A61F 2/06
(52) U.S. Cl. .......................... 623/1.11; 623/1.15
(58) Field of Search ............. 623/1.15, 1.32–1.33, 623/1.28, 1.11, 1.12

(56) References Cited

U.S. PATENT DOCUMENTS

| | | |
|---|---|---|
| 3,304,557 | 2/1967 | Polansky . |
| 4,313,231 | 2/1982 | Koyamada . |
| 4,872,874 | 10/1989 | Taheri . |
| 5,098,406 | 3/1992 | Sawyer . |
| 5,104,399 | 4/1992 | Lazarus . |
| 5,151,105 | 9/1992 | Kwan-Gett . |
| 5,183,085 | 2/1993 | Timmermans . |
| 5,207,695 | 5/1993 | Trout, III . |
| 5,234,456 | 8/1993 | Silvestrini . |
| 5,236,447 | 8/1993 | Kubo et al. . |
| 5,242,452 | 9/1993 | Inoue . |

(List continued on next page.)

FOREIGN PATENT DOCUMENTS

| | | |
|---|---|---|
| 4219949 | 12/1993 | (DE) . |
| 0472731 | 3/1992 | (EP) . |
| 2164562 | 3/1986 | (GB) . |
| 3-236836 | 10/1991 | (JP) . |
| 4-25755 | 2/1992 | (JP) . |
| 4-263852 | 9/1992 | (JP) . |
| 5-212121 | 8/1993 | (JP) . |
| 7-24072 | 1/1995 | (JP) . |
| 3009638 | 2/1995 | (JP) . |
| 6-63155 | 3/1995 | (JP) . |
| 91/12047 | 8/1991 | (WO) . |
| WO 91/12047 | 8/1991 | (WO) . |
| 95/05788 | 2/1995 | (WO) . |

*Primary Examiner*—Cary E. O'Connor
(74) *Attorney, Agent, or Firm*—Banner & Witcoff, Ltd.

(57) ABSTRACT

The artificial blood vessel A comprises a front end wire ring $10_1$, a rear end wire ring $10_2$ arranged facing to the front end wire ring $10_1$, a tubular cover 7 which connects the end wire rings $10_1$, $10_2$, and a plurality of intermediate wire rings 12 arranged spaced apart from each other between the front end wire ring $10_1$ and the rear end wire ring $10_2$. Each of the front end wire ring $10_1$, the rear end wire ring $10_2$ and the intermediate wire rings 12 are given flexibly foldable elasticity. The circumference of the front end wire ring $10_1$ is equally divided into four by dividing points $41_1$, $42_1$, $43_1$, $44_1$. Hooking means 13 are formed for a front pull string to be passed through at the dividing points $41_1$, $43_1$. The circumference of the intermediate wire ring 12 is fixed to the tubular cover 7 by suturing or with adhesive at the positions $51_3$, $52_3$, $53_3$, $54_3$ which correspond to the midpoint $51_1$ between the dividing points $41_1$, $42_1$, the midpoint $52_1$ between the dividing points $42_1$, $43_1$, the midpoint $53_1$ between the dividing points $43_1$, $44_1$, and the midpoint $54_1$ between the dividing points $44_1$, $41_1$.

18 Claims, 52 Drawing Sheets

U.S. PATENT DOCUMENTS

| | | |
|---|---|---|
| 5,290,305 | 3/1994 | Inoue . |
| 5,330,528 | 7/1994 | Lazim . |
| 5,383,926 | 1/1995 | Lock et al. . |
| 5,387,235 | 2/1995 | Chuter . |
| 5,507,767 | 4/1996 | Maeda et al. . |
| 5,507,771 | 4/1996 | Gianturco . |
| 5,554,181 | 9/1996 | Das . |
| 5,554,183 * | 9/1996 | Nazari ................................ 623/1 |
| 5,562,726 * | 10/1996 | Chuter ................................ 623/1 |
| 5,607,445 | 3/1997 | Summers . |
| 5,609,628 | 3/1997 | Keranen . |
| 5,628,783 | 5/1997 | Quiachon et al. . |
| 5,665,117 | 9/1997 | Rhodes . |
| 5,676,671 | 10/1997 | Inoue . |
| 5,693,089 | 12/1997 | Inoue . |
| 5,755,772 | 5/1998 | Evans et al. . |
| 5,755,773 | 5/1998 | Evans et al. . |
| 5,782,904 | 7/1998 | White et al. . |
| 5,824,037 | 10/1998 | Fogarty et al. . |
| 5,843,158 * | 12/1998 | Lenker et al. ...................... 623/1 |
| 5,843,162 | 12/1998 | Inoue . |
| 5,925,076 * | 7/1999 | Inoue ................................ 623/1 |
| 5,976,179 * | 11/1999 | Inoue ................................ 623/1 |

\* cited by examiner

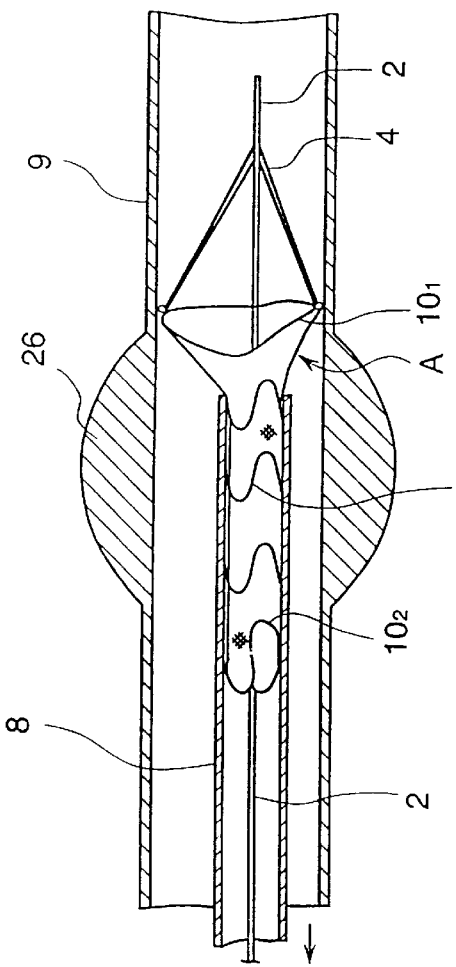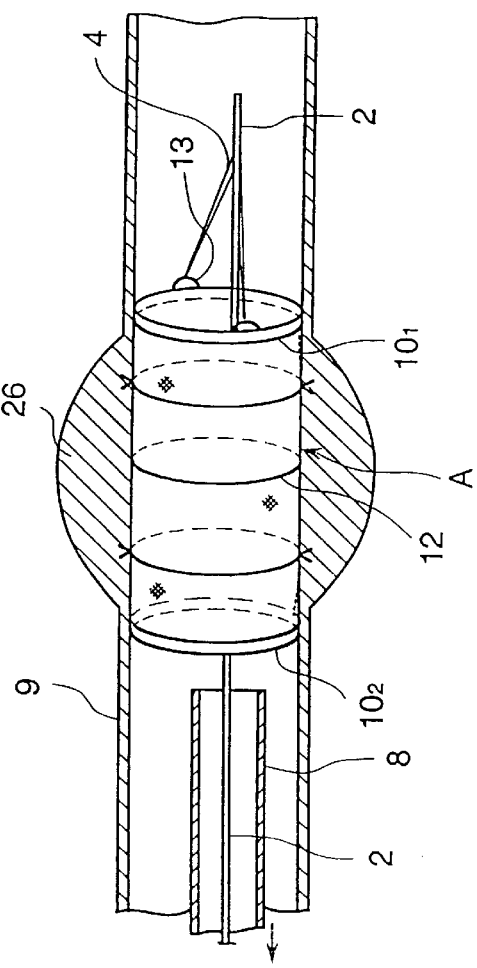

APPLIANCE TO BE IMPLANTED, METHOD OF COLLAPSING THE APPLIANCE TO BE IMPLANTED AND METHOD OF USING THE APPLIANCE TO BE IMPLANTED

This application is a continuation-in-part of application Ser. No. 08/898,427, filed Jul. 22, 1997, now U.S. Pat. No. 5,925,076, which is a divisional of application Ser. No. 08/765,216, filed Jan. 3, 1997, now U.S. Pat. No. 5,843,162, which is a national phase application of PCT/JP96/01347, filed May 17, 1996.

FIELD OF THE ART

This invention relates to appliances for medical treatment and, more particularly, to an appliance collapsible for insertion into a human organ and capable of resilient restoration (which will be referred to as "the appliance to be implanted" in this specification and claims), to a method of collapsing the appliance to be implanted, and to a method of using the collapsed appliance to be implanted into a catheter.

BACKGROUND ART

The artificial blood vessel is an example of the appliance to be implanted. At present, treatment of, for example, aortic aneurysm is conducted by implanting an artificial blood vessel. In particular, the portion of a blood vessel which has an aneurysm is removed by resection, and an artificial blood vessel is implanted in place of the resected portion and connected to the remaining blood vessel by suturing or the like.

The above-mentioned method of surgically implanting the artificial blood vessel for treatment of aortic aneurysm, however, is highly dangerous. Especially, an emergency operation for treatment of a ruptured aneurysm has a low life-saving rate, and an operation of dissecting aortic aneurysm is difficult to conduct and has a high death rate.

Therefore, in order to treat these diseases without a surgical operation, a method has been developed of introducing a catheter into an appliance such as an artificial blood vessel in collapsed condition into a human organ such as a blood vessel, and transporting the appliance to a desired position such as an affected or constricted portion thereof, where the appliance is released so as to be expanded and implanted there.

The appliance to be implanted is so constructed that a pair of end wire rings which are flexibly foldable and elastic are arranged to divide themselves, each of the end wire rings is connected by a tubular cover which is made of a sheet of flexible and tensile material and an intermediate wire ring is arranged between both of the end wire rings and fixedly connected to the above-mentioned tubular cover by suturing or with adhesive.

As a method of collapsing the appliance to be implanted, the following method is adopted in which a plurality of hooking means for a pull string to be passed are formed at every other dividing points each of which equally divides the circumference of the front end wire ring into an even number, the front end wire ring is folded into a wavy shape with the dividing points which are provided with a hooking means for a pull string forming forwardly directed peaks and the dividing points which are not provided with a hooking means for a pull string forming the bottoms of forwardly directed valleys, each of the intermediate wire rings and the rear end wire ring is folded into a wavy shape having the same phase as that of the front end wire ring and the whole artificial blood vessel is inserted into a catheter.

The above-mentioned intermediate wire ring is inevitable because of several points of view, such as it provides the artificial blood vessel with a capability of keeping its tubular shape so as to fit a human body when arranged at a bent position in a body, thereby to prevent the artificial blood vessel from being pushed downstream. However, if such an intermediate wire ring is attached to the tubular cover, the appliance is easily prevented from being folded. The reason is that the tubular cover tries to follow the movement of the front end wire ring with forming big wrinkles near the front end wire ring when the front end wire ring is folded into a wavy shape since the tubular cover is connected to the front and rear end wire rings at both end portions thereof. However, as the tubular cover is made of a sheet, the locally formed wrinkles do not bring about transformations at the center of the tubular cover. Therefore, for example, if the whole area of the circumference of the intermediate wire ring is fixedly connected to the tubular cover, the center of the tubular cover is dragged at the specified positions of the circumference thereof toward the direction of the peak or the valley along the wavy shape of the intermediate wire ring and the whole tubular cover tends to be bulky as well as unfavorable load is applied to the intermediate wire ring because of the sliding resistance. Therefore, the intermediate wire ring may be hindered from being folded into a small size with forming a regular wavy form because of distortion of the direction the intermediate wire ring is to be folded as well as of folding force. Even though the intermediate wire ring is fixedly connected to the tubular cover only at several points of the circumference thereof each of which is spaced apart, the points selected at random will cause sliding resistance from the tubular cover toward the peaks or valleys, thereby to provide no effective means to solve the problems.

In addition, the mutual interference between the intermediate wire ring and the tubular cover not only prevents the intermediate wire ring from being folded but also folds the appliance to be implanted imperfectly and insufficiently. Bent portion caused by the appliance to be implanted unnatuarally folded will cut off the permanent function as a blood vessel. This also may hinder the movement of transporting the artificial blood vessel through a catheter and the function of the appliance to be implanted as it is intended to because of imperfect restoration of the appliance to be implanted even though the appliance to be implanted is released at a target portion.

On the other hand, the blood vessel is distributed variously in a body and, for example, an artery which comes from a heart is bifurcated at the groin of a thigh. If an affected part falls on the bifurcated part, the above mentioned cylindrical-shaped artificial blood vessel can not be used as it is, so that it is inevitable that an artificial blood vessel whose shape fits for such a shape of blood vessel should be developed. In addition, for implanting an artificial blood vessel in such a bifurcated part it is not enough just to transport the artificial blood vessel to a target position through a catheter and release it there. In this case, it is necessary to move the artificial blood vessel to be fit for a shape of the blood vessel at an target position after released, thereby requiring to develop a method of moving the artificial blood vessel.

The object of the invention is to solve all of the above-mentioned problems.

DISCLOSURE OF THE INVENTION

The appliance to be implanted in accordance with the invention is characterized by that comprising a front end wire ring, a rear end wire ring arranged facing to the front end wire ring, a tubular cover which connects the front end wire ring and the rear end wire ring, and a plurality of intermediate wire rings spaced apart from each other between the front end wire ring and the rear end wire ring, that each of the front end wire ring and the rear end wire ring and the intermediate wire rings are given flexibly foldable elasticity, that the circumference of the front end wire ring is equally divided into four or an even number over four, hooking means are formed for a front pull string to be passed through at every other dividing point and that the circumference of the intermediate wire ring is fixed to the tubular cover by suturing or with adhesive at the positions which correspond to the midpoints between each adjacent two of the dividing points of the front end wire ring.

The appliance to be implanted may concretely be represented by that a single rear end wire ring is arranged to face to a single front end wire ring, or that parallely arranged two rear end wire rings are arranged to face to a single front end wire ring and a bifurcated tubular cover connects the front end wire ring and two rear end wire rings with forming a Y-shape.

To improve the implanting state of the appliance to be implanted, it is effective that each of the front and rear end wire rings is circumferentially covered with an elastic protective material, thorns are provided on the circumference of at least one of the wire rings so as to stick into a human organ to be embedded therein, or a pole is provided to connect at least two adjacent wire rings.

The method of collapsing the appliance to be implanted in accordance with the invention is characterized by that the appliance to be implanted comprises a front end wire ring, a rear end wire ring arranged facing to the front end wire ring, a tubular cover which connects the front end wire ring and the rear end wire ring, and a plurality of intermediate wire rings spaced apart from each other between the front end wire ring and the rear end wire ring, that each of the front and rear end wire rings and the intermediate wire rings are given flexibly foldable elasticity, that the circumference of the front end wire ring is equally divided into four or an even number over four, hooking means are formed for a front pull string to be passed through at every other dividing point and that the circumference of the intermediate wire ring is fixed to the tubular cover by suturing or with adhesive at the positions which correspond to the midpoints between each adjacent two of the dividing points of the front end wire ring, and that the method comprises the steps of; folding the front end wire ring into a wavy shape with the dividing points each of which is provided with a hooking means forming forwardly directed peaks and the other dividing points forming the bottoms of forwardly directed valleys, and folding the intermediate wire rings and the rear end wire ring each into a way shape having the same phase that of the front end wire ring, thereby to insert the whole appliance to be implanted into a catheter.

If the number of the dividing points are four, it is effective to pick the whole appliance to be implanted by forceps along a generatrix which passes two points facing each other on the front end wire ring and each of which is provided with a hooking means and then to insert the appliance to be implanted together with the forceps into the funneled tube from a big portion of the funneled tube toward a small portion thereof, and finally to pull the forceps out of the funneled tube.

The forceps may preferably be provided with serrate engaging member which lessens a sliding resistance between the appliance to be implanted and the forceps toward the direction to be pulled than that to be inserted.

For inserting an appliance to be implanted which has been kept in a collapsed condition into a catheter, it is effective that a pair of strings each of which has a loop at the tip thereof are provided for each of the wire rings respectively, that the strings are engaged with either one of the wire ring or the tubular cover at the positions of the circumference of each wire rings which correspond to the midponts between two adjacent dividing points of the front end wire ring, and one of the strings is wound around the wire ring clockwise until it reaches the backward of the wire ring while the other string is wound around the wire ring counterclockwise until it reaches the backward of the wire ring, that a retaining rod is passed through the part at which each of the loops overlaps, and that each of the strings is tied each other so as to keep each of the wire rings in a collapsed condition. The retaining rod may preferably comprise a tube and a wire which is inserted into and passed through the tube. It is especially advantageous that after the wire rings are kept in a collapsed condition, the tube is pulled out so as to keep the collapsed condition by the wire alone.

For collapsing each wire rings into a wavy shape by inserting the appliance to be implanted into a funneled tube from a big portion of the funneled tube toward a small portion thereof, it is effective the appliance has previously been contained in a pipe member having a diameter which is bigger than that of the small portion of the funneled tube and smaller than that of the big portion of the funneled tube.

The method of using the appliance to be implanted in accordance with the invention is characterized by that the appliance to be implanted comprises a single front end wire ring, parallely arranged two rear end wire rings facing to the front end wire ring, and a Y-shaped tubular cover connecting the front end wire ring and the rear end wire rings, in order to implant the appliance to be implanted into a Y-shaped portion having two branches bifurcated from a single trunk a front hooking means is formed at the front end wire ring for pulling whole of the appliance to be implanted forward and a rear hooking means is formed at each of the rear end wire rings for pulling the appliance to be implanted rearward respectively, and that the method comprises the steps of; pulling the front hooking means of the front end wire ring toward the target portion to be implanted so as to transport the appliance to be implanted through one of the branches to the trunk, and then pulling each of two rear hooking means of the rear end wire rings so as to drag each of the rear end wire rings to one of the branches and to the other branch respectively.

For inserting one of the rear hooking means of the appliance to be implanted into one of the branches of a Y-shaped portion to be implanted and dragging it into other branch thereof, it is effective that a device for transporting an appliance to be implanted is attached to the rear hooking means of the appliance to be implanted so as to urge the appliance to be implanted rearward when the appliance to be implanted is transported to near the trunk though one of the branches and that the device for transporting an appliance which is attached to one of the rear hooking means of the appliance to be implanted is caught and dragged into other branch by a catcher which has been inserted into near the trunk through other branch.

For securely catching the device for transporting an appliance by a catcher, it is preferable that the device for transporting an appliance to be implanted which is to be dragged out of the body by a catcher is transported to a portion to be implanted through one of the branches with the front end of the device engaged with the rear hooking means, that the base end of the device is turned down and transported to the portion to be implanted through the same branch, and then the base end of the device is caught by the catcher.

For effectively preventing the device for transporting an appliance to be implanted from entangling in the appliance to be implanted, it is preferable to adopt a method that comprises steps of; arranging a guide pipe which has a valve at the base end thereof along one of the branches and into which the front end of the device for transporting an appliance has previously been inserted hugh a hole provided on the valve by being pushed to open the hole with making use of the elasticity of the hole, pushing the base end of the device for transporting an appliance which is turned down so as to be inserted into the guide pipe through other hole provided on the valve so as to open the hole with resisting the elasticity of the hole, and pulling the catcher which catches the base end of the device for transporting an appliance so that the two holes become continuous each other and the turned down portion of the device for transporting an appliance is contained in the guide pipe.

For making it easy to transport the appliance to be implanted it is preferable that a pair of strings each of which has a loop at the tip thereof are provided for each of the wire rings respectively, that the strings are engaged with the tubular cover at the positions of the circumference of each wire rings which correspond to the midpoints between two adjacent dividing points of the front end wire ring, and one of the strings is wound around the wire ring clockwise until it reaches the backward of the wire ring while the other string is wound around the wire ring counterclockwise until it reaches the backward of the wire ring, that a retaining rod is passed through the part at which each of the loops overlaps, and that each of the strings is tied each other so as to keep each of the wire rings in a collapsed condition.

For making use of the appliance to be implanted more generally even though the shape of the portion into which the appliance to be implanted is implanted varies it is effective to adopt a method of using the appliance to be implanted that at least two appliances to be implanted are prepared, that the front end wire ring of the appliance to be implanted which is inserted later locates in front of the rear end wire ring of the other appliances to be implanted which is inserted former, and that the appliance is connected to the adjacent appliance with each other partially overlapped at the adjacent position. In this case, it is especially preferable that the appliance to be implanted arranged downstream has a diameter which is smaller than that of the appliance to be implanted arranged upstream and the appliance to be implanted downstream is partially inserted into the appliance to be implanted upstream.

With the appliance to be implanted and the method of collapsing the appliance to be implanted in accordance with the invention, the operation of collapsing the appliance to be implanted can be conducted smoothly and the condition of which the appliance is implanted becomes satisfactory. In other words, as the intermediate wire ring is collapsed into a wavy shape having the same phase as that of the front end wire ring, to put it in an extreme way each of the points on the circumference corresponding to the dividing points forms a peak of a mountain or a bottom of a valley formed between two mountains by taking turns while the positions corresponding to midpoints between each adjacent two of the dividing points move neither frontward nor rearward at all. As the intermediate wire rings are fixedly attached to the tubular cover at several points each spaced apart, the portions of the intermediate wire ring which bent most when being folded are free of the tubular cover. This makes the intermediate wire ring free from dragging resistance from the tubular cover, they to secure the free movement to be collapsed with ease. In addition, as the intermediate wire ring is collapsed into a wavy shape as well as the front end wire ring, the whole appliance is given a big folding rate, thereby to secure a compact collapsed state and good transporting movement through a catheter for a relatively bulky appliance to be implanted. In addition, in accordance with the arrangement, if the appliance to be implanted is released at a target position in a blood vessel, the dividing points are restored toward right-angled direction to the blood vessel, and the end portion of the appliance to be unplanted certainly open and does not close the inner space thereof. This helps the appliance to be implanted to appropriately follow the movement of the constantly pulsating blood vessel with close adherence as well as improves a rate of successful implantation. The above-mentioned operation functions for not only a simple tubular shaped appliance to be implanted but also a bifurcated Y-shaped appliance to be implanted.

Elastic protective material circumferentially covering the wire rings of the appliance to be implanted is useful to prevent the inner wall of a human organ from being damaged by direct contact with the wire rings. The protective material also acts as a seal to attach both ends of the appliance to be implanted tightly to the inner wall of a human body, thereby to effectively prevent leakage of blood through the ends of the appliance when implanted.

When thorns are provided projecting from the wire rings, they stick into the inner wall of a human organ to be embedded therein so that the whole appliance is fixed to the human organ. Therefore, the thorns effectively prevent the appliance to be implanted from being displaced or even carried by blood flow downstream in a blood vessel.

It can effectively improve the tubular shape of the whole appliance to be implanted in the strength and the construction if at least two of the adjacent wire rings are connected by a rod.

If the number of the dividing points is four, it is extremely easy to fold the appliance to be implanted by using a pair of forceps. Namely, if the appliance to be implanted is inserted into the funneled tube with the whole appliance picked by forceps along a generatrix which passes two points facing each other on the front end wire ring each of which is provided with a hooking means, the points picked by the forceps are carried in advance from the big portion to the small portion of the funneled tube while other points approach each other with restrained by a tapered surface of the inner wall of the funneled tube from moving forward following the points having a hooking means. The points picked by the forceps inevitably form a peak of a mountain and the midpoints between two adjacent points picked by the forceps form a bottom of a valley, thereby to fold the appliance to be implanted into an appropriate wavy shape. In this case, the intermediate wire rings are easily transformed to the direction so as to form a mountain and a valley with the points on the circumference of the intermediate wire ring corresponding to the midpoints between two adjacent dividing points on the front end wire ring serving as fulcrum, which makes the operation of folding the appliance smooth and appropriate.

In this case, if the forceps are provided with serrate engaging member, the pushing force applied to the forceps can effectively be transformed to a force of propelling the appliance to be implanted by making use of the serrations of the engaging member when inserting the appliance to be implanted, and the forceps can be smoothly withdrawn from the funneled tube without dragging the appliance to be implanted by making use of the serrations of the engaging member.

If the points on the circumference of the intermediate wire ring corresponding to the midpoints between two adjacent dividing points are tied by a pair of strings each of which has a loop at the tip thereof and a retaining rod is passed through the part at which each of the loops overlaps, the appliance to be implanted is kept in a collapsed condition. This makes it possible that the appliance to be implanted is inserted into a catheter without using a funneled tube. This also makes it easy to adjust the position at which the appliance is implanted because the appliance to be implanted can be kept in a collapsed condition after it is released from the catheter. This method is useful especially for the appliance to be implanted whose shape is bifurcated. In addition, if the retaining rod is pulled out, the loops overlapping each other are released from binding and free to move. As the portion at which the stings are sewed to the tubular cover is loosened, the force to keep the appliance to be implanted in a collapsed condition is released, and then the appliance to be implanted is restored to the original shape without bound by strings. In this case, as the strings are used as not a single but a pair, even though one of the strings might get stuck on the way, the appliance to be implanted is guaranteed to restore by another string.

If the retaining rod comprising a tube and a wire is used and the tube is pulled out with the wire left in a collapsed condition, the whole appliance to be implanted remains flexible with the wire functioning as the retaining rod. This makes it possible that the appliance to be implanted passes smoothly through the bent portion or the like when transported in a collapsed condition.

If the appliance to be implanted has previously been contained in a pipe member having a diameter bigger than that of the small portion of the funneled tube and smaller than that of the big portion of the funneled tube, it saves the operation of collapsing the appliance to be implanted. Just inserting the pipe member into the funneled tube so as to make abutting engagement with the inner surface of the funneled tube and pulling out the appliance to be implanted from the side of the front end wire ring enables the appliance to be implanted to be collapsed into a smaller size so as to be inserted into the small portion of the funneled tube and a catheter.

With the method of using the appliance to be implanted in accordance with the invention, a Y-shaped appliance to be implanted can effectively be transported to be implanted into a portion at which a blood vessel branches out into two, thereby to greatly improve the appliance to be implanted in use generally and practically.

In this case, if a catcher is inserted into near the portion to be implanted and catches a device for transporting the appliance which is attached to one of the rear end wire rings of the appliance to be implanted, it can be extremely easy to fix the appliance to be implanted into a bifurcated portion to be implanted.

If the front end of the device for transporting the appliance is engaged with the appliance to be implanted and the base end of the device for transporting the appliance is turned down so as to be caught by the catcher, it becomes easy to arrange the device for transporting the appliance at a position where it is easy for the catcher to catch. As a result of this, the accuracy and the efficiency of implanting the appliance to be implanted is effectively improved.

During the above process if a guide pipe having a valve is used, it becomes possible to guide the base end of the device for transporting the appliance to a position preferable to be caught with not only preventing bleeding but also preventing the device for transporting the appliance from entangling in the appliance to be implanted.

If a pair of the appliances to be implanted in accordance with the invention are connected to partially overlap, it can change the length of the connected appliances relatively freely by adjusting the length of the overlapped portion. This makes it possible to commonly use the same standardized appliances to be implanted for the organ into which the appliance is to be implanted even though the length or the shape of the organ varies a little. If the appliance to be implanted arranged downstream is partially inserted into the appliance to be implanted arranged upstream, not only both of the appliances to be implanted can be connected smoothly but also the appliance can be implanted satisfactory so as to fit the shape of the blood vessel into which the appliance is to be implanted because usually blood vessels are gradually smaller in diameter from upstream to downstream.

BRIEF DESCRIPTION OF THE DRAWINGS

FIG. 31 shows a step to release the artificial blood vessel at the affected part in the blood vessel.

FIG. 32 is a cross-sectional view showing the artificial blood vessel released at the affected portion in the blood vessel.

BEST MODES OF EMBODYING THE INVENTION

The invention will be described in detail with reference to the embodiments thereof shown in the accompanying drawings.

Figure 1:
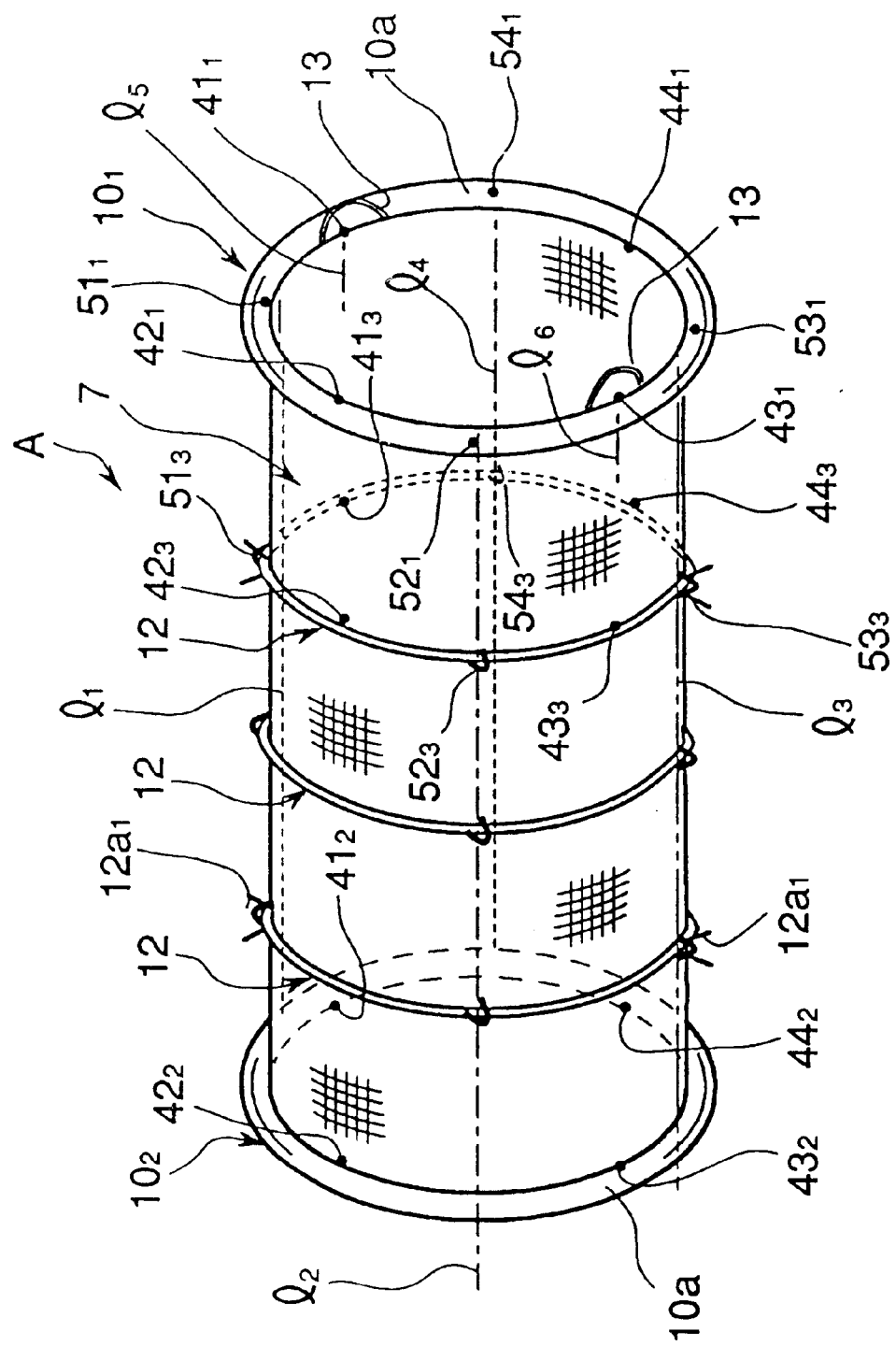
FIG. 1 is a perspective view of an artificial blood vessel used in one embodiment of the invention.

The artificial blood vessel A as the appliance to be implanted, which is collapsed by the method in accordance with this invention, comprises, as shown in FIG. 1, a cover 7, end wire rings $10_1$, $10_2$ and intermediate wire rings 12.

Figure 2:
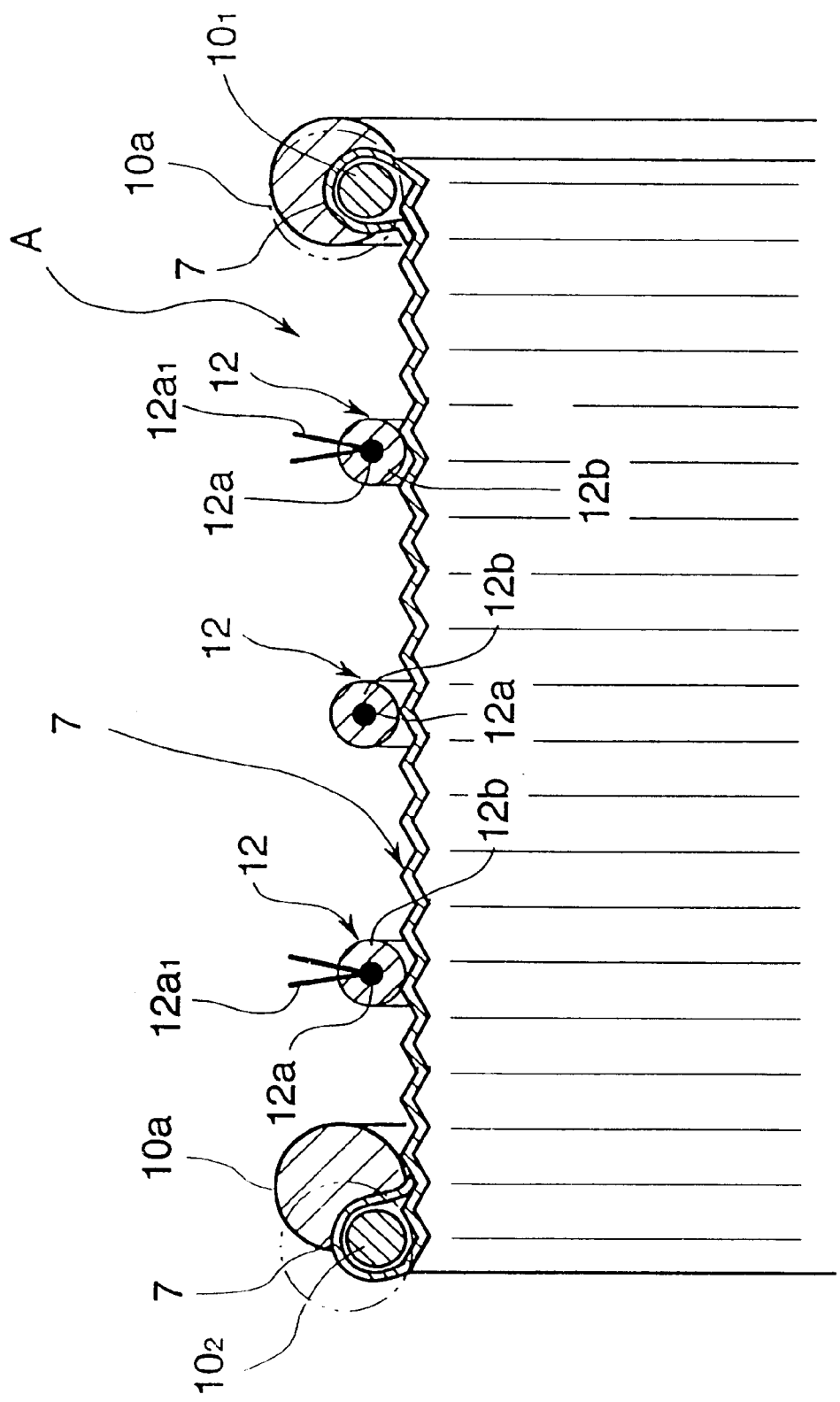
FIG. 2 is a vertical cross-sectional view of part of the artificial blood vessel.

The cover 7, as shown in FIG. 2, consists of a flexible, tensile sheet shaped into a tube of bellows, the normal diameter of which generally corresponds to the shape of that portion of the human blood vessel at which the artificial blood vessel A is to be implanted. The sheet of the cover 7 is, for example, of warps extending in the axial direction of the artificial blood vessel A woven with wefts extending in the circumferential direction thereof, wherein the warps are of mono-filament made of polyester (about 15 denier) and the wefts are of multi-filament made of a plurality of superfine filaments (about 50 denier) interwoven. The wefts are additionally woven with thread of polyethylene of about 10 denier to make the sheet of the cover 7 thinner and stronger. The cover 7 is coated, if necessary, with waterproof material, for example, collagen or albumin, to prevent leakage of blood.

The front and rear end wire rings $10_1$, $10_2$, whose inner diameter generally corresponds to that of the above-mentioned cover 7, are axially spaced apart and arranged face to face, and are fixed to the apposite ends of the cover 7 by suturing or with adhesive as shown in FIG. 2. As shown in FIG. 1, loop-shaped front hooking means 13 are formed at a pair of dividing points $41_1$ and $43_1$ facing each other across the axis of four dividing points $41_1$, $42_1$, $43_1$, $44_1$ each of which equally quadrisects the circumference of the front end wire ring $10_1$. The hooking means 13 in accordance with the embodiment are formed of string. It may not necessarily be of string, but a hole directly formed on the cover 7 may be utilized as the hooking means, if there is no trouble. The circumferences of the front and rear end wire rings $10_1$, $10_2$ are covered with protective braid members $10a$, as shown in FIGS. 1 and 2, which are closely fixed to the end wire rings $10_1$, $10_2$ at appropriate positions with thread, adhesive or the like. The protective braid members $10a$ are made of, for example, polyester fiber tied up in a bundle like cotton. For especially small in diameter blood vessels into which the artificial blood vessel A is to be implanted the protective braid members $10a$ are preferably attached to the positions displaced ahead to the end wire rings $10_1$, $10_2$. This is because the protective braid members $10a$ can be pushed to move to appropriate positions at which adjacent the end wire rings $10_1$, $10_2$ is covered as shown imaginary lines in FIG. 2 when transporting resistance is applied to.

A plurality of intermediate wire rings 12, each of which comprises, as shown in FIGS. 1 through 4, wire rings $12a$ wrapped with protective film $12b$ made of cloth or the like, are arranged axially and general-equidistantly spaced between the front and rear end wire rings $10_1$ and $10_2$, and fixed to the cover 7 at specified positions on the circumference thereof with thread, adhesive or the like. The specified positions are the points $51_3$, $52_3$, $53_3$, and $54_3$ on the circumfernee each of which corresponds to the midpoint $51_1$ between the dividing points $41_1$, $42_1$ of the end wire ring $10_1$, the midpoint $52_1$ between the dividing points $42_1$, $43_1$, the midpoint $53_1$ between the dividing points $43_1$, $44_1$ and the midpoint $54_1$ between the dividing points $44_1$, $45_1$ respectively, more specifically, the points at which each of the generatrices $l_1$, $l_2$, $l_3$, and $l_4$ passing through the midpoints $51_1$, $52_1$, $53_1$, and $54_1$ of the end wire rings $10_1$ crosses the intermediate wire rings 12. The above-mentioned front and rear end wire rings $10_1$, $10_2$ and the intermediate wire rings 12 help keep the tubular shape of the cover 7.

Figure 3:
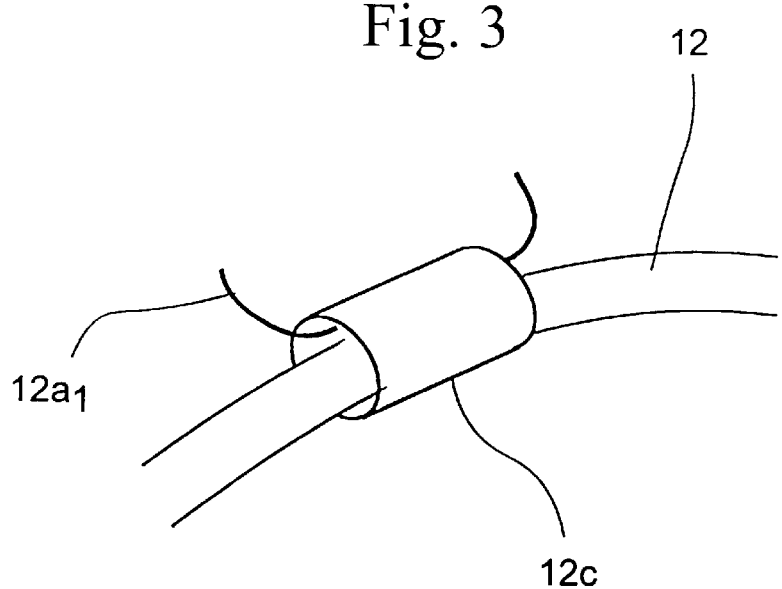
FIG. 3 is an enlarged perspective view of part of the intermediate wire ring constituting the artificial blood vessel.
Figure 4:
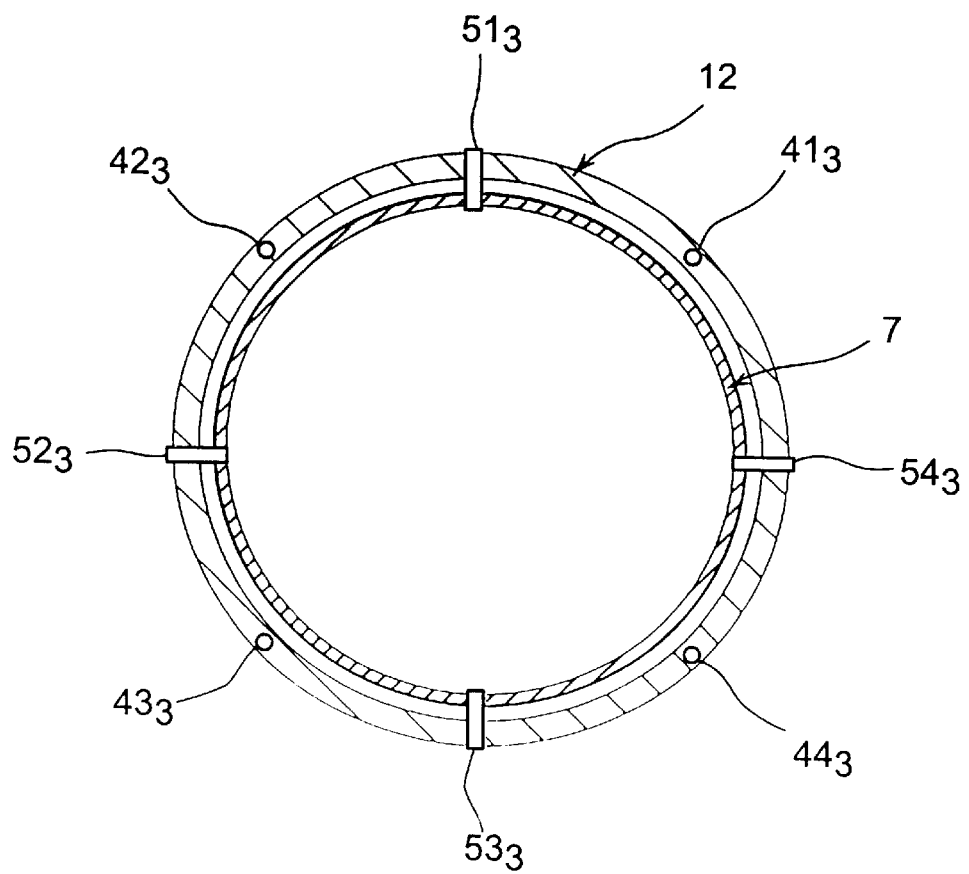
FIG. 4 shows a condition how the intermediate wire ring is fixed to the tubular cover.

Some of the intermediate wire rings 12 are provided with thorns $12a_1$ which are formed at two diametrically opposite positions on each of the circumference thereof and which stick into a human organ so as to be embedded therein. In particular, the wires $12a$ of the intermediate rings 12 as well as those of the front and rear end wire rings $10_1$, $10_2$ are made of Ti—Ni alloy or the like. The wires of Ti—Ni alloy have a high resilient restoring force, but are hard to weld. Then as shown in FIG. 3, a partially cylindrical shaped fixing member $12c$ into which the intermediate wire zing 12 is loosely inserted and a thorn $12a_1$ preformed into U-shape or V-shape are prepared. Then the thorn $12a_1$ is passed through and inserted into the gap between the intermediate wire ring 12 and the fixing member $12c$. And finally the fixing member $12c$ is riveted and bound with a string or the like so as to fix the thorn $12a_1$ to the intermediate wire ring 12. The positions at which each of the thorns $12a_1$ is provided correspond to the above-mentioned positions $51_3$, $52_3$, $53_3$ and $54_3$.

In order to implant the artificial blood vessel A of the above-mentioned construction into a target organ of a human body, a device B for transporting the artificial blood vessel (see FIG. 5) is used to transport the artificial blood vessel A to the target organ of the human body through the catheter 8 and a device C for introducing the artificial blood vessel (see FIG. 6) is used to introduce the artificial blood vessel A into the catheter 8.

Figure 5:
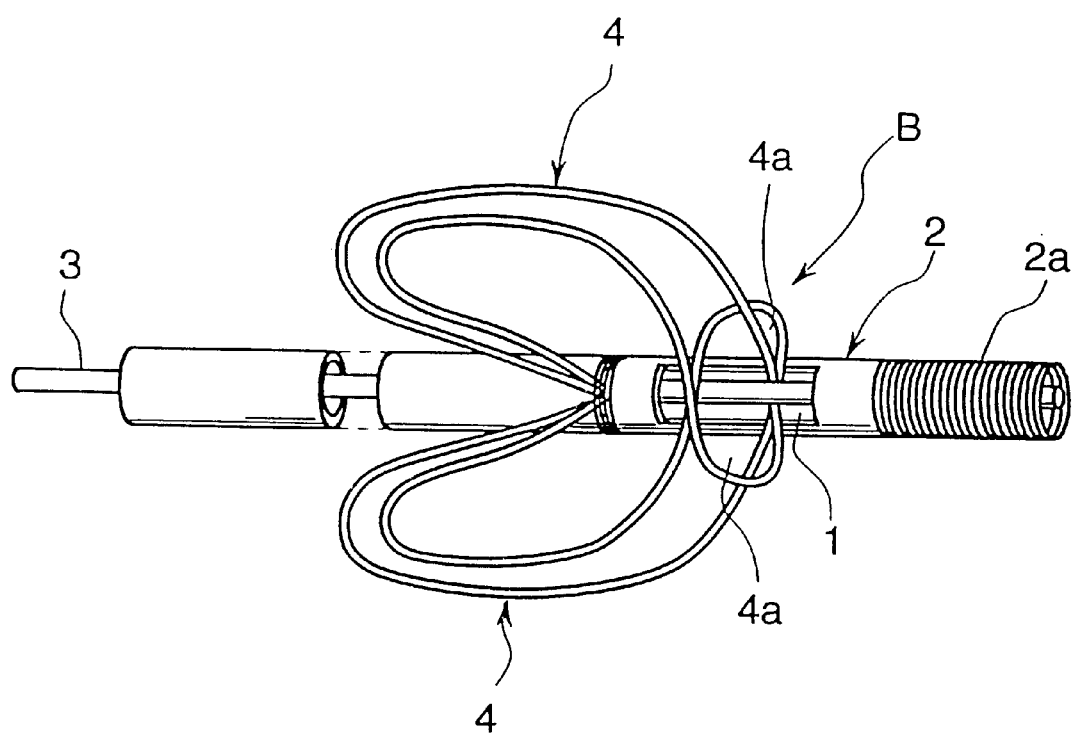
FIG. 5 is a perspective view of a device for transporting the artificial blood vessel, used in the embodiment.

The device B for transporting the artificial blood vessel, as shown in FIG. 5, comprises a flexible metallic tube 2 whose front end portion is connected to a helical spring $2a$ for guiding, a side window 1 formed adjacent the front end of the tube 2, a pair of strings 4 having both their ends fixed to the tube 2 adjacent the side window 1 and their middle portions formed into loops to be looped portions $4a$, and a length of wire 3 slidably inserted into the tube 2. Instead of the above-mentioned helical spring $2a$ for guiding, a flexible tube may be used. The device for transporting the artificial blood vessel may comprise only the tube 2 and a length of wire 3, which will be described later.

Figure 6:
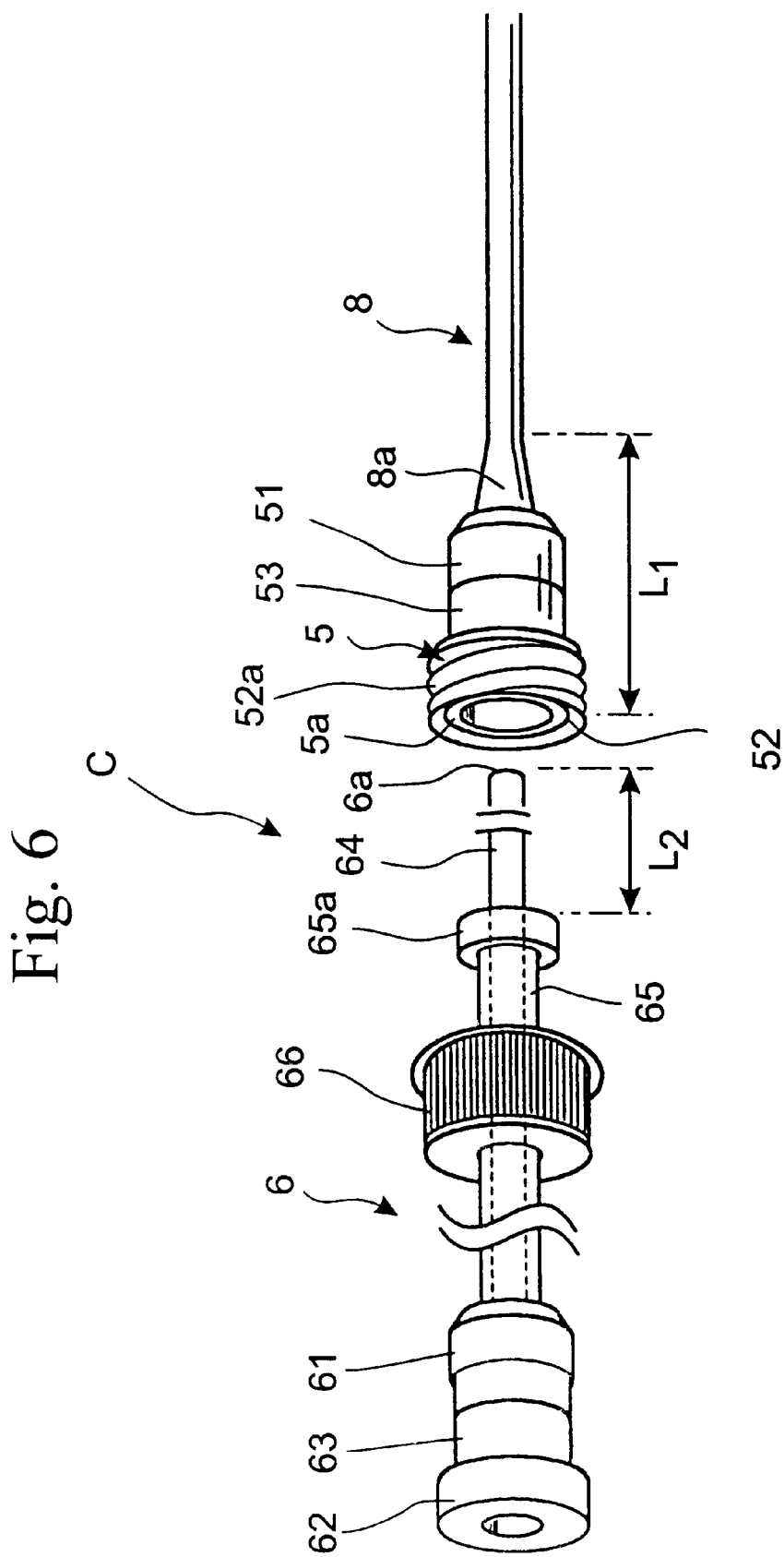
FIG. 6 is a perspective view of a device for introducing the artificial blood vessel, used in the embodiment.
Figure 7:
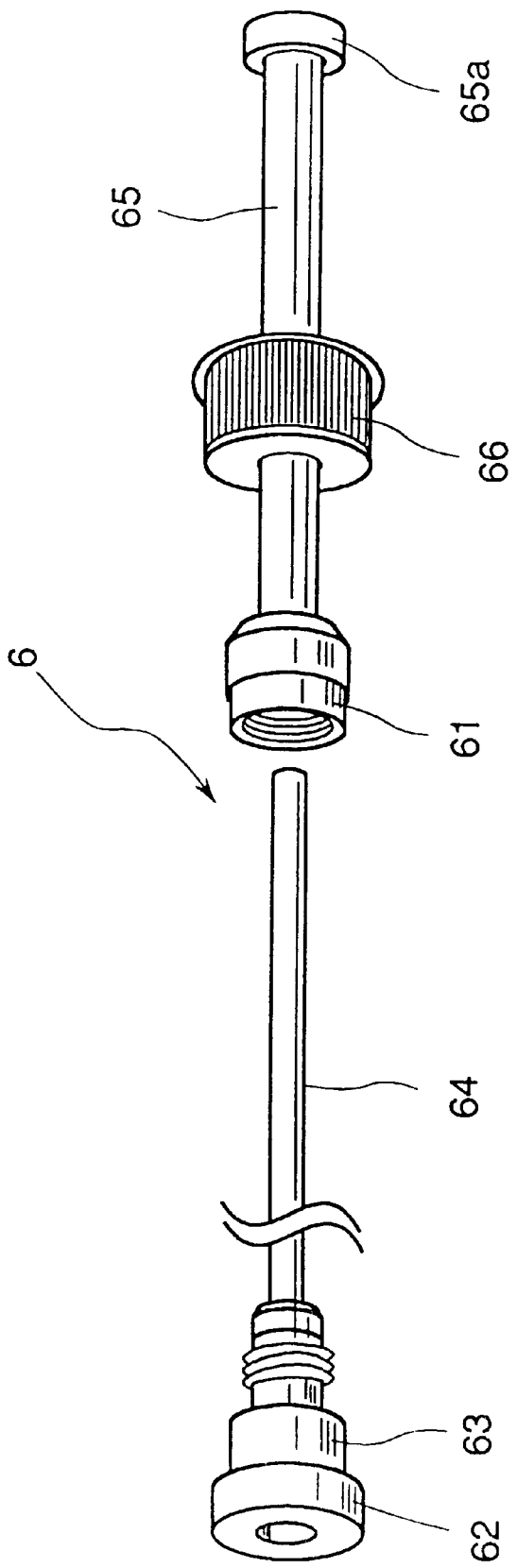
FIG. 7 is a perspective view of a cartridge constituting the device for introducing the artificial blood vessel.
Figure 8:
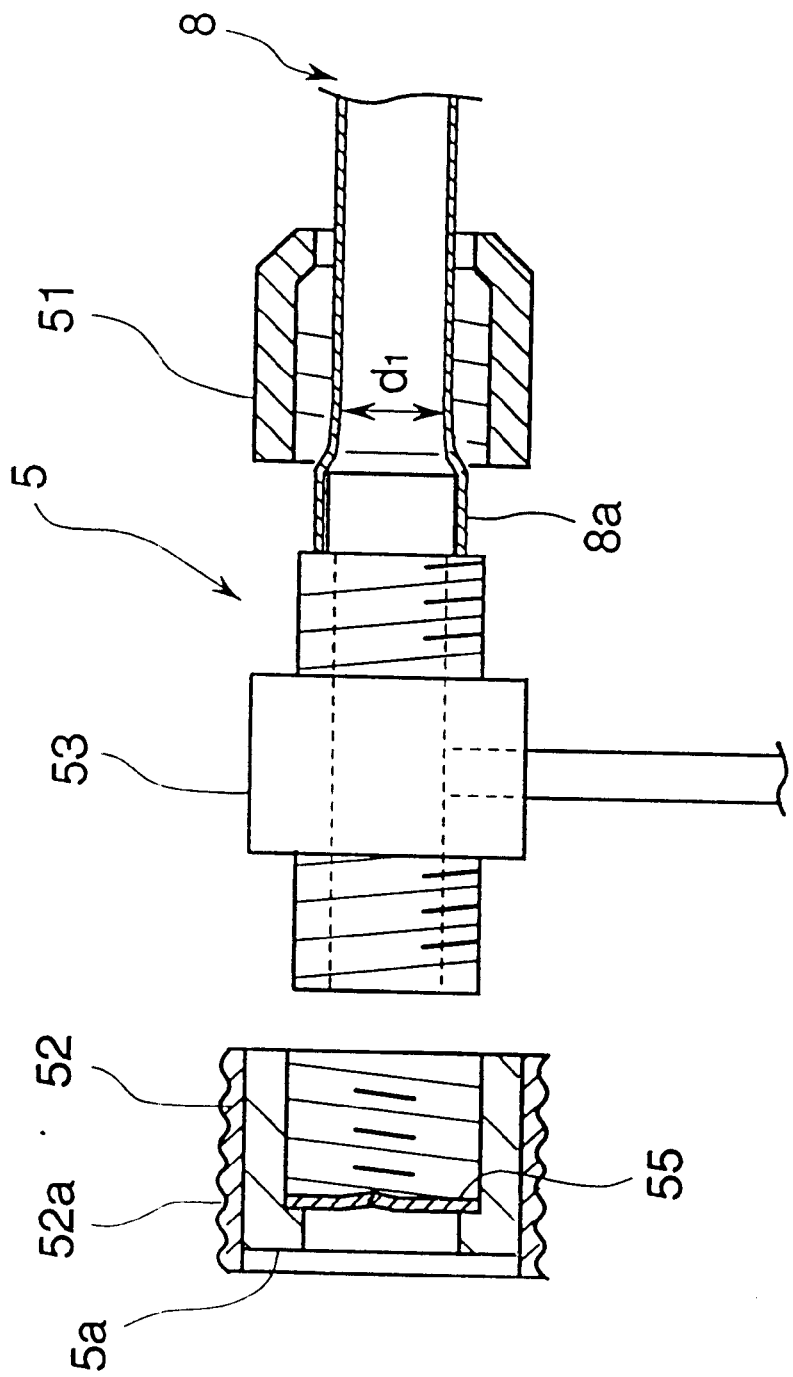
FIG. 8 is an enlarged vertical cross-sectional view of part of the attachment shown in FIG. 6.
Figure 9:
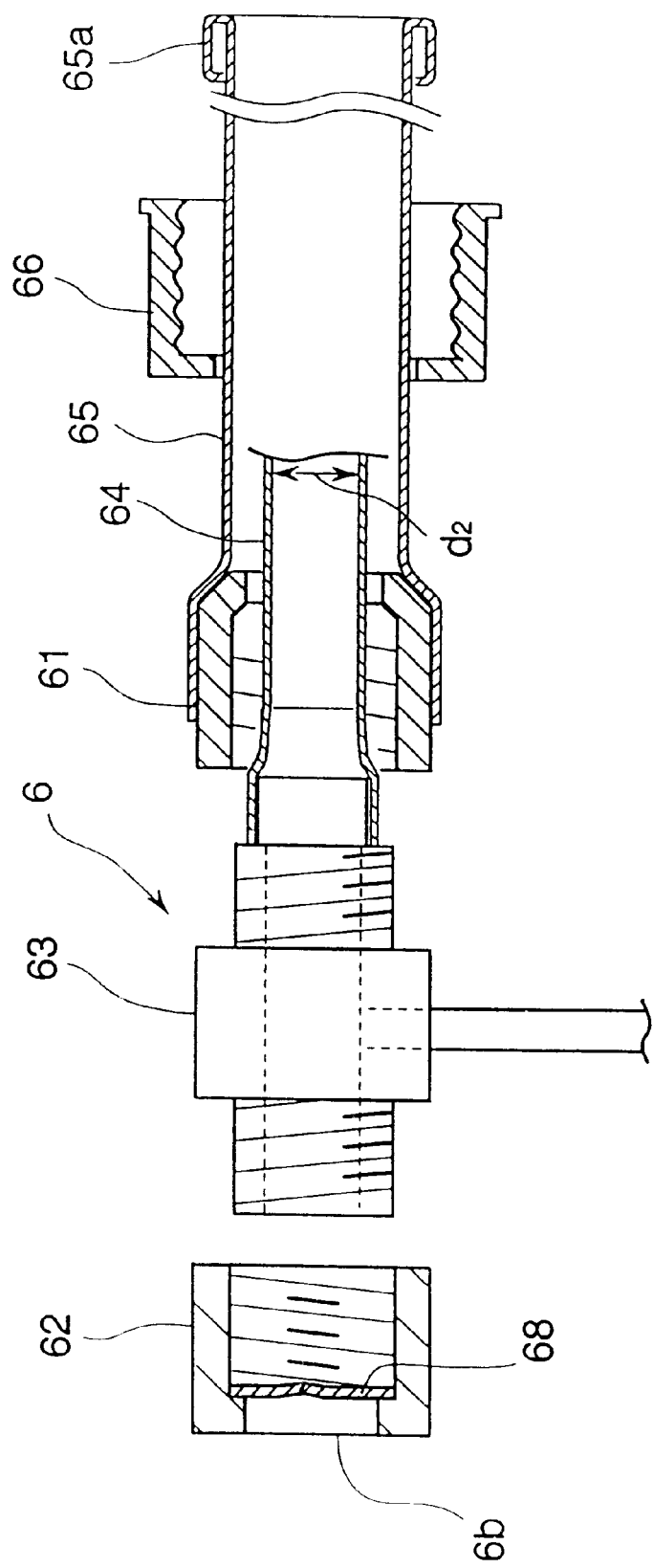
FIG. 9 is an enlarged vertical cross-sectional view of part of the cartridge shown in FIG. 6.

The device C for introducing the artificial blood vessel, as shown in FIG. 6, comprises an attachment 5 integrally connected to the catheter 8 through an open end $8a$ thereof, and a cartridge 6 removably attached to the attachment 5. As shown in FIGS. 6 and 8, the attachment 5 comprises a first and a second annular member 51, 52 which are internally threaded to form female screws, and a third annular member 53 which is externally threaded to form male screws at opposite ends, which engages the above-mentioned female screws thereby to connect the internal space of the first and the second annular members 51, 52 at its male screw part. The catheter 8 is formed to have an open end $8a$ of a little larger diameter and attached to the tip of the male screw of the above-mentioned third annular member 53 at its open end $8a$. Then the third annular member 53 is liquid-tightly joins the interior of the open end $8a$ of the catheter 8. Inside the second annular member 52 provided is a check valve 55 made of elastic membrane to close the open end thereof and outside of it fittingly provided is a cylinder-shaped helical member $52a$ having a helical groove. The cartridge 6, as shown in FIGS. 6, 7 and 9, comprises first and second annular members 61, 62 which are internally threaded to provide internal female screws, a third annular member 63 which is externally threaded to form male screws at apposite ends, which engage the above-mentioned female screws at opposite ends to connect the first and second annular members 61, 62, a straw member 64 whose rear end is liquid-tightly attached to the tip of one of the male screw parts of the third annular member 63 and the front end of which is extending toward the direction to which the cartridge 6 is inserted, a cylinder-shaped guide pipe 65 having an internal diameter which can contain the straw member 64, one of whose ends integrally connected to the first annular member 61 and the other end thereof provided with a big portion 65a, and a cap 66 which is slidably movable along the axial direction of the guide pipe 65 and loosely fit to the external of the guide pipe 65 and inside of which formed is a helical groove which helically connects the helical member 52a of the attachment 5. A check valve 68 made of elastic membrane is provided inside the second annular member 62 to close the open end thereof.

Figure 28:
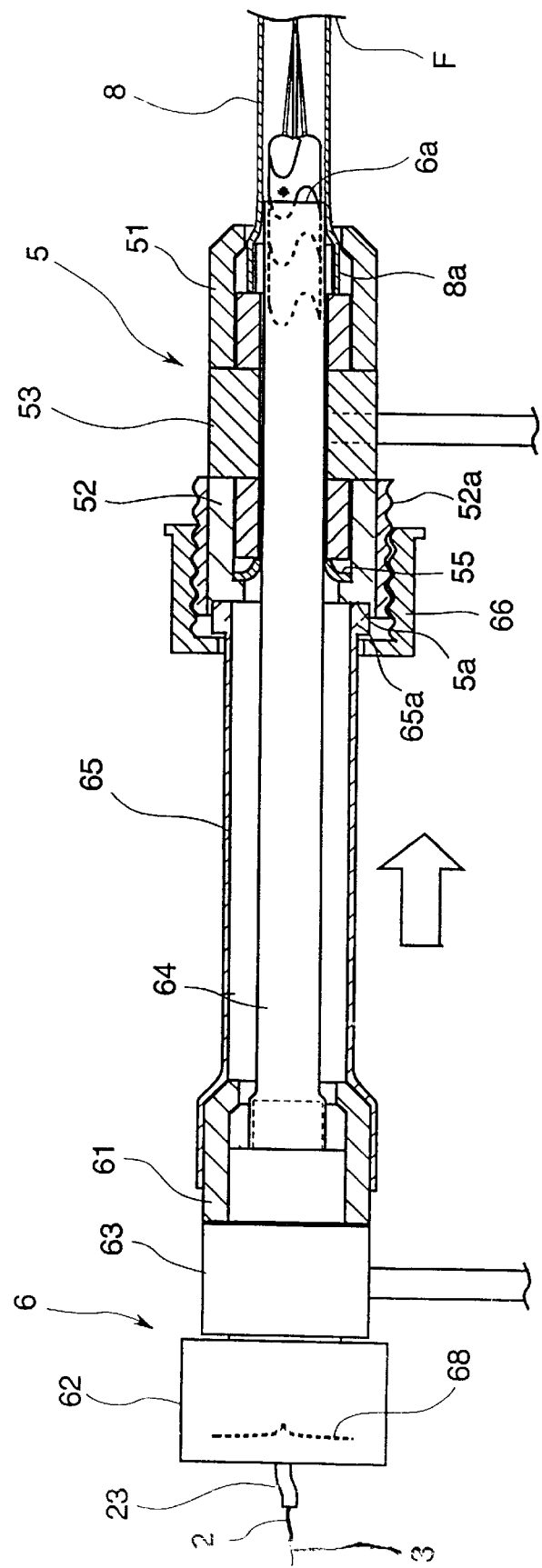
FIG. 28 is a partly cut-out side view showing the cartridge connected to the attachment.

As shown in FIG. 6, the straw member 64 of the cartridge 6 is so constructed that the front end portion 6a thereof is removably fitted into the rear end portion 5a of the attachment 5. In particular, as shown in FIGS. 6, 8, and 9, the bore diameter $d_1$ adjacent the open end 8a of the catheter 8 is set generally the same as or a little larger than the bore diameter $d_2$ of the straw member 64 of the cartridge 6, and the length $L_2$ of the straw member 64 extending from the big portion 65a of the guide pipe 65 is set approximately equal to the length $L_1$ between the end portion 5a of the attachment 5 and the position a little deep from the open end 8a of the catheter 8. The big portion 65a formed on one end of the cartridge 6 is made abutting engagement with the end portion 5a of the attachment 5 with the cap 66 helically mounted to the outer surface of the cylinder-shaped helical member 52a as shown in FIG. 28, and the front end portion 6a of the straw member 64 is inserted into the open end 8a of the catheter 8 so that the straw member 64 is smoothly connected to inside of the open end 8a of the catheter 8. The above-mentioned check valves 55, 68 are made of elastic membrane, in each of which a normally closed hole, not shown in drawings, is formed.

Figure 10:
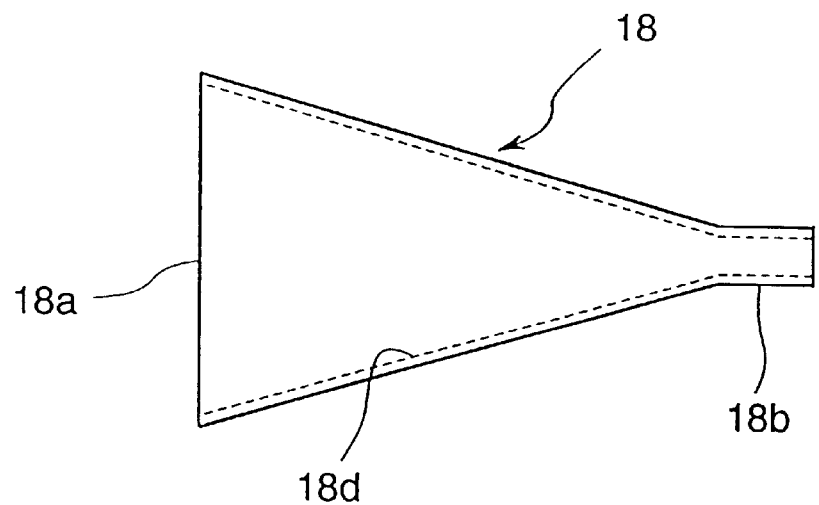
FIG. 10 is a side view showing a funneled tube, used in the embodiment.
Figure 11:
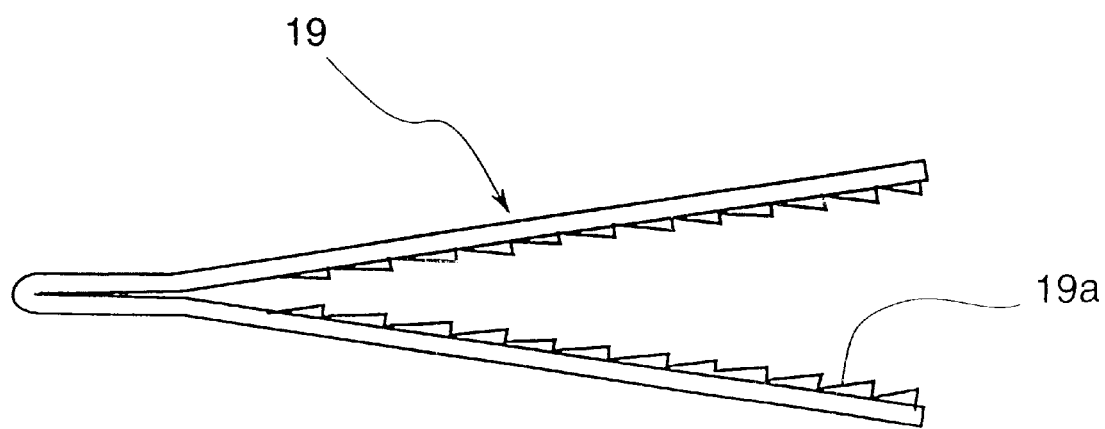
FIG. 11 is a side view showing forceps, used in the embodiment.
Figure 25:
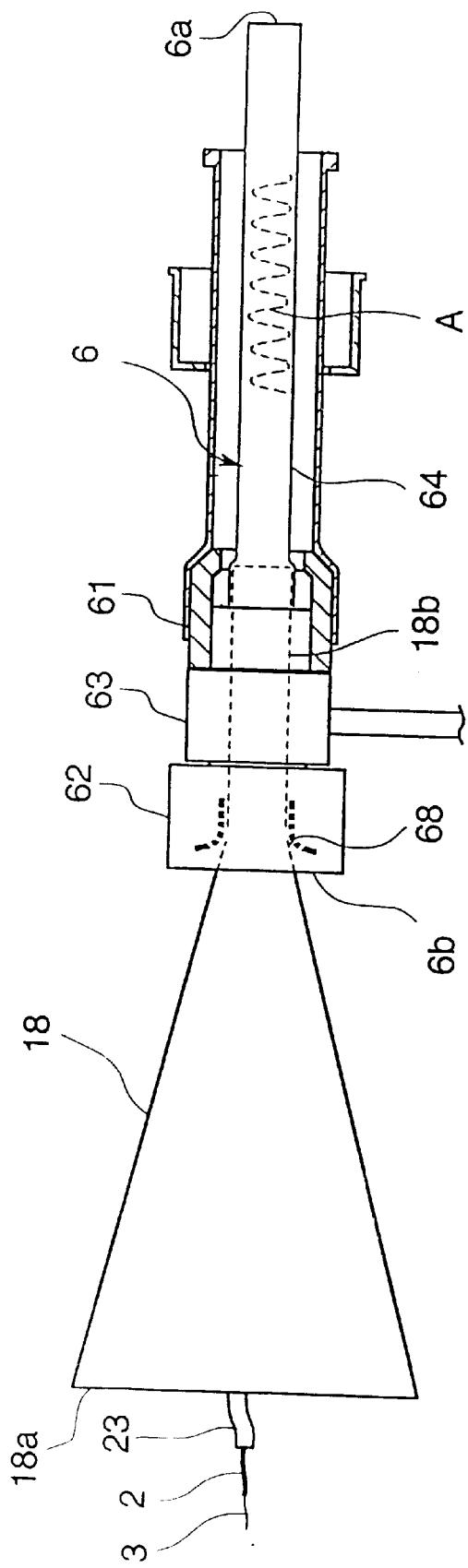
FIG. 25 is a partly cut-out side view showing the artificial blood vessel inserted into the cartridge.

A funneled tube 18 as a guide tube and forceps 19, as shown in FIGS. 10 and 11, are provided to help collapse the artificial blood vessel A. The funneled tube 18 is provided with an enlarged inlet opening 18a of an enlarged diameter at the rear end portion, through which the tubular artificial blood vessel A is inserted into the funneled tube 18. The funneled tube 18 is gradually reduced in diameter from the enlarged inlet opening 18a to end in a tubular connector 18b of a smaller diameter at the front end portion thereof, so that the tube 18 has a tapered inner surface 18d. The funneled tube 18 is, as shown in FIG. 25, removably connected to the cartridge 6 by inserting the front connector 18b into the rear end portion 6b of the cartridge 6. The forceps 19 are used for picking the artificial blood vessel A so as to insert it into the funneled tube 18. The forceps 19 are provided on its picking surface with an engaging member 19a having serrations against the direction to be inserted and for the direction to be pulled out so as to lessen the sliding resistance between the forceps 19 and the artificial blood vessel A when the forceps 19 are inserted relatively smaller than that when pulled out.

The process of collapsing the artificial blood vessel A and implanting it into a position to be implanted, namely, a target portion (an affected part 26 in FIG. 29) of a blood vessel 9 by means of the device B for transporting the artificial blood vessel and the device C for introducing the artificial blood vessel of the above-mentioned constructions, will now be described below.

Figure 12:
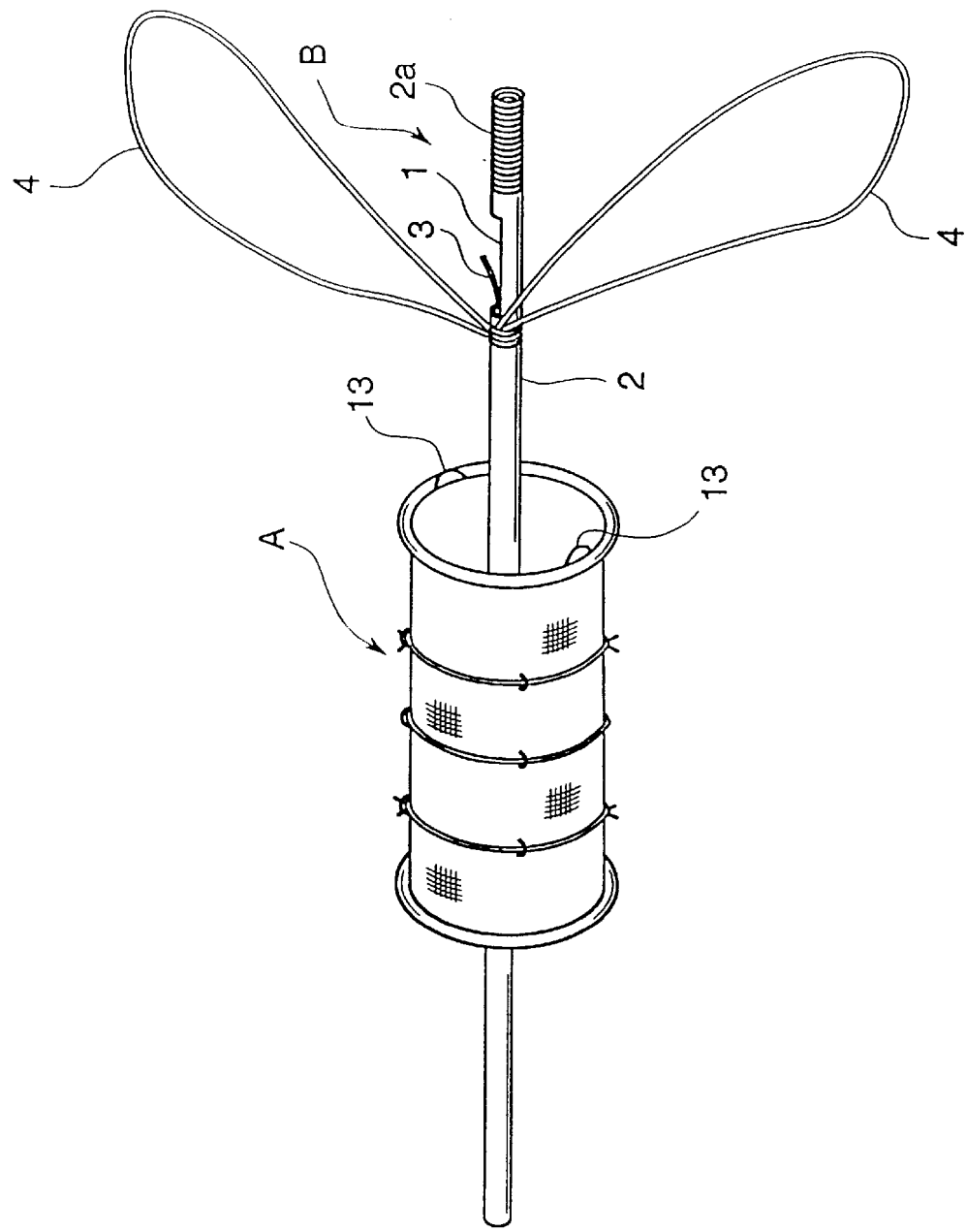
FIG. 12 is a perspective view of the artificial blood vessel through which the device for transporting the artificial blood vessel is loosely inserted.
Figure 13:
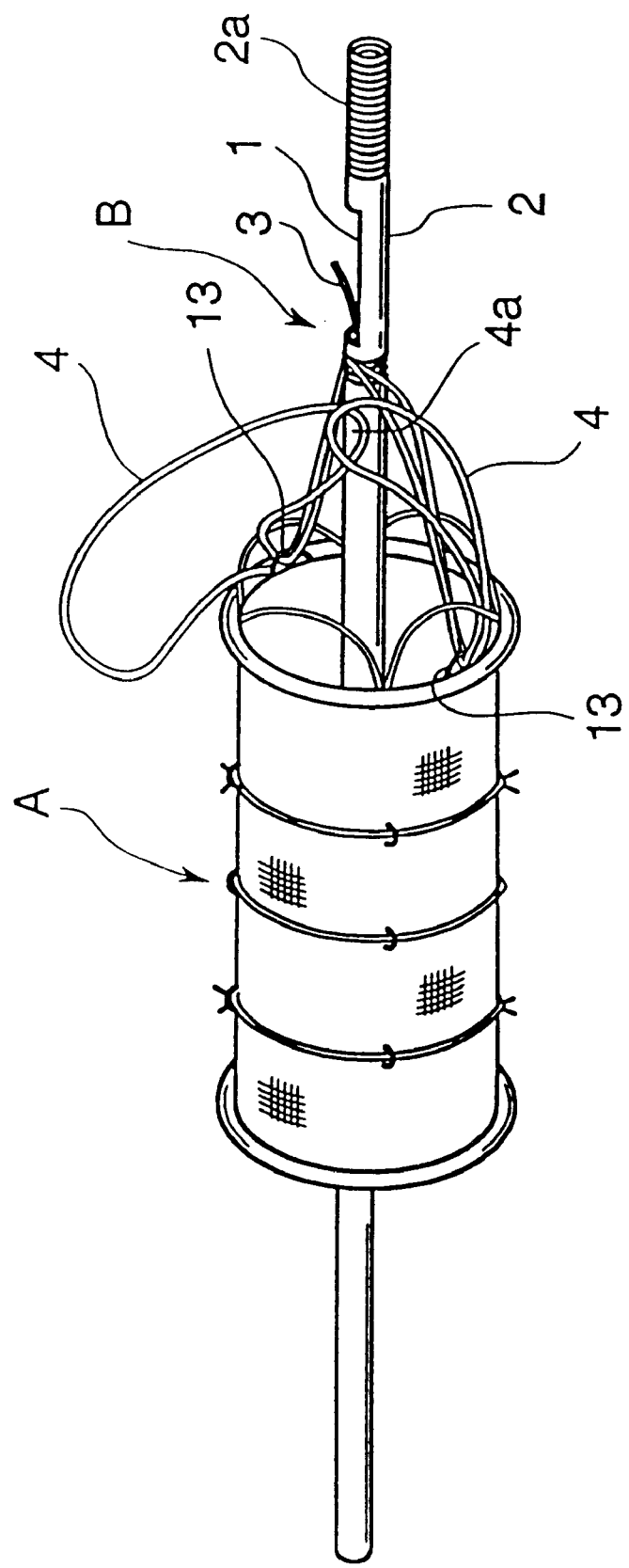
FIG. 13 is a perspective view showing a step to hold the artificial blood vessel by means of the device for transporting the artificial blood vessel.
Figure 14:
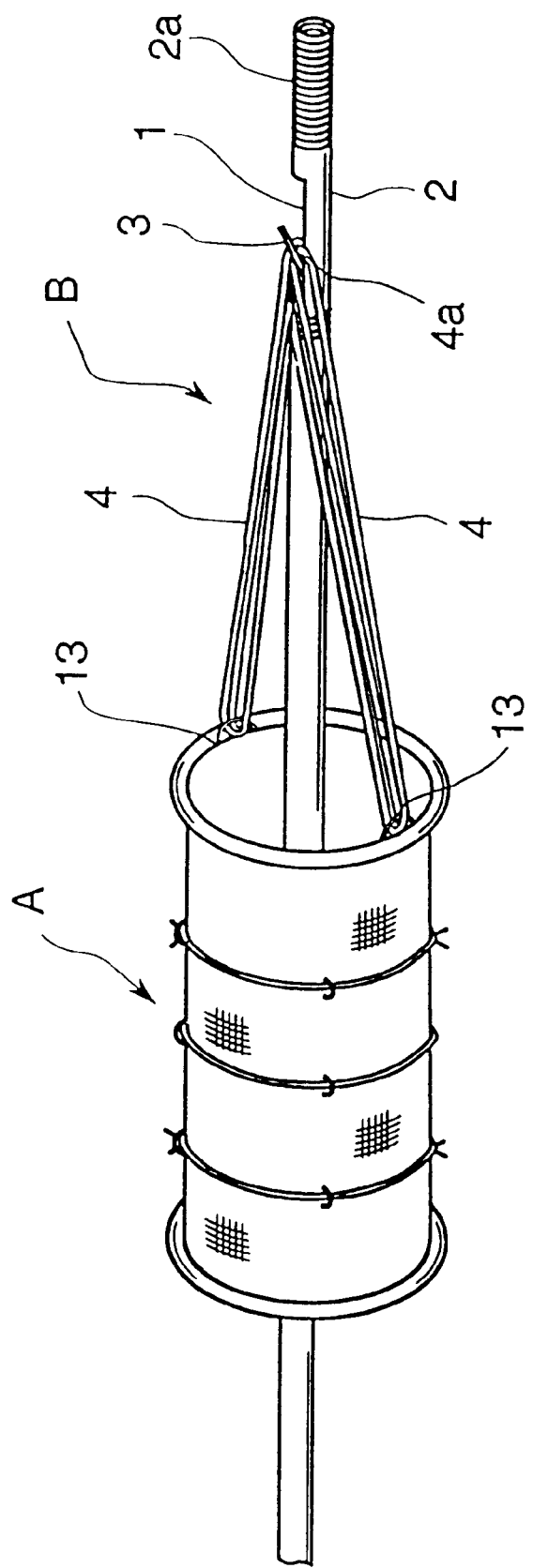
FIG. 14 is a perspective view showing a step to hold the artificial blood vessel by means of the device for transporting the artificial blood vessel.
Figure 15:
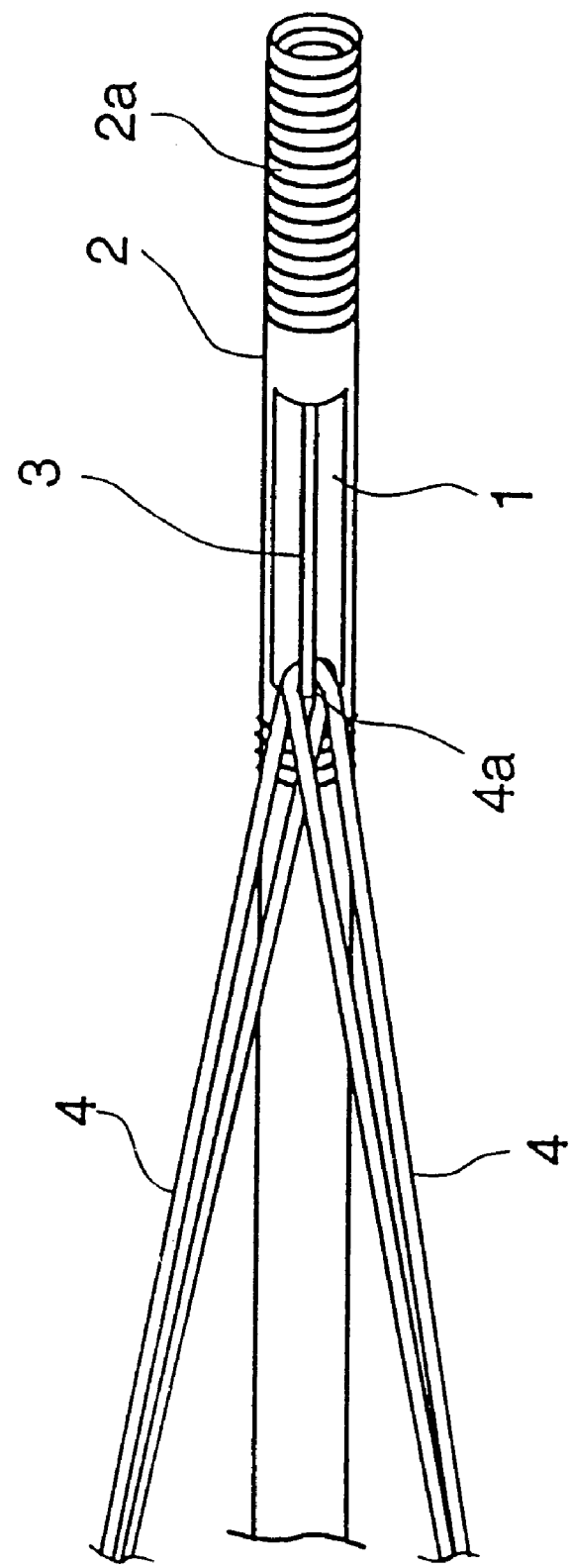
FIG. 15 is an enlarged perspective view showing part of the artificial blood vessel kept by the device for transporting the artificial blood vessel.
Figure 16:
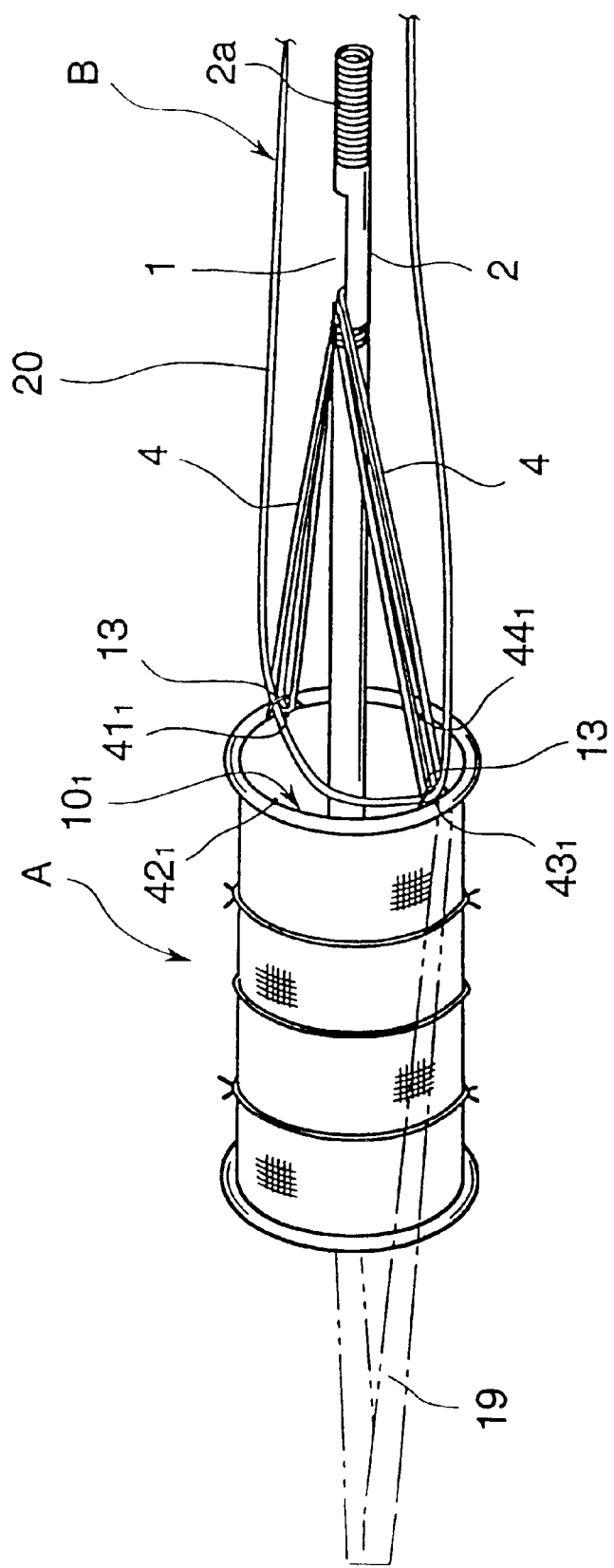
FIG. 16 is a perspective view showing a step to introduce the artificial blood vessel into a catheter.
Figure 17:
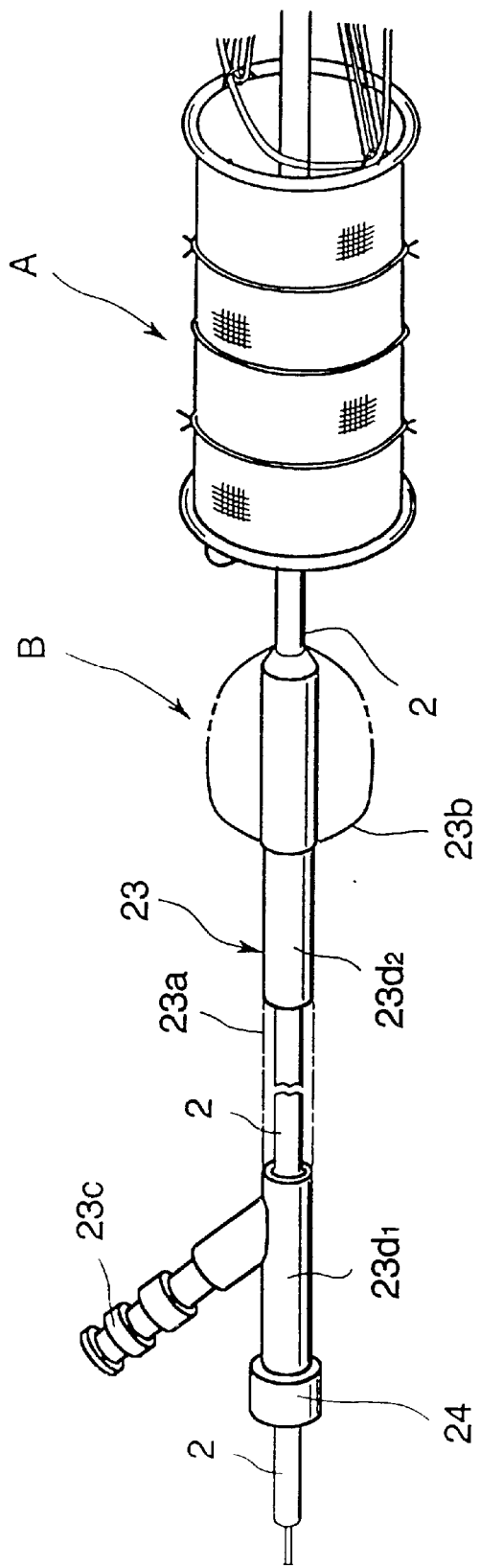
FIG. 17 is a perspective view showing a step to introduce the artificial blood vessel into the catheter.

First, the tube 2 of the device B for transporting the artificial blood vessel is inserted through the artificial blood vessel A as shown in FIG. 12, and each of a pair of strings 4 is passed through each hooking means 13 of the artificial blood vessel A as shown in FIG. 13, and the looped portions of the strings 4 overlap as shown at 4a. Next, a wire 3 has its forward end taken out of the side window 1 as shown in FIG. 14, and the overlapped portions of the looped portions 4a are hooked over the wire 3, and then the wire 3 has its forward end inserted again into the tube 2 through the side window 1 so as to hold the artificial blood vessel A on the wire 3 and the tube 2 through the strings 4 as shown in FIG. 15. Then, the artificial blood vessel A is inserted into the cartridge 6 shown in FIG. 6 through the funneled tube 18 and with the forceps 19. In particular, the forceps 19 are put along the generatrices each of which passes through the dividing points $41_1$ and $43_1$ with a common front pull string 20 being passed through the front hooking means 13 provided at the dividing points $41_1$, $43_1$ on the front end wire ring $10_1$ of the artificial blood vessel A as shown in FIG. 16. Prior to this operation a balloon catheter 23, as shown in FIG. 17, may be attached to the tube 2, if necessary. The balloon catheter 23 comprises a pipe 23a, a balloon 23b formed on the front end portion of the pipe 23a, and an opening 23c provided in the rear end of the pipe 23a for air to be introduced into or taken out of the above-mentioned balloon 23b through the pipe 23a. The pipe 23a is loosely fitted over the tube 2 of the above-mentioned deice B for transporting the artificial blood vessel. In other words, the rear end portion of the tube 2 of the device B for transporting the artificial blood vessel is drawn outside from the rear end of the balloon 23b of the balloon catheter 23 while the front end portion of the tube 2 is passed through the balloon 23b of the balloon catheter 23 and exposed outside, with the portions of the catheter 23 through which the tube 2 is passed being airtightly sealed. The rear end portion of the pipe 23a is removably connected to the tube 2 of the device B for transporting the artificial blood vessel by a fixing member 24, and the balloon catheter 23 and the tube 2 of the device B for transporting the artificial blood vessel can be moved together as a unit longitudinally when the fixing member 24 is fastened, and the balloon catheter 23 can be moved longitudinally relative to the tube 2 of the device B when the fixing member 24 is loosened. The balloon catheter 23 is so positioned that the front end thereof is spaced about 2 to 3 cm apart from the rear end of the artificial blood vessel A loosely fitted over the tube 2. Then the fixing member 24 on the balloon catheter 23 is fastened to fix the catheter 23 to the tube 2 so that the catheter 23 and the tube 2 can be moved together as a unit.

Figure 18:
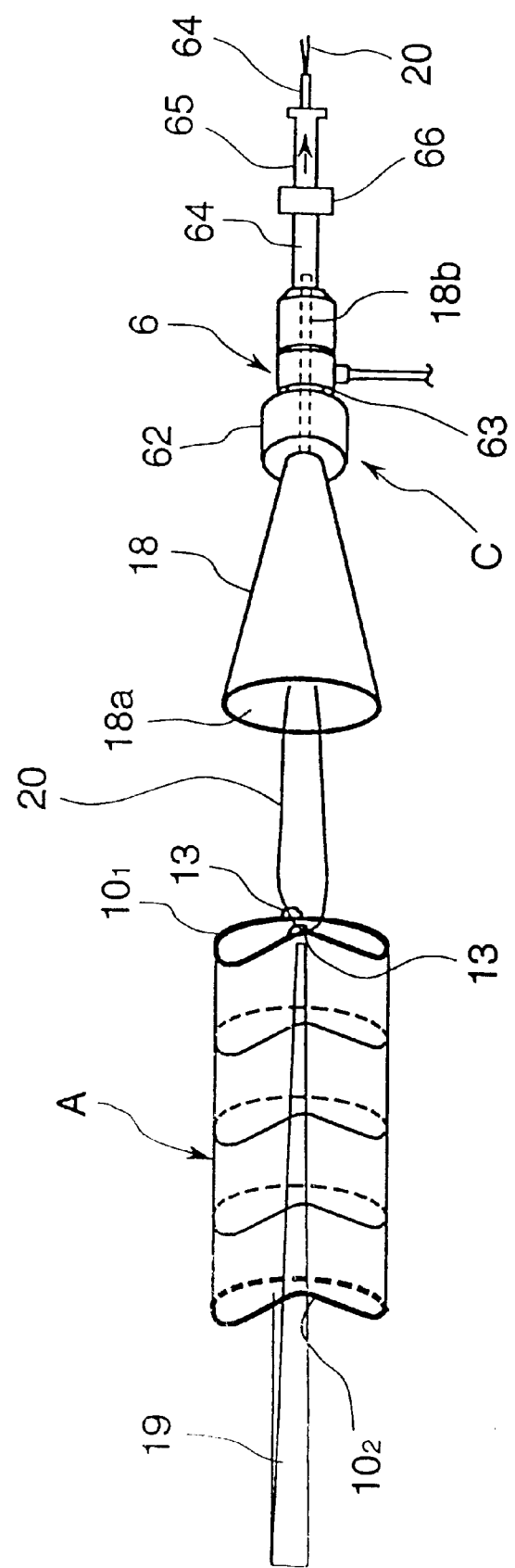
FIG. 18 is a perspective view showing a step to introduce the artificial blood vessel into the catheter by means of the forceps.

Before or after the above step, the funneled tube 18 is attached to a cartridge 6 as shown in FIG. 18. In attaching the funneled tube 18 to the cartridge 6, the connector 18b of the funneled tube 18 is inserted into the annular member 62 of the cartridge 6 so that the check valve 68 of elastic membrane provided inside the annular member 62 is pushed open by the connector 18b of the funneled tube 18 as shown in FIG. 25, and the connector 18b is inserted a little deep into the straw 64 of the cartridge 6. Then the artificial blood vessel A is inserted into inside of the funneled tube 18 through the enlarged inlet opening 18a with picked by forceps as shown in FIG. 18. The front pull string 20 is inserted into the funneled tube 18 tough the enlarged inlet opening 18a thereof and withdrawn forward through the straw 64 at the front end of the cartridge 6, with the tube 2 inserted a certain length into the funneled tube 18. Under the condition, the front pull string 20 is pulled forward to introduce the artificial blood vessel A into the funneled tube 18 through the enlarged inlet opening 18a thereof.

Figure 19:
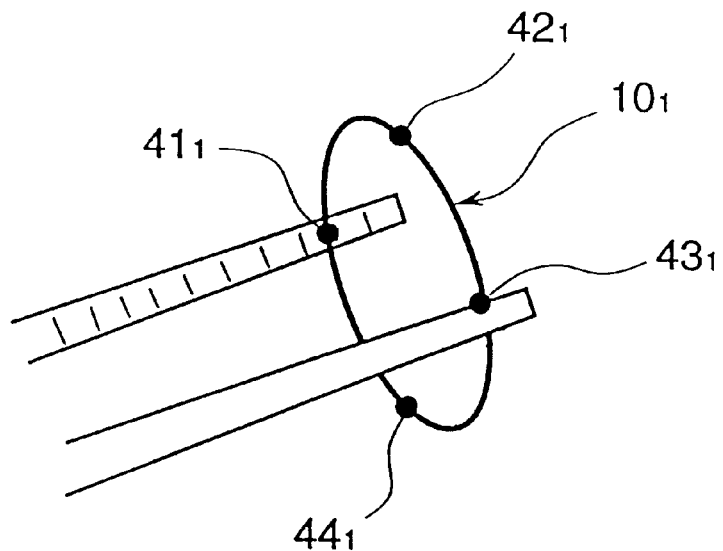
FIG. 19 shows the front end wire ring of the artificial blood vessel being folded.
Figure 20:
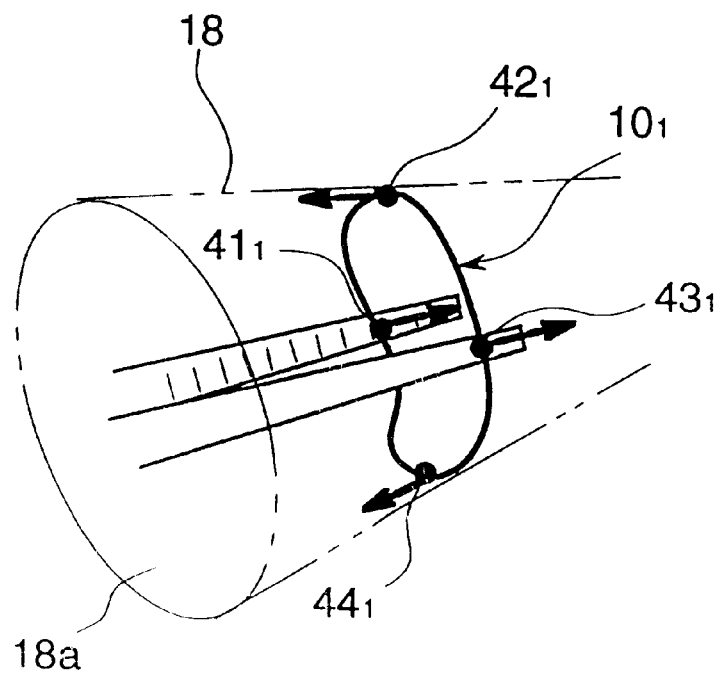
FIG. 20 shows the front end wire ring of the artificial blood vessel being folded.
Figure 21:
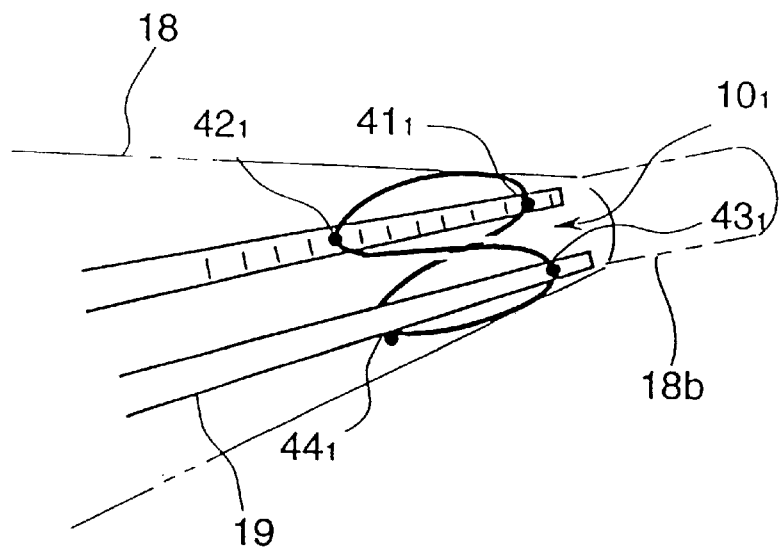
FIG. 21 shows the front end wire ring of the artificial blood vessel being folded.
Figure 22:
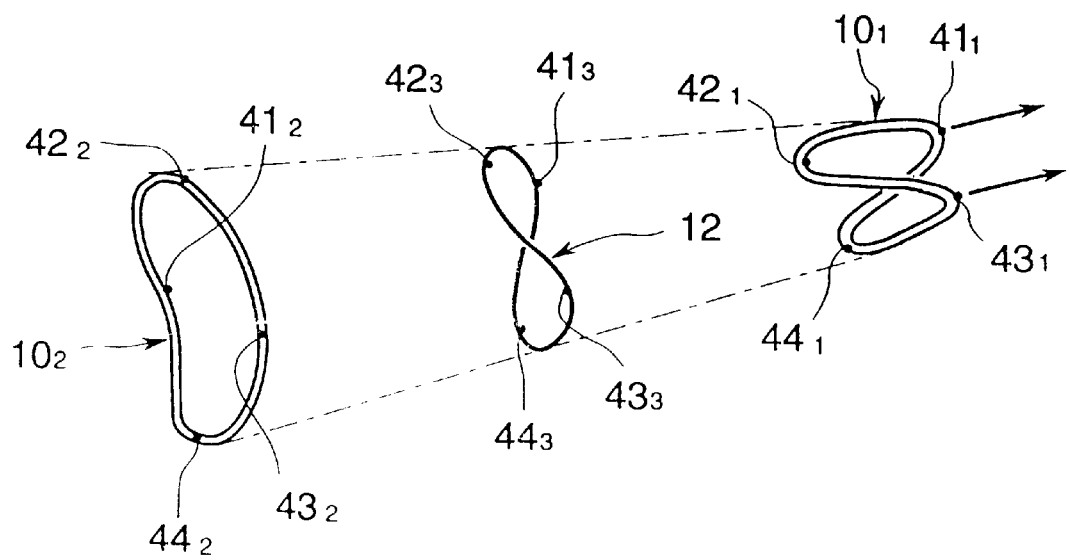
FIG. 22 shows the front end wire ring of the artificial blood vessel being folded in a funneled tube.
Figure 23:
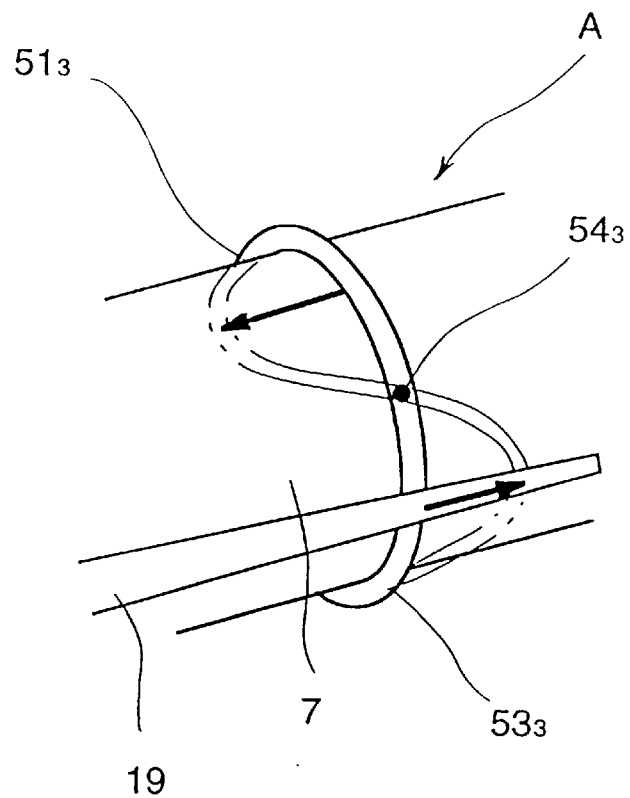
FIG. 23 is a perspective view showing the intermediate wire rings of the artificial blood vessel being folded.
Figure 24:
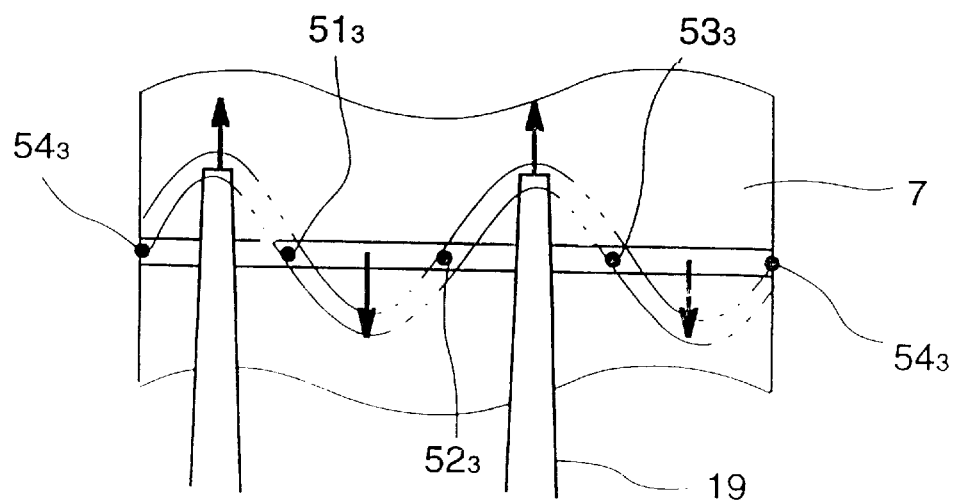
FIG. 24 is an expanded view showing the intermediate wire rings of the artificial blood vessel being folded.

Then the front end wire ring 10₁ of the artificial blood vessel A is deformed to be flat as shown in FIGS. 19 and 20 with the positions picked up by the forceps 19, namely the dividing points 41₁, 43₁ approaching toward each other to be pushed into the funneled tube 18 while the other dividing points 42₁, 44₁ restrained from the movement toward the tubular connector 18b by sliding contact with the tapered inner surface 18d of the funneled tube 18. When the front end wire ring 10₁ reaches adjacent the tubular connector 18b of the funneled tube 18, the front end wire ring 10₁ as a whole is folded into a regular wavy shape with the dividing points 41₁, 43₁ forming forwardly directed peaks and other dividing points 42₁, 44₁ forming the bottoms of forwardly directed valleys. The intermediate wire rings 12 and the rear end wire ring 10₂ also begin to transform into a wavy shape having the same phase as that of the front end wire ring 10₁, as shown in FIG. 22, because both of them follow the movement of the front end wire ring 10₁ toward the tubular connector 18b with picked by forceps 19. If focused on the intermediate wire ring 12, as the intermediate wire ring 12 is, as shown in FIGS. 23 and 24, fixedly attached to the tubular cover 7 only at the points 51₃, 52₃, 53₃, 54₃ of the circumference thereof each of which corresponds to the midpoints between two adjacent dividing points, the points picked by the forceps 19 protrude forward and other points is left behind with the above-mentioned points 51₃, 52₃, 53₃, 54₃ serving as fulcrum, thereby to cause the intermediate wire ring 12 twisted and transformed into a wavy shape without dragging the tubular cover 7.

Figure 26:
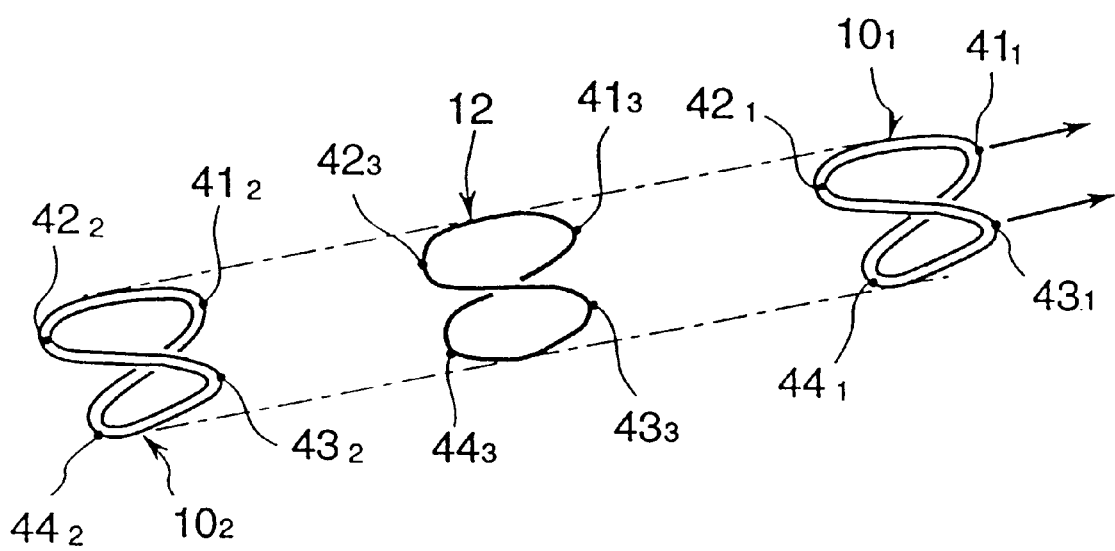
FIG. 26 is a diagram showing each of the wire rings being folded.

Under this condition, the forceps 19 are withdrawn from the funneled tube 18 and the front pull string 20 is pulled forward to farther introduce the artificial blood vessel A into the cartridge 6. As the front pull string 20 is pulled forward, the pulling force applied to the front end wire ring 10₁ is transmitted through the tubular cover 7 to the intermediate wire rings 12 and the rear end wire ring 10₂, thereby to cause the intermediate wire rings 12 and the rear end wire ring 10₂ to follow the movement of the front end wire ring 10₁. With the artificial blood vessel A perfectly contained in a cartridge 6 as shown in FIG. 25, the intermediate wire rings 12 and the rear end wire ring 10₂ are collapsed into a small size to take a wavy shape having the same phase as that of the front end wire ring 10₁ as shown in FIG. 26.

As the forceps 19 are provided with the above-mentioned serrate engaging member 19a, they can pick up and push the artificial blood vessel A into the funneled tube 18 for certain while they can be withdrawn from the funneled tube 18 with leaving the artificial blood vessel A in the funneled tube 18 by slipping smoothly between the artificial blood vessel A and the funneled tube 18. As the rings 10₁ and 10₂ are folded, it is needless to say that the braid members 10a circumferentially arranged about the front and rear end wire rings 10₁, 10₂ are also folded to take a wavy shape with following the front and rear end wire rings 10₁, 10₂.

Figure 27:
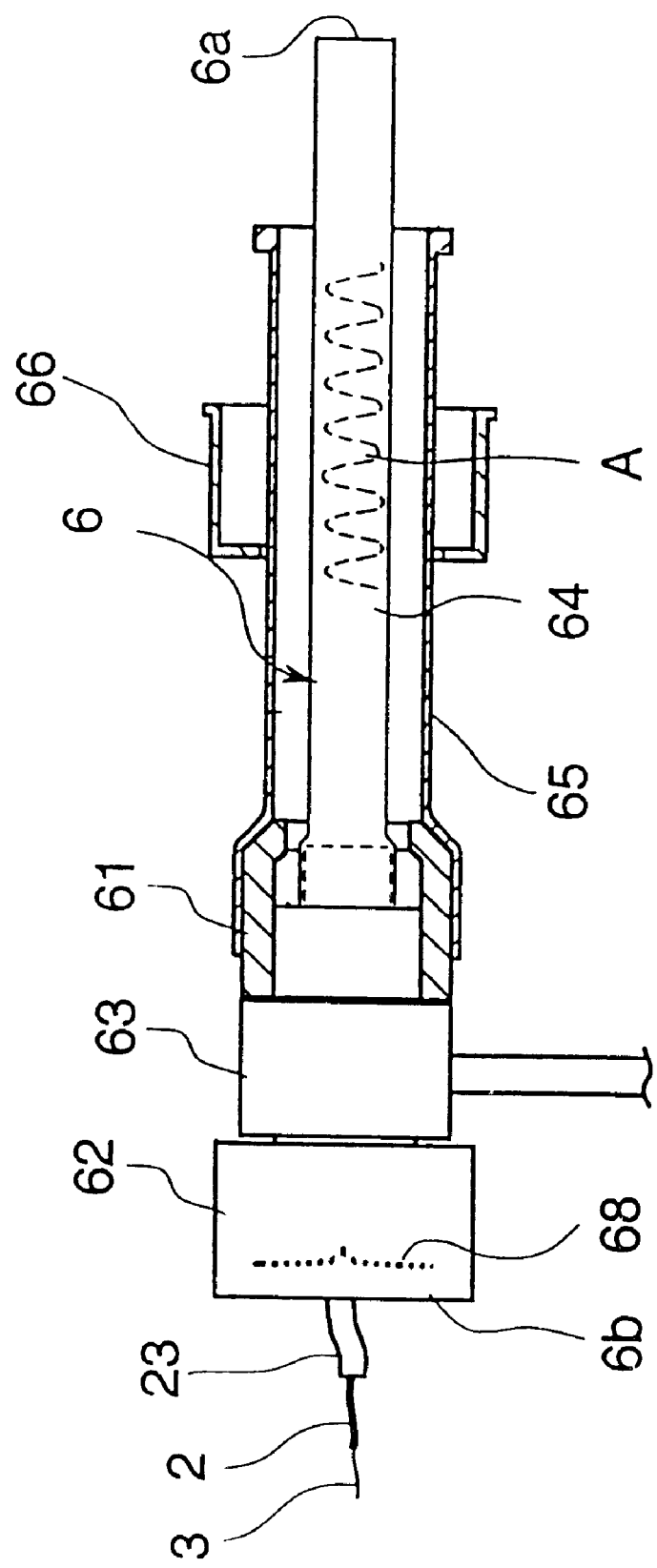
FIG. 27 is a partly cut-out side view showing the cartridge from which the funneled tube is drawn out.

Under the condition, the front pull string 20 is untied or cut at an appropriate position thereof and pulled at its end so as to be withdrawn from the front hooking means 13, and the funneled tube 18 is withdrawn from the cartridge 6. Consequently, the artificial blood vessel A is contained in the straw 64 of the cartridge 6, as shown in FIG. 27, and only the balloon catheter 23 in which the tube 2 is provided is exposed outside through the rear end portion 6b of the cartridge 6 with the check valve 68 opened a little.

Figure 29:
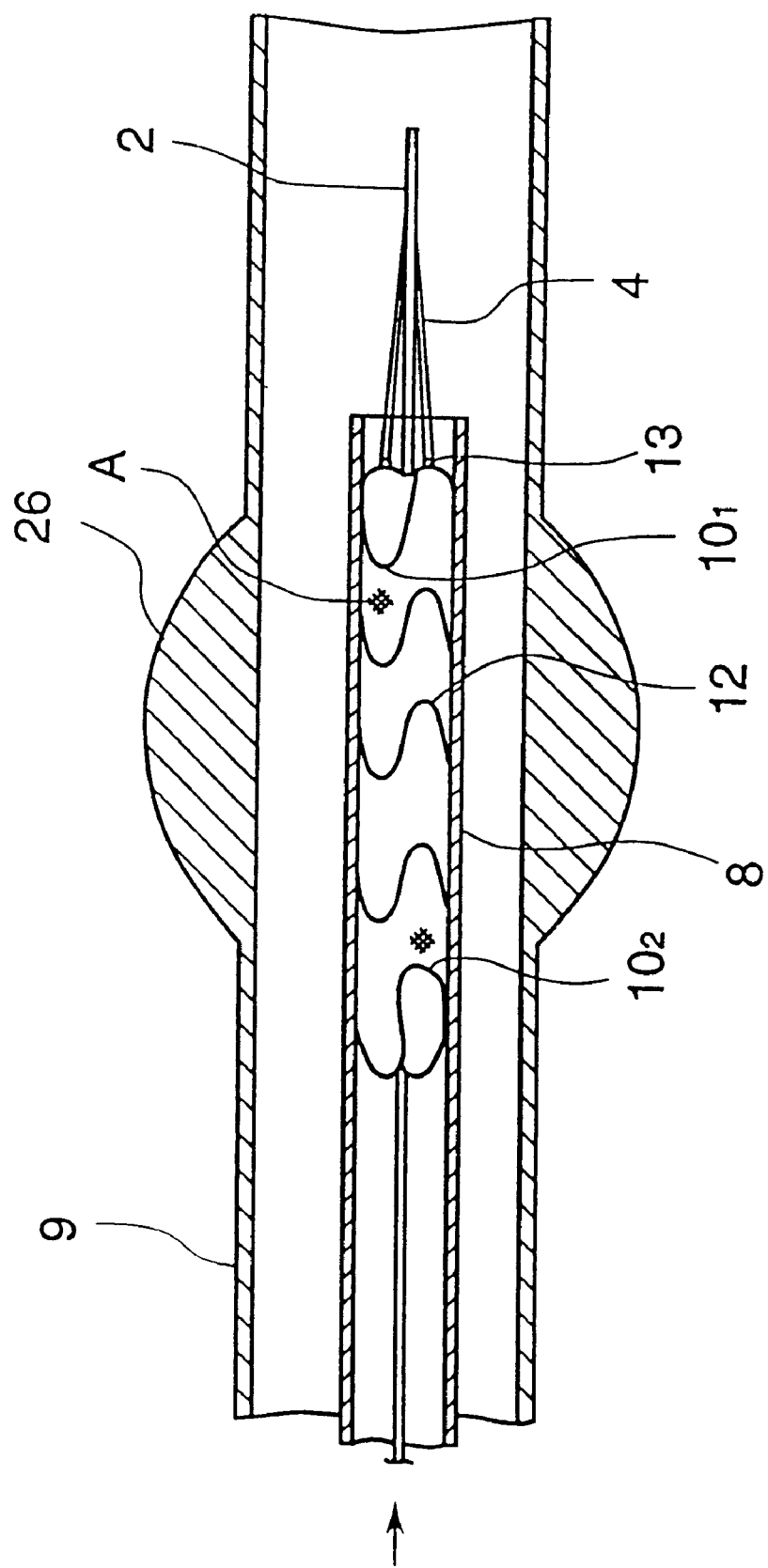
FIG. 29 is a cross-sectional view showing the artificial blood vessel transported to the affected portion.
Figure 30:
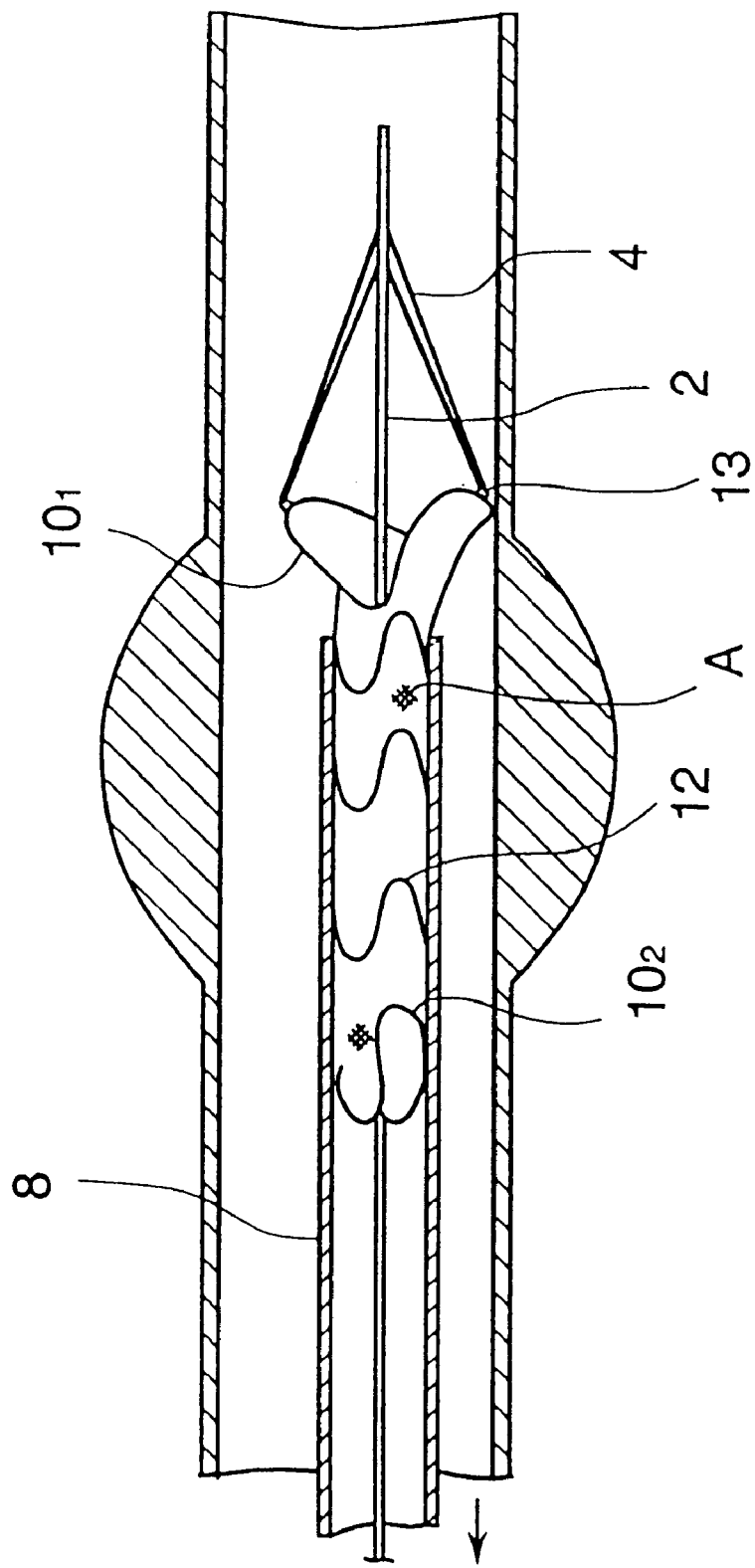
FIG. 30 shows a step to release the artificial blood vessel at an affected part in a blood vessel.
Figure 33:
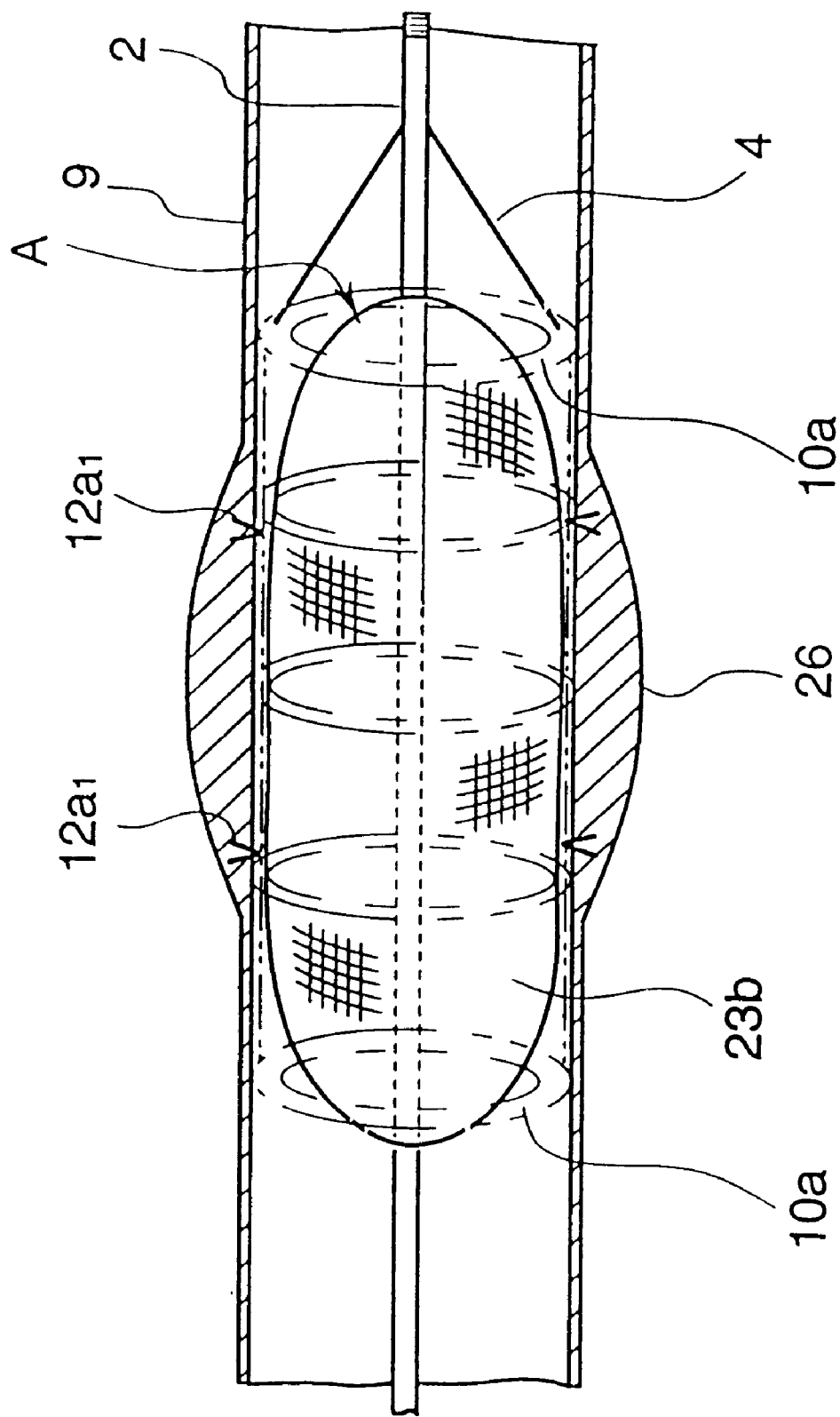
FIG. 33 shows a step to expand the artificial blood vessel by means of a balloon catheter.

On the other hand, the catheter 8 has been previously inserted through as shown in FIG. 28, for example, the coxal artery adjacent the groin F into the blood vessel 9 as far as the front end of the catheter 8 has been positioned a little beyond the affected portion 26 such as an aneurysm of the aorta as shown in FIG. 29. The attachment 5 connected to the open end 8a of the catheter 8 is, as shown in FIG. 28, exposed outside the body. Next, the straw 64 of the cartridge 6 into which the artificial blood vessel A has been inserted is pushed into the attachment 5 through the rear end portion 5a thereof until the big portion 65a makes abutting engagement with the rear end portion 5a with the check valve 5 opened as shown in FIG. 28 and the cap 66 is advanced to helically connect to the outer surface of the helical member 52a. Then the straw 64 of the cartridge 6 is positioned so that the front end 6a thereof is smoothly connected to the inner surface of the open end 8a of the catheter 8 and this condition is kept by the helical connection of the cap 66 and the helical member 52a. Under the condition, the balloon catheter 23 is gripped and the balloon catheter 23 is pushed so as to be inserted gradually deeply into the catheter 8. As the tube 2 is, as shown in FIG. 17, connected to the balloon catheter 23 through the fixing member 24 and the artificial blood vessel A is held by the tube 2, movement of the balloon catheter 23 causes the artificial blood vessel A to be transported gradually to the deep position in the body. The balloon catheter 23 is pushed until the front end of the tube 2 is positioned at the front end of the catheter 8, as shown in FIG. 29. At this time the artificial blood vessel A is positioned at the affected portion 26 as the target position. Then, as the catheter 8 is withdrawn as shown in FIG. 30, with the balloon catheter 23 and the tube 2 into which the wire 3 is inserted left at the objective position, the collapsed artificial blood vessel A in the catheter 8 is released at the affected portion 26 in the blood vessel 9 while expanding gradually from the front end as shown in FIGS. 30, 31 and 32. The released artificial blood vessel A is restored to its original tubular shape and urged against the inner wall of the blood vessel 9. In other words, when the artificial blood vessel A collapsed into small as shown in the figures is released from the catheter 23, each of the quadrisecting points elastically restores to a direction generally perpendicular to the blood vessel 9. Consequently, the artificial blood vessel A restores itself with each end portion thereof open and the internal space of the artificial blood vessel A is not closed by the internal wall of the blood vessel 9. Then the fixing member 24 shown in FIG. 17 is loosened to disconnect the balloon catheter 23 from the tube 2, and the balloon catheter 23 is advanced along the tube 2 into the artificial blood vessel A with the tube 2 kept at the objective position as far as the front end of the balloon catheter 23 reaches the front end of the artificial blood vessel A as shown in FIG. 33, whereupon the balloon 23b is inflated by introducing air through the opening 23c as shown in FIG. 33 thereby to restore the artificial blood vessel A completely to its original shape and securely fix it onto the inner wall of the blood vessel. At this time the thorns 12a₁ stick into the inner wall of the blood vessel 9 and are embedded therein. After the artificial blood vessel A has been thus fixed, the balloon 23b of the balloon catheter 23 is deflated by drawing air through the opening 23c and the balloon catheter 23 is pulled out from the artificial blood vessel A by pulling the pipe 23a rearwardly. Then it is confirmed that the artificial blood vessel A has been fixed onto the inner wall of the blood vessel 9, and then the wire 3 is pulled out of the tube 2. As the front end of the wire 3 passes the rear edge of the side window 1 of the tube 2 as shown in FIG. 13, the loop portion 4a of the string 4 that has been caught by the wire 3 at the side window 1 is released from the wire 3. Under the condition, when the tube 2 is pulled out, the string 4 slips out of the front hooking means 13 of the artificial blood vessel A. The balloon catheter 23 and the tube 2 are then connected again by the fastener 24 and pulled out of the human body with only the artificial blood vessel A left at the desired position in the blood vessel 9. As mentioned above, in accordance with the invention, the artificial blood vessel A is implanted into the affected portion 26, and restored to its original shape thereby to effectively prevent occlusion of the affected portion 26 in the blood vessel 9. With the above-mentioned artificial blood vessel A and its collapsing method, the artificial blood vessel A can be collapsed with ease and accuracy. In other wards, as the intermediate wire ring 12 is collapsed into a wavy shape having the same phase as that of the front end wire ring $10_1$, to put it in an extreme way each of the points $41_3$~$44_3$ on the circumference corresponding to the dividing points $41_1$~$44_1$ forms a peak of a mountain or a bottom of a valley formed between two mountains by taking turns while the positions $51_3$~$54_3$ corresponding to midpoints $51_1$~$54_1$ between each adjacent two of the dividing points move neither frontward nor rearward at all. As the intermediate wire rings 12 are fixedly attached to the tubular cover 7 at the points $51_3$~$54_3$, the portions of the intermediate wire ring 12 which bent most when being folded are free of the tubular cover 7. This makes the intermediate wire ring 12 free from dragging resistance from the tubular cover, thereby to secure the free movement to be collapsed with ease. In addition, as the intermediate wire ring 12 is collapsed into a wavy shape as well as the front end wire ring $10_1$, the whole artificial blood vessel A can be folded into a small size and even through a relatively bulky artificial blood vessel A can be effectively transported to the affected portion 26 through a catheter 8. In addition, if the artificial blood vessel A is released at a target position in a blood vessel, the dividing points $41_1$~$44_1$ and the intermediate wire rings 12 are restored toward right-angled direction to the blood vessel together with the front end wire ring $10_1$, and the artificial blood vessel A does not close the inner space thereof. This certainly improves a rate of successful implantation.

In this embodiment, as the flexible braid members 10a are circumferentially arranged on the front and rear end wire rings $10_1$, $10_2$ of the artificial blood vessel A, the inner wall of a human organ can be prevented from being damaged by direct contact with the front and rear end wire rings $10_1$, $10_2$ in addition to the advantage that both ends of the implanted artificial blood vessel A can be sealed tightly to the inner wall of a human body, thereby to effectively prevent leakage of blood through the ends of the artificial blood vessel A.

In this embodiment as the thorns $12a_1$ project from the intermediate wire rings 12, they stick into the inner wall of a human organ to be embedded therein so that the whole artificial blood vessel A is fixed to the human organ. Therefore, after the artificial blood vessel A has been implanted in the human organ, the thorns $12a_1$ effectively prevent displacement of the artificial blood vessel A, which may cause the vessel A to be carried by blood flow downstream in the blood vessel.

In this embodiment, as the number of the dividing points is set four, it is possible to make effective use of the forceps 19. In other words, as described above, when whole of the artificial blood vessel A is picked by forceps 19 along the generatrices $l_5$, $l_6$ which pass through two points $41_1$, $43_1$ of the front end wire ring $10_1$ each of which has hooking means 13 and is arranged face to face and is inserted into the funneled tube 18, the points picked by forceps 19 are carried ahead from the enlarged inlet opening 18a to the tapered inner surface 18d of the funneled tube 18 and the dividing points $42_1$, $44_1$ each of which is not provided with the hooking means 13 gradually approach each other with the movement of following the dividing points $41_1$, $43_1$ restrained by abutting engagement with the tapered inner surface 18d of the funneled tube 18 which prevents to follow. Consequently the artificial blood vessel A is collapsed into a regular wavy shape with the points picked up by forceps 19 forming forwardly directed peaks and the midpoints forming the bottoms of forwardly directed valleys. The same is true with the intermediate wire rings 12 so that the intermediate wire rings 12 easily transform into a wavy shape having peaks and valleys with the points $51_3$, $52_3$, $53_3$, $54_3$ on the circumference thereof corresponding to the midpoints between two adjacent dividing points of the front end wire ring $10_1$ serving as fulcra, thereby to make the movement of being collapsed easy and accurate.

The serrate engaging member 19a provided on the picking surface of the forceps 19 makes it very easy to insert or withdraw the forceps 19, as the serrate engaging member 19a facing against the direction to be inserted is useful to transform the urging force applied to the forceps 19 into a propelling force to the artificial blood vessel A when the artificial blood vessel A is to be inserted, while the serrate engaging member 19a facing for the direction to be inserted makes it possible to withdraw the forceps 19 from the funneled tube 18 with the artificial blood vessel A in the funneled tube 18 left without dragging the artificial blood vessel A.

In addition, the device C for introducing the artificial blood vessel makes it extremely easy and smooth to introduce the artificial blood vessel A into the catheter 8. In other words, the reason why the device C is composed of the attachment 5 and the cartridge 6 each of which has a check valve 55, 68 is not only to prevent blood from flowing backward but also to provide a strong portion with the device C to be handled easily. Especially in this embodiment, the cap 66 is helically attached to the outer surface of the helical member 52a so as to joint the cartridge 6 and the attachment 5 liquid-tightly. Consequently, excessive bleeding while the cartridge 6 is pulled out of the attachment 5 can certainly be prevented as well as the front end of the straw member 64 of the cartridge 6 can be kept to make a smooth connection with the internal surface of the open end 8a of the catheter 8. In addition, as the above-mentioned cartridge 6 can be attached to the attachment 5 with accuracy as long as the length of the straw member 64 projecting from the guide pipe 65 remains the same, the cartridge 6 can easily be applied to the artificial blood vessel A in variety of length by changing the length of the guide pipe 65 or of the straw member 64.

This invention is not limited to the above-mentioned embodiments. For example, if the vessel of the affected portion where the artificial blood vessel is to be implanted is different from the above mentioned and bifurcated, it is effective to use the artificial blood vessel D shown in FIG. 34. The artificial blood vessel D is to be implanted, for example, into the blood vessel of the groin. The artificial blood vessel D has fundamentally the same arrangement as that of the above-mentioned embodiment. This artificial blood vessel D, however, is for fitting the shape of the blood vessel into which the artificial blood vessel D is implanted characterized by that a single front end wire ring $110_1$ is arranged face to parallely arranged two rear end wire rings $110_2$ each of whose diameter is smaller than that of the front end wire rings $110_1$, and a bifurcated tubular cover 107 connects the front end wire rings $110_1$ and two rear end wire rings $110_2$. And intermediate wire rings $112_1$ each of whose diameter is generally the same as that of the front end wire rings $110_1$ are arranged at the position whose diameter is the same as that of the front end wire ring $110_1$, while intermediate wire rings $112_2$ each of whose diameter is generally the same as that the rear end wire ring $110_2$ are arranged at the position whose diameter is the same as that of the rear end wire ring $110_2$. Each of the intermediate wire ring $112_1$, $112_2$ is fixed to the cover 107 at a plurality of seperate positions on the circumference thereof as the same as in the former embodiment.

Figure 35:
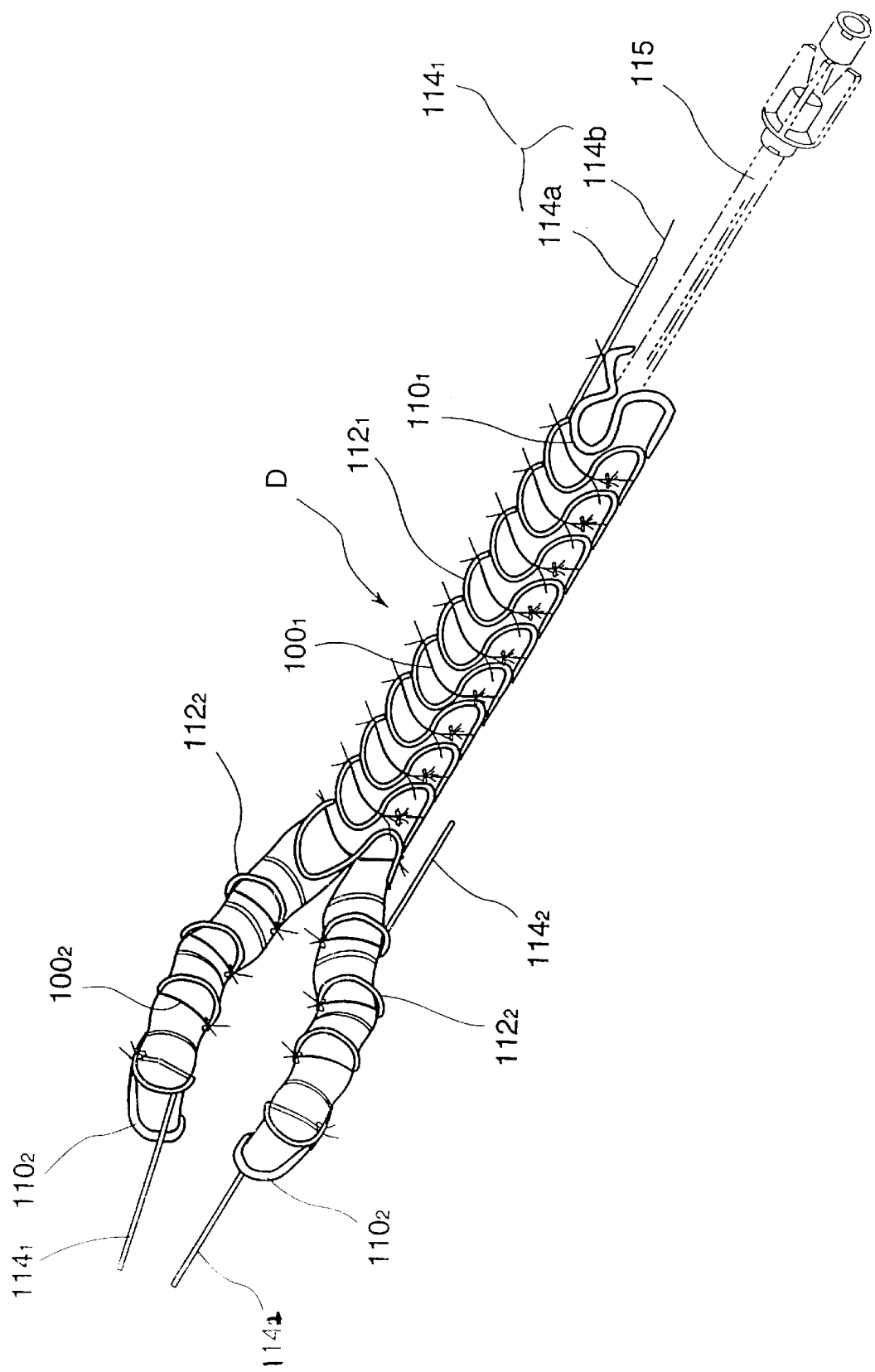
FIG. 35 is a perspective view showing the artificial blood vessel which has previously been folded by means of a sting.
Figure 36:
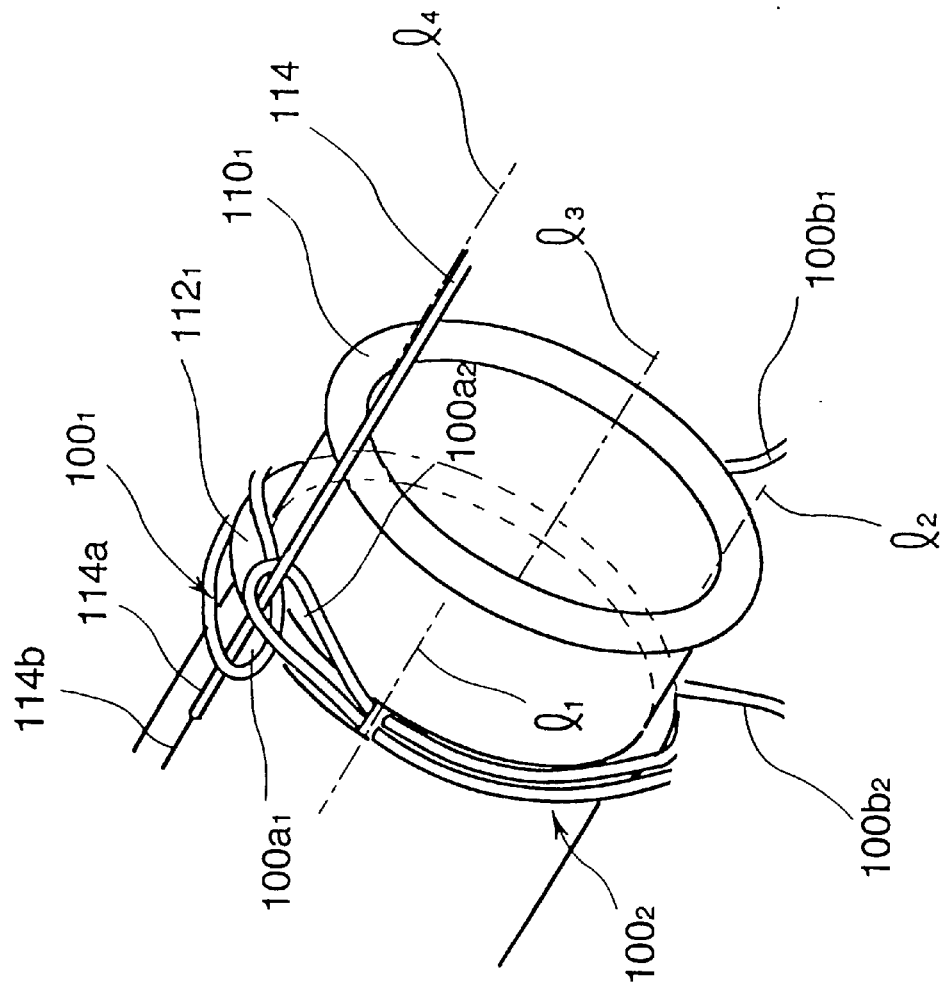
FIG. 36 is a perspective view showing a procedure of folding the artificial blood vessel by means of a string.
Figure 37:
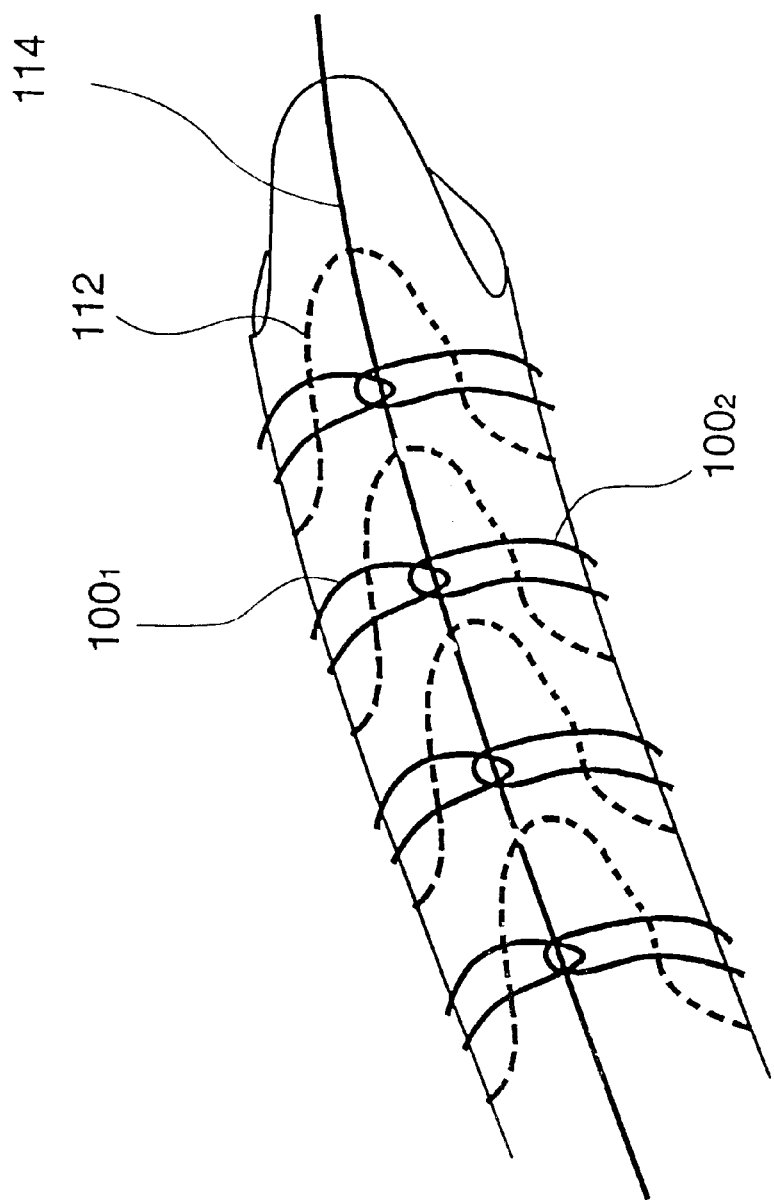
FIG. 37 is a perspective view showing the artificial blood vessel around which a string is wound.

On the other hand, the artificial blood vessel D which has been previously collapsed into small is inserted into the catheter and transported to a target organ. The method of collapsing the artificial blood vessel D will be described. A pair of strings $100_1$, $100_2$ are attached to each of the wire rings $110_1$, $112_1$, $112_2$, $110_2$ of the artificial blood vessel D at the points where each of the wire rings $110_1$, $112_1$, $112_2$, $110_2$ is fixed to the tubular cover 107. The intermediate wire ring $112_1$ is represented for concrete explanation. First, the string $100_1$ is kept folded at the center thereof hooked by a needle for operation. In this state the string $100_1$ is wound around the intermediate wire ring $112_1$ clockwise by making use of the needle until it reaches the backward of the intermediate wire ring $112_1$ as shown in FIG. 36, and then sewed up at a plurality of separate positions with the needle. The positions at which the string $100_1$ is sewed up fall on the generatrices corresponding to the midpoints between two adjacent dividing points of the front end wire ring $110_1$, and in this embodiment the string $100_1$ is sewed up at two positions. The string $100_1$ is preferably sewed to the protective film (like the protective film 12b in FIG. 2) which covers the surface of the intermediate wire ring $112_1$, but may be sewed to the tubular cover 107 as long as the artificial blood vessel D is kept liquidtight. Likewise another string $100_2$ is wound around the intermediate wire ring $112_1$ counterclockwise and then sewed up at positions symmetric to the string $100_1$. Next, insert a rod 115 into the artificial blood vessel D for helping the artificial blood vessel D be collapsed. Loop portions $100a_1$, $100a_2$ each formed at each of the tip of a pair of strings $100_1$, $100_2$ are overlapped, into which a retaining rod 114 is inserted and then end portions $100b_1$, $100b_2$ of the strings $100_1$, $100_2$ are tied together. The artificial blood vessel D is helped to be collapsed by a finger or the like, if necessary. The intermediate wire ring $112_1$ is gathered so that the points corresponding to the midpoints between two adjacent dividing points approach the rod 115 as a string is passed through each of the points, thereby to be collapsed into a wavy shape with the dividing points between the points at which the string is sewed up forming the bottoms of valley and the peaks in turn as shown in FIG. 37. This operation is done to each of the wire rings $110_1$, $112_1$, $112_2$, $110_2$. The consequence is shown in FIG. 35. As it is clear in FIG. 35, there are two retaining rods in this embodiment. The longer retaining rod $114_1$ retains the area from the front end wire ring $110_1$ to one of the rear end wire ring $110_2$ to be collapsed, and the shorter retaining rod $114_2$ retains the area from the intermediate wire ring $112_2$ located at the divergence to the other rear end wire ring $110_2$ to be collapsed.

The retaining rod 114 comprises a tube 114a and a wire 114b which is inserted into the tube 114a. The tube 114a is drawn out and only the wire 114b is left after the artificial blood vessel D is kept in a collapsed condition. Although the wire 114b is smaller in diameter than that of the tube 114a, the wire 114b can effectively bind the strings. In addition, the wire 114b can be flexibly transformed into a bending portion of the transporting course as softer than the tube 114a. In other words, the tube 114a is temporarily used to make it easy to fold the artificial blood vessel D and is drawn out together with the rod 115 after the artificial blood vessel D is collapsed into a small size.

Figure 38:
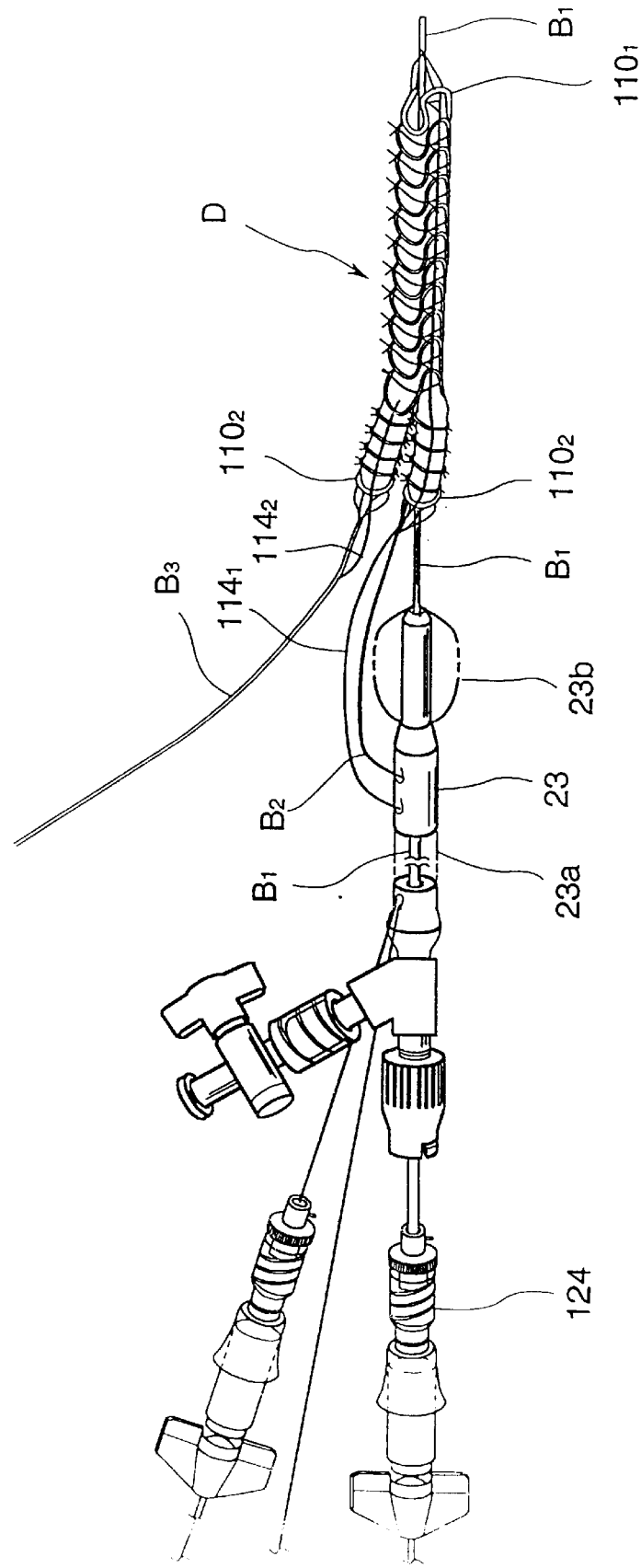
FIG. 38 is a perspective view showing a device for transporting the artificial blood vessel.
Figure 39:
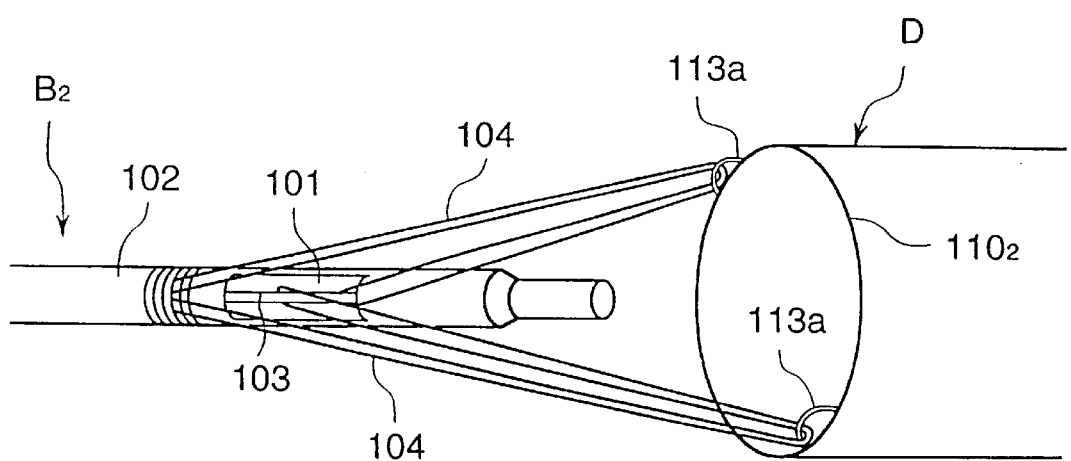
FIG. 39 is a perspective view showing a device for transporting the artificial blood vessel to pull the rear end wire ring of the artificial blood vessel shown in FIG. 38.

Thus folded artificial blood vessel 2 is transported to and implanted into a target position, namely, a bifurcated affected portion by means of the method in accordance with the embodiment. In this embodiment, three devices B1, B2, B3 for transporting the artificial blood vessel are used as shown in FIG. 38. The first device B1 for transporting the artificial blood vessel is the same as that used in the former embodiment, namely, the one which is inserted into the tube 23a of the balloon catheter 23 with the front tip passed through the artificial blood vessel D and projecting to reach the most front position and keeps a front end wire ring $110_1$ with a string hooking a front hooking means 113 of the front end wire ring $110_1$. The second device B2 for transporting the artificial blood vessel is inserted into an elongated hole formed on the thickness of the tube 23a of the balloon catheter 23 with the front tip thereof drawn outside in front of the balloon 23b and keeps a rear end wire ring $110_2$ with a string 104 hooking a rear hooking means 113a of the rear end wire ring $110_2$. The third device B3 for transporting the artificial blood vessel is arranged parallel to the balloon catheter 23 and keeps another rear end wire ring $110_2$ with a string 104 hooking a rear hooking means 113a of the rear end wire ring $110_2$. The tube 102 of the device B3 for transporting the artificial blood vessel is of especially softer material than that of other devices for transporting the artificial blood vessel. The tube 102 of the device B3 for transporting the artificial blood vessel is provided with an elongated hole formed on the thickness thereof as well as the former embodiment, into which the retaining rod $114_2$ is inserted and passed through. Each of these devices B1~B2 for transporting the artificial blood vessel is inserted into a body through the cartridge 6 and the attachment 5 of the former embodiment. As the devices B1, B2 are attached to the balloon catheter 23, they can pass liquid-tightly through the cartridge 6 and the attachment 5 with the check valve 68 of the cartridge 6 and the check valve 55 of the attachment 5 pushed to open a little. However, if the device B3 is inserted into the check valves 68, 55, opening is formed between the device B3 and each of the check valves 68, 55, thereby causing to decline liquidtightness. Then for using the device B3, another hole (not shown in Figures) corresponding to the device B3 should be provided at the position deviating from the center of each check valves 68, 55.

Figure 40:
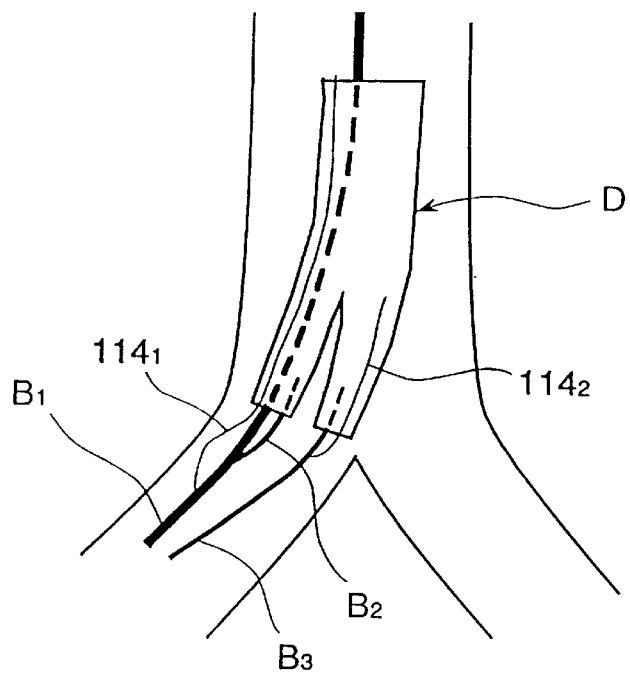
FIG. 40 shows the principle how the artificial blood vessel of the embodiment is used.
Figure 41:
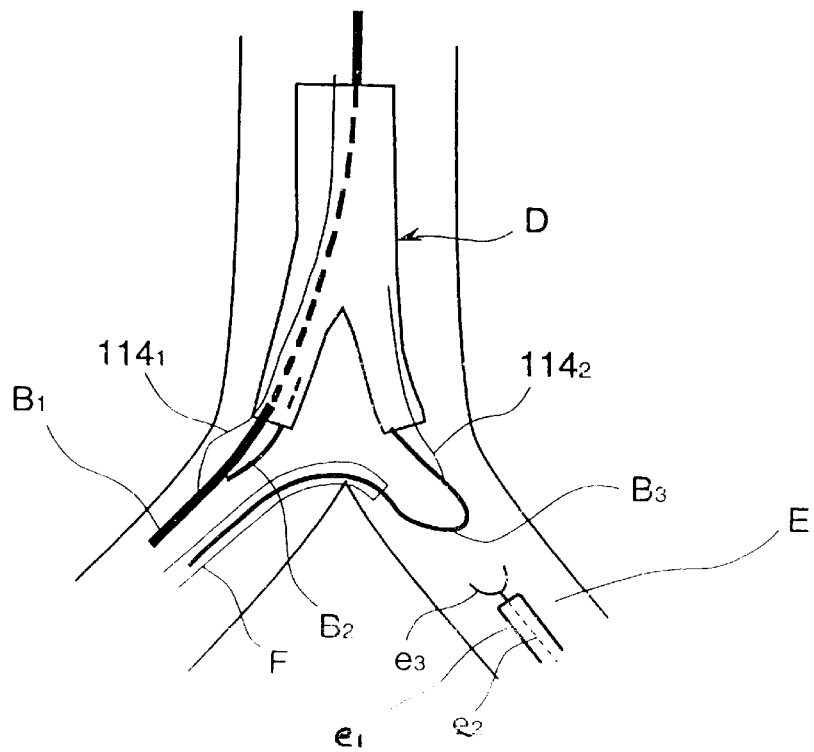
FIG. 41 shows the principle how the artificial blood vessel of the embodiment is used.
Figure 42:
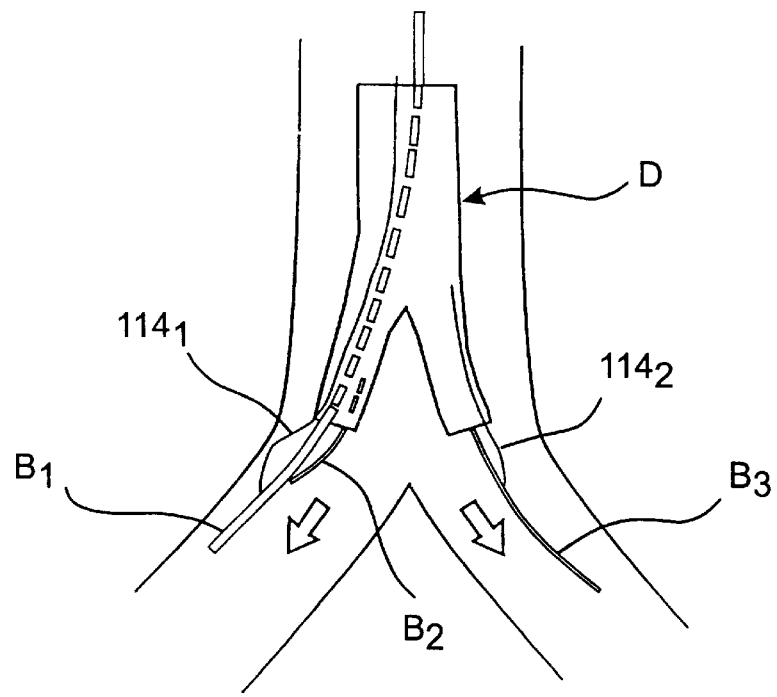
FIG. 42 shows the principle how the artificial blood vessel of the embodiment is used.
Figure 43:
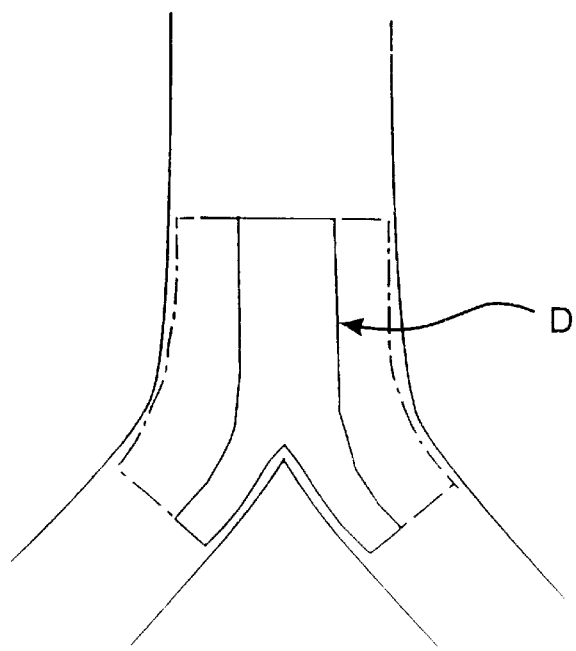
FIG. 43 shows the principle how the artificial blood vessel of the embodiment is used.

Next, the process of implanting the artificial blood vessel D will now be described below. First, the device B1 is pushed by making use of the balloon catheter 23 then like the former embodiment the balloon catheter 23 is inserted into the catheter through the blood vessel of the groin. Next, the artificial blood vessel D is, as shown in FIG. 40, released at the target position, in particular, the bifurcated affected portion. The artificial blood vessel D is kept in a condition of being collapsed by the retaining rod $114_1$, $114_2$. The artificial blood vessel D is located at a trunk of the blood vessel a little passing the affected portion by adjusting the position frontward of rearward with making use of the devices B1, B2. Then the device B3 is pushed into a body through the catheter 8. As the device B3 is made of soft material, it can be slacked off toward a predetermined direction near the affected portion if a J-shaped guide pipe F or the like is appropriately used as shown in FIG. 41. Under the condition, a catcher E for catching the device for transporting the artificial blood vessel is introduced near the affected portion through the catheter from another bifurcated portion of the groin. The catcher E comprises a tube e1, a wire e2 inserted into the tube e1, and a U-shaped hook e3 formed at the front tip of the wire e2 and which is projecting from the tube e1, and is so constructed that the wire e2 projects out of the tube e1, the hook e3 opens at the position where the wire e2 projects and that the hook e3 closes by the tube e1 at the position where the wire e2 is inserted into the tube e1. The device B3 which has previously slacked off is caught by making use of the catcher E and then drawn out of the body through another portion of the bifurcated groin. After all of the devices B1, B2, B3 are drawn out from right and left portion of the groin as shown in FIG. 42, pulling force toward the direction shown by the arrow in the figure is applied to the rear end wire rings $110_2$ of the artificial blood vessel D by making use of the devices B2 and B3. Then each of the rear end wire rings $110_2$ of the Y-shaped artificial blood vessel D is drawn from a trunk of the blood vessel into each of the bifurcated branches of the blood vessel. After the artificial blood vessel D is arranged along the bifurcated blood vessels as shown in FIG. 43, the wire of the retaining rod $114_1$, $114_2$ each attached to the device B1, B3 respectively for retaining the artificial blood vessel D in a collapsed condition is pulled out, thereby to release the artificial blood vessel D from being folded in a small size. Then the artificial blood vessel D is restored as shown by imaginary lines in FIG. 43 and implanted into the internal wall of the affected portion, namely, the bifurcated blood vessel. Finally, each wire of the devices B1, B2, B3 is pulled out, thereby to release the front and rear hooking means from being kept, which makes it possible to draw the devices B1, B2, B3 out of the body.

In accordance with the method of implanting the artificial blood vessel D, it is possible to implant an artificial blood vessel into an affected portion with non-operational method even though the affected portion falls on the bifurcated blood vessel. The artificial blood vessel D is not always necessary to be folded into a small size beforehand by means of strings $100_1$, $100_2$, it may sometimes be implanted through a catheter 8 just being collapsed into a small size as well as the simple cylinder-shaped artificial blood vessel A as shown in FIG. 1. The rear hooking means 113a for pulling the rear end wire ring $110_2$ and the second device B2 for transporting the artificial blood vessel may be applied to the rear end wire ring $10_2$ of the artificial blood vessel A shown in FIG. 1. This makes it possible to move the artificial blood vessel A by adjusting the position of the artificial blood vessel A rearward or forward, after the artificial blood vessel A is released from the catheter 8 at the affected portion 26, thereby to implant the artificial blood vessel A with accuracy.

The artificial blood vessels may be restored in a cartridge by pulling out the retaining rod. It is effective that the artificial blood vessels partially comprise a string of gold which can be X-rayed so as to monitor the implanted condition of the artificial blood vessel.

Figure 44:
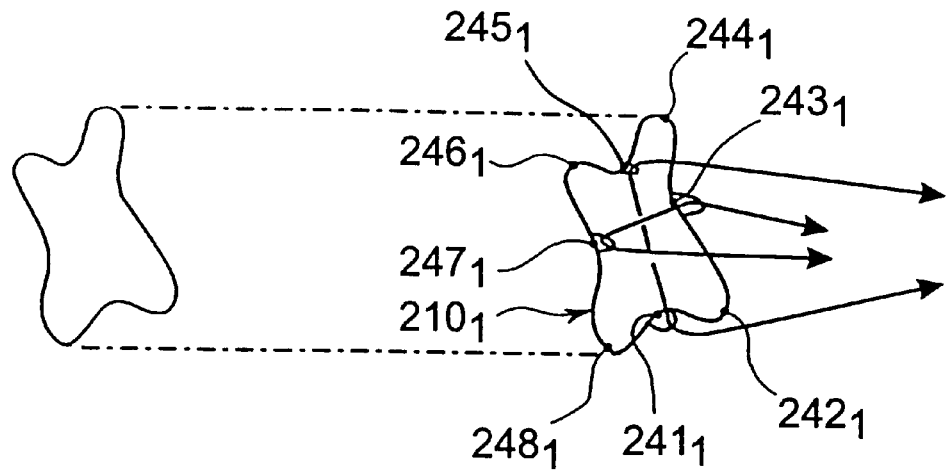
FIG. 44 is a diagram showing an artificial blood vessel in accordance with a different embodiment of the invention.
Figure 45:
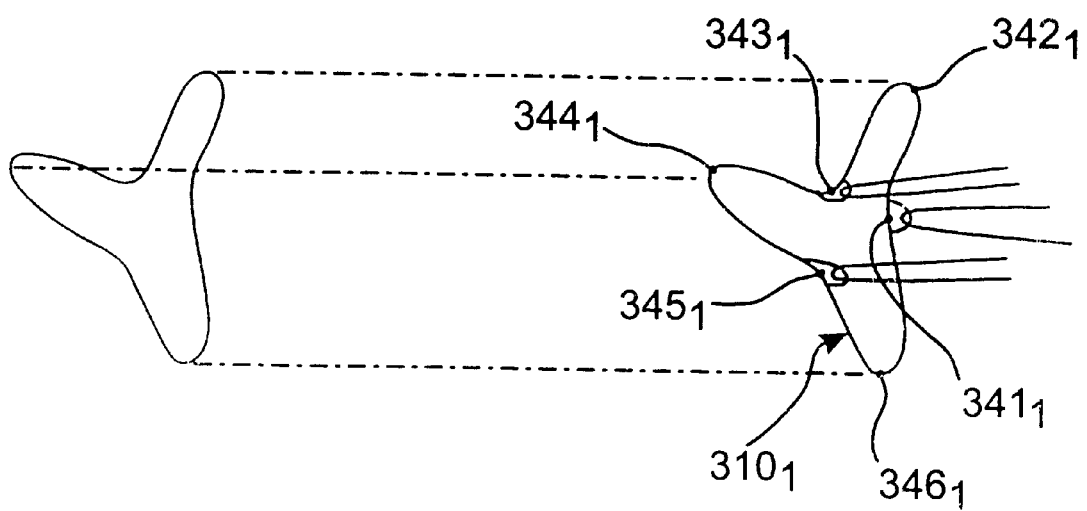
FIG. 45 is a diagram showing an artificial blood vessel in accordance with a further different embodiment of the invention.

The invention is not limited to the above-mentioned embodiments. For example, in the above embodiment, the front end wire ring has its circumference divided into four equal arcs to set four dividing points. As shown in FIG. 44, a front end wire ring $210_1$ may have its circumference divided into eight arcs to set eight dividing points $241_1$, $242_1$, $243_1$, $244_1$, $245_1$, $246_1$, $247_1$, $248_1$, four of which $241_1$, $243_1$, $245_1$, $247_1$ are provided with a hooking means and other four $242_1$, $244_1$, $246_1$, $248_1$ are not provided with a hooking means. As shown in FIG. 45, a front end wire ring $310_1$ may have its circumference divided into six arcs to set sic dividing points $341_1$, $342_1$, $343_1$, $344_1$, $345_1$, $346_1$, three of which $341_1$, $343_1$, $345_1$ are provided with a hooking means and other three $342_1$, $344_1$, $346_1$ are not provided with a hooking means.

Figure 46:
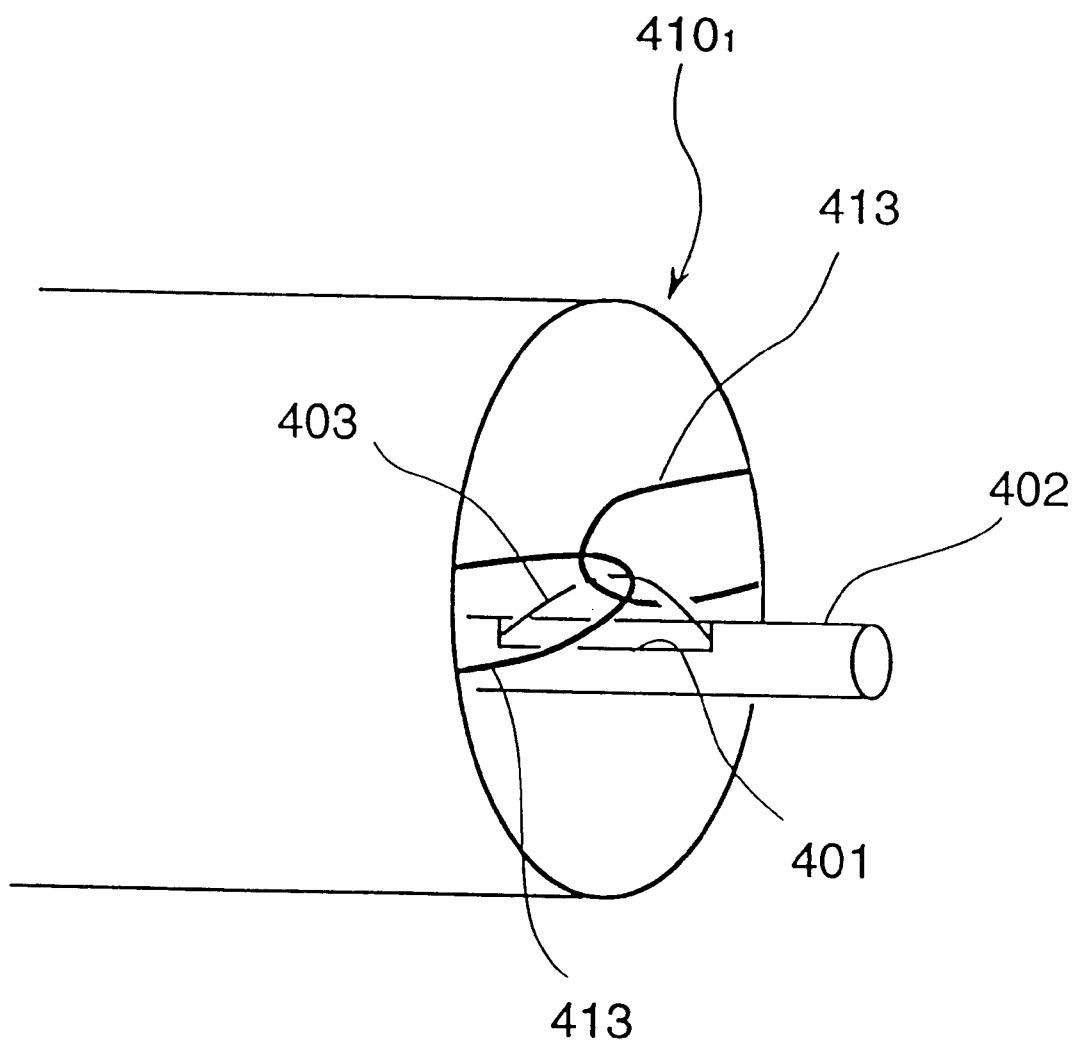
FIG. 46 is a perspective view showing a device for transporting the artificial blood vessel in accordance with a further different embodiment of the invention.

In the above embodiment, the device for transporting the artificial blood vessel is provided with a pair of strings with loop portions. The strings need not always be provided in a pair. However, the strings provided in a pair are effective because a balanced pulling force can be applied to the artificial blood vessel. The loop portions may be twisted as a whole. A device for transporting the artificial blood vessel comprising only a tube and a wire and which is not provided with strings may be used. For example, as shown in FIG. 46, front hooking means 413 formed on the front end wire ring $410_1$ are made a little longer, each of loop portions of the front hooking means 413 are overlapped, and a wire 403 pulled out of a side window 401 of a tube 402 is passed though and inserted into the overlapped loop portion so as to keep the artificial blood vessel. If there is no trouble to form holes directly on the tubular cover, it is also possible to keep the artificial blood vessel by means of a wire and a tube with making use of the holes as a hooking means.

Therefore, such a device for transporting the artificial blood vessel can be used to a patch to close a hole formed on a heart or the like.

Figure 34:
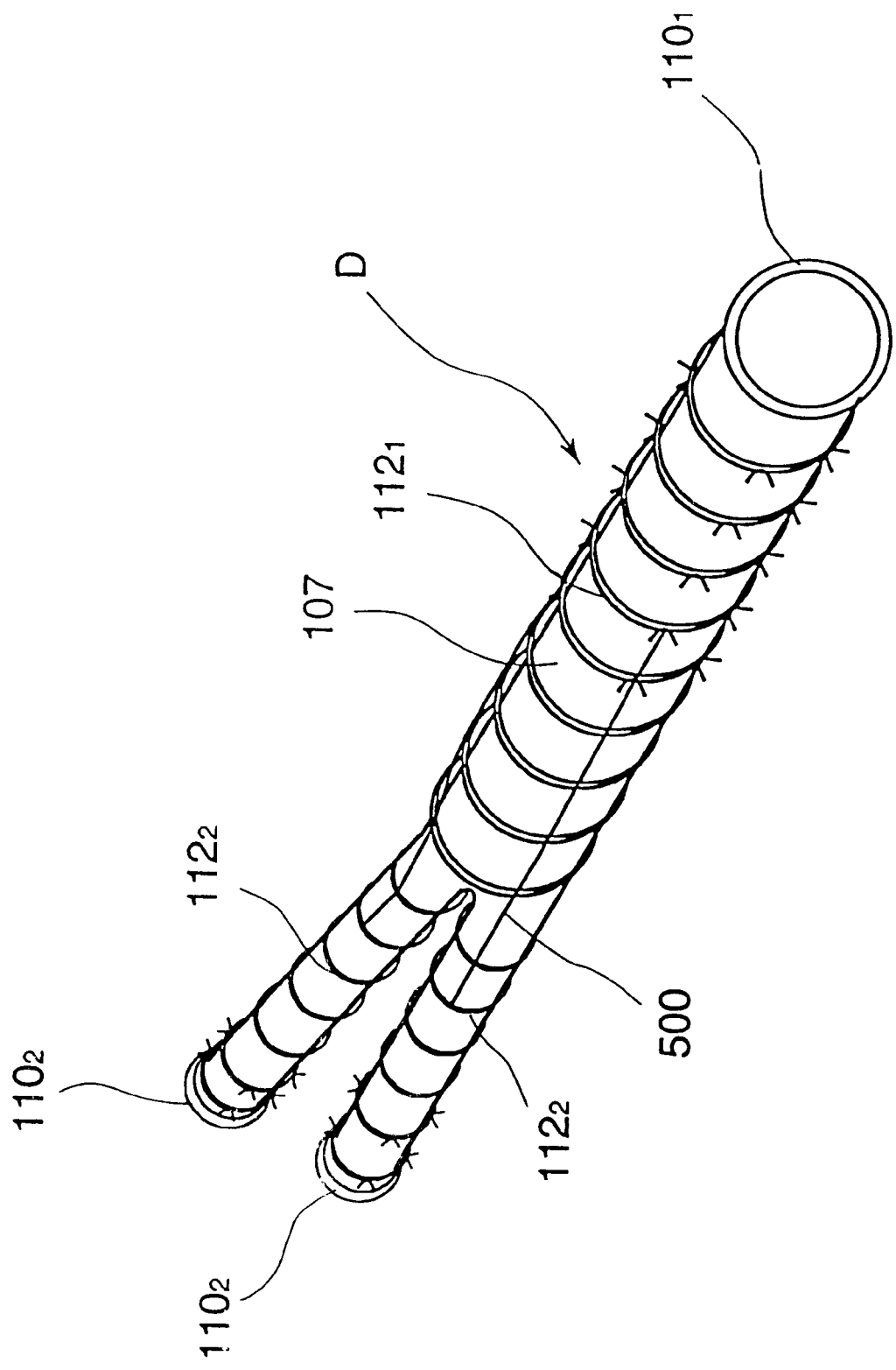
FIG. 34 is a perspective view of the artificial blood vessel use in another embodiment of the invention.

The intermediate wire rings 112 may be bridged by a supporting rod 500 as shown in FIG. 34. The supporting rod 500 attached to the intermediate wire rings 112 improves the tubular shape of the artificial blood vessel D in the strength and the construction. The supporting rod 500 may be attached to the front or rear end wire ring $110_1$, $110_2$. If the supporting rod 500 is fixed to the same position on the circumference of the front or rear end wire ring $110_1$, $110_2$ as that of the intermediate wire ring 112, it does not prevent the artificial blood vessel D from being folded.

Figure 47:
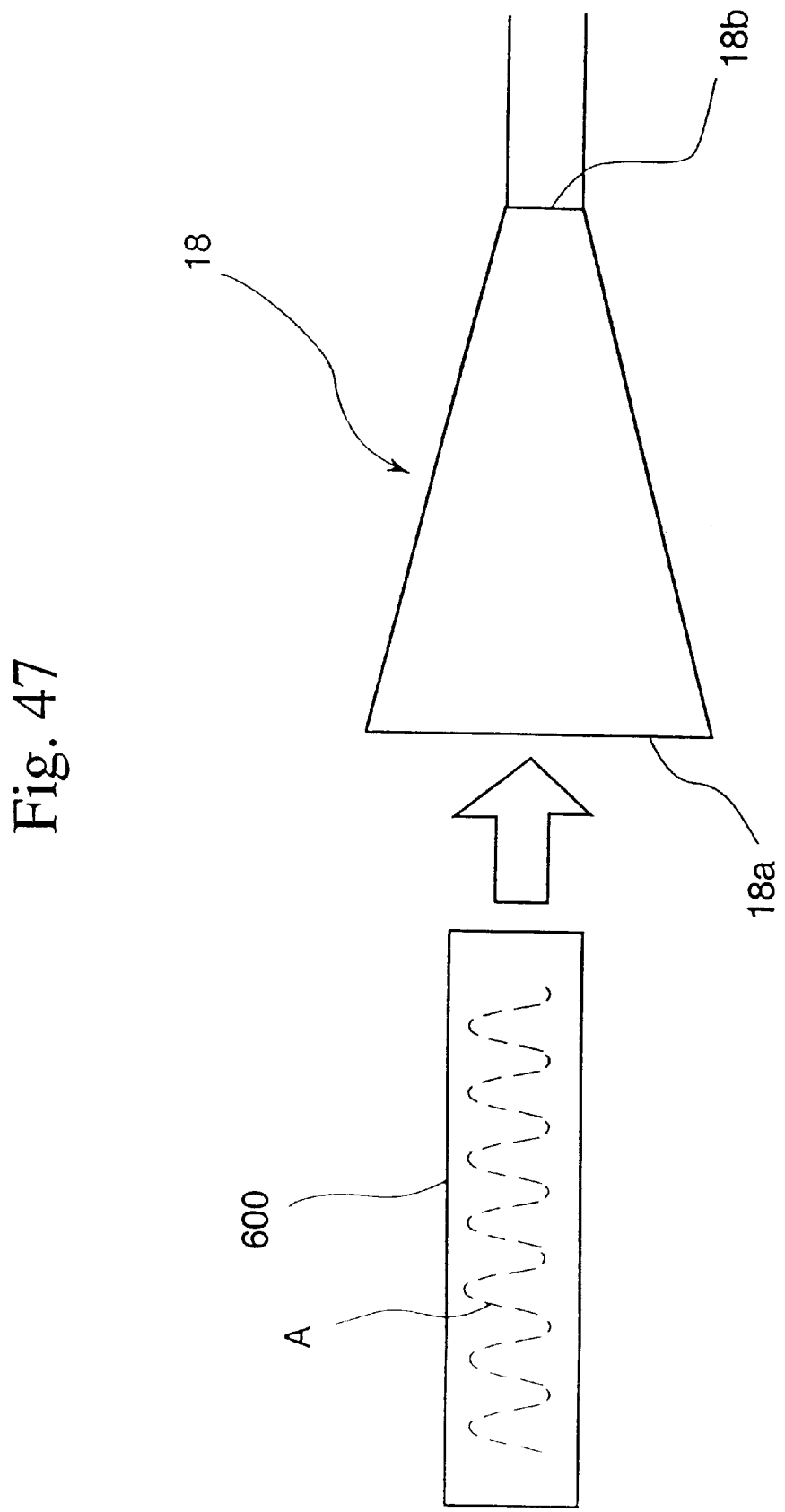
FIG. 47 shows a method of collapsing the artificial blood vessel in accordance with further different embodiment of the invention.

In order to collapse the artificial blood vessel A into a small size by inserting it into a funneled tube 18 from a big portion 18a toward a small portion 18b the artificial blood vessel A may be previously contained in a pipe member 600 having a diameter bigger than that of the small portion 18b of the funneled tube 18 and smaller than that of the big portion 18a of the funneled tube 18 as shown in FIG. 47. Just inserting the pipe member 600 into the funneled tube 18 so as to make abutting engagement with the inner surface of the funneled tube 18 and pulling out the artificial blood vessel A from the side of the front end wire ring enables the artificial blood vessel A to be collapsed into a smaller size so as to be inserted into the small portion 18a of the funneled tube 18 and a catheter.

Figure 48:
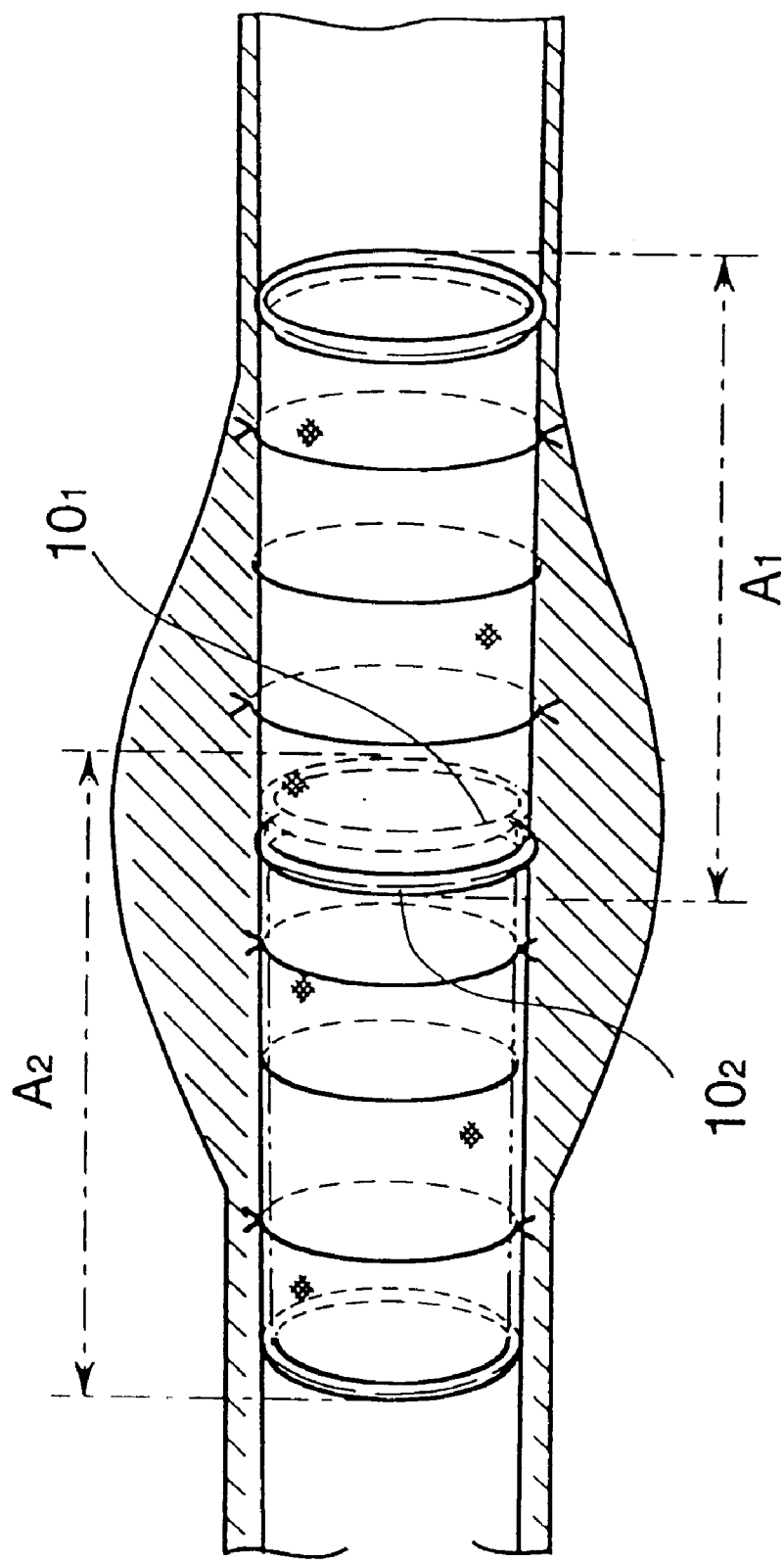
FIG. 48 shows a method of using the artificial blood vessel in accordance with further different embodiment of the invention.

In addition, as shown in FIG. 48, two the artificial blood vessel A1, A2 may be prepared and the front end wire ring $10_1$ of the artificial blood vessel A2 which is to be inserted later locates in front of the rear end wire ring $10_2$ of the artificial blood vessel A2 which is to be inserted former so that the artificial blood vessel A1 is connected to the artificial blood vessel A2 with each other partially overlapped at the adjacent position. Then the whole length of the connected the artificial blood vessel can be changed relatively freely by adjusting the length of the overlapped portion. This makes it possible that the artificial blood vessel A1, A2 having the same standard can be tailored for the affected portion 28 whose length or shape varies a little. It is especially preferable that the artificial blood vessel A2 arranged downstream has a diameter which is smaller than that of the artificial blood vessel A1 arranged upstream and that the artificial blood vessel A2 arranged downstream is partially inserted into the artificial blood vessel A1 arranged upstream. Thus arranged the artificial blood vessel A1, A2 are connected smoothly as well as they can be implanted satisfactory so as to fit the shape of the blood vessel into which the artificial blood vessels A1, A2 are to be implanted because usually blood vessels are gradually smaller in diameter from upstream to downstream. Of course, even if artificial blood vessels have the same diameter, it is not difficult to partially insert one of the artificial blood vessels into another just by transforming one of the artificial blood vessels.

Next, when an artificial blood vessel is to be implanted into an affected portion whose shape is bifurcated as described above, a more preferable mode of embodying the invention will now be described in detail with reference to FIGS. 49 through 53.

Figure 49:
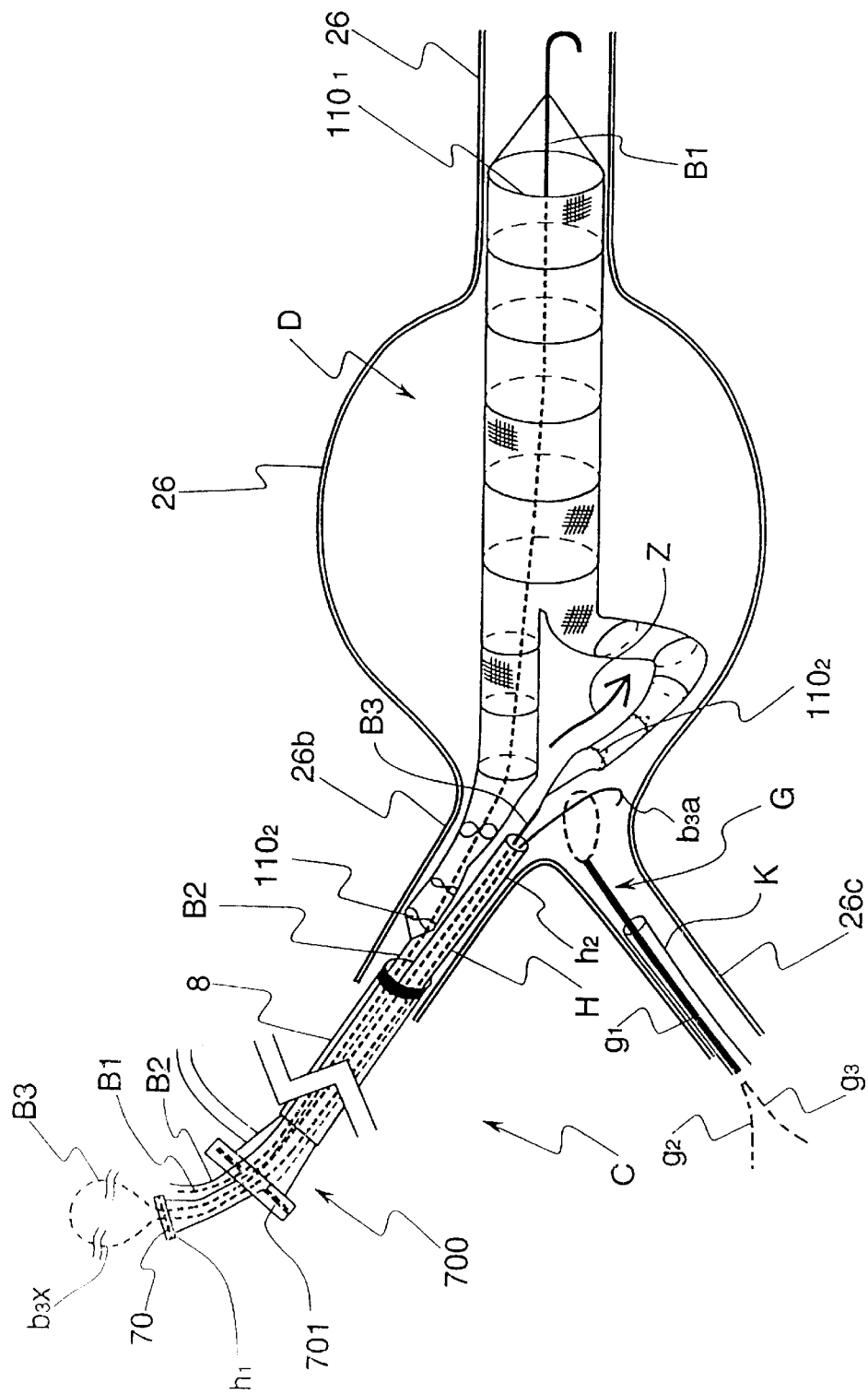
FIG. 49 is a view showing a condition of a method of using in accordance with further different embodiment of the invention.

The artificial blood vessel D shown in FIG. 49 is fundamentally the same in arrangement as that of FIG. 34. Unlike the artificial blood vessel D which is inserted into a catheter 8 with the whole artificial blood vessel 2 folded into a small size as shown in FIG. 35, in this embodiment the artificial blood vessel D is inserted into a catheter 8 with only a bifurcated portion of small diameter folded into a small size as shown in FIG. 49. The reason is to prevent the thorn body 12$a_1$ from unnecessarily hurt the tissues of the body to be implanted. This is done by releasing at least a main portion of the artificial blood vessel D at a predetermined position from the first so as to avoid adjusting the position of the main body after released. The artificial blood vessel D is folded into a small size by means of the strings 100$_1$, 110$_2$ and the retaining rod 114 like the embodiment explained with reference to FIGS. 36 and 37. Then as shown in FIG. 49, the artificial blood vessel D is transported to a bifurcated affected portion as a target position by means of the above-mentioned three devices B1, B2 and B3 for transporting the artificial blood vessel (see FIG. 38). Unlike the above-mentioned embodiment, no balloon catheter is attached to the first device B1 for transporting the artificial blood vessel in this embodiment, however, it is a matter of course that a balloon catheter may be attached if necessary. In this case, the balloon catheter is not necessarily inserted into a body together with the artificial blood vessel D, but can be inserted into a body after the artificial blood vessel D is transported to a target organ in the body.

As shown in FIG. 49, the first device B1 for transporting the artificial blood vessel holds the front end wire ring 110$_1$ with the front end thereof passing through the artificial blood vessel D and protruding toward the forefront. The second device B2 for transporting the artificial blood vessel holds one of the rear end wire rings 110$_2$ with the front end thereof locating rear of the artificial blood vessel 12. The third device B3 for transporting the artificial blood vessel holds the other rear end wire ring 110$_2$ with the front end thereof locating rear of the artificial blood vessel D. Like the embodiment shown in FIG. 38, retaining rods 114$_1$ and 114$_2$ for keeping the artificial blood vessel D in a collapsed condition are attached, although not shown in FIG. 49, to the second and the third devices B2 and B3 for transporting the artificial blood vessel. Especially the third device B3 for transporting the artificial blood vessel used in this embodiment is made of a material more flexible than that the other devices B1 and B2 are made of. In addition, at least the length corresponding to a distance from a groin of a thigh to the affected portion of the base end B3$a$ of the third device B3 for transporting the artificial blood vessel is made of a guide member b3$x$ such as a helical spring which is not only flexible but also having a characteristic that a force can be so transmitted to the whole part thereof by manipulating one part thereof that the whole device B3 can be freely rotated, inserted or pulled. The base end b3$a$ is bent sideward along the length thereof, which makes it possible to change the position of the base end b3$a$ relatively big by manipulating the guide member b3$x$ of the device B3.

Figure 51:
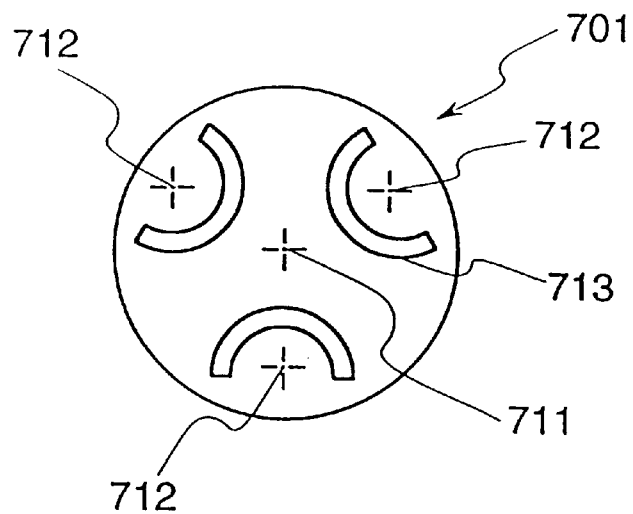
FIG. 51 is a view showing a valve used for a sheath of the embodiment.
Figure 52:
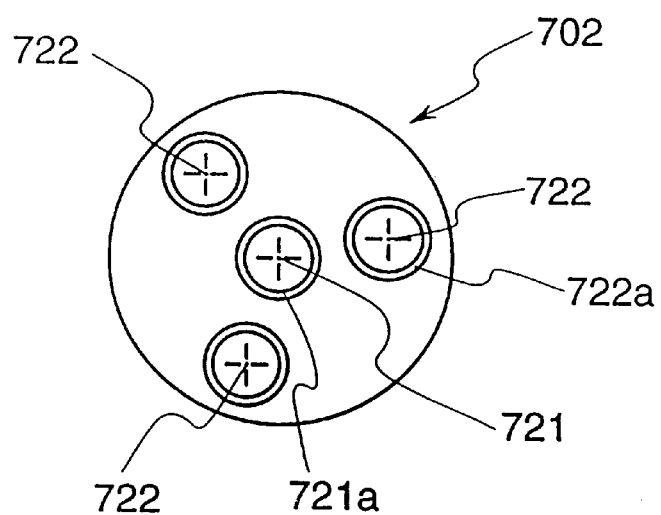
FIG. 52 is a view showing other valve which can be utilized instead of the valve shown in FIG. 51.
Figure 53:
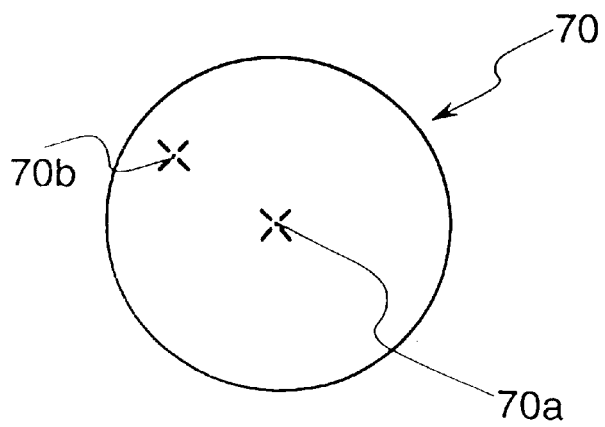
FIG. 53 is a view showing a valve used for a guide pipe of the embodiment.
Figure 54:
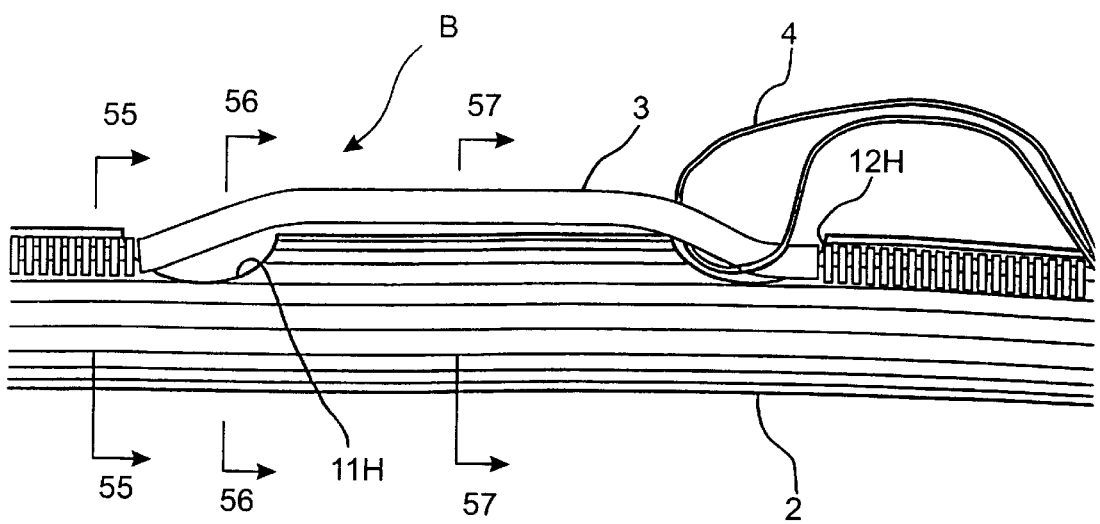
FIG. 54 is a view showing a modification of the device for transporting an artificial blood vessel.
Figure 55:
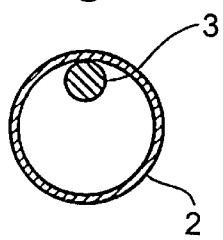
FIG. 55 is a cross-sectional view taken along the line X1—X1 of FIG. 54.
Figure 56:
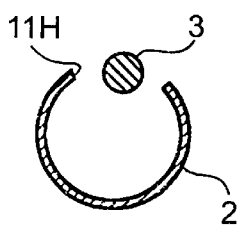
FIG. 56 is a cross-sectional view taken along the line Y1—Y1 of FIG. 54.
Figure 57:
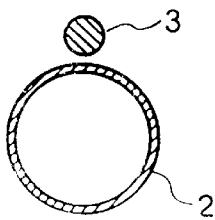
FIG. 57 is a cross-sectional view taken along the line Z1—Z1 of FIG. 54.
Figure 58:
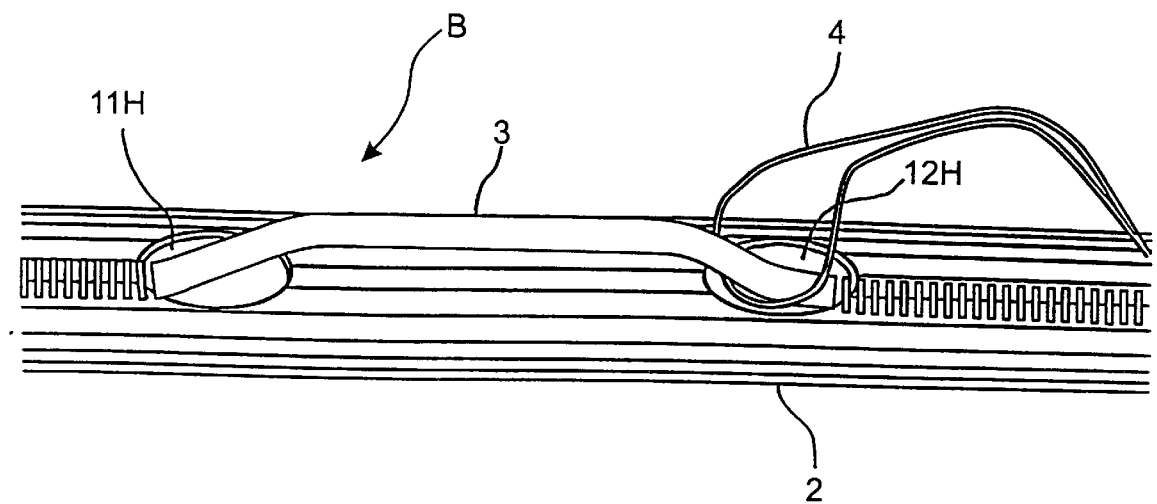
FIG. 58 is a view of the device for transporting the artificial blood vessel shown in FIG. 55 viewed from a different angle.
Figure 60:
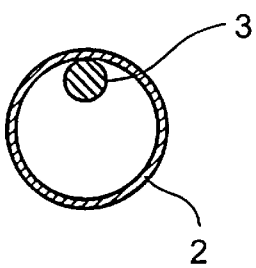
FIG. 60 is a cross-sectional view taken along the line X2—X2 of FIG. 59.
Figure 61:
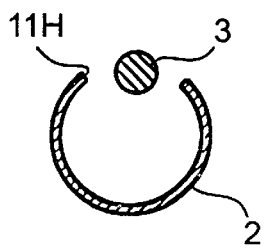
FIG. 61 is a cross-sectional view taken along the line Y2—Y2 of FIG. 59.
Figure 62:
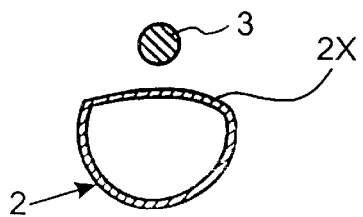
FIG. 62 is a cross-sectional view taken along the line Z2—Z2 of FIG. 59.
Figure 63:
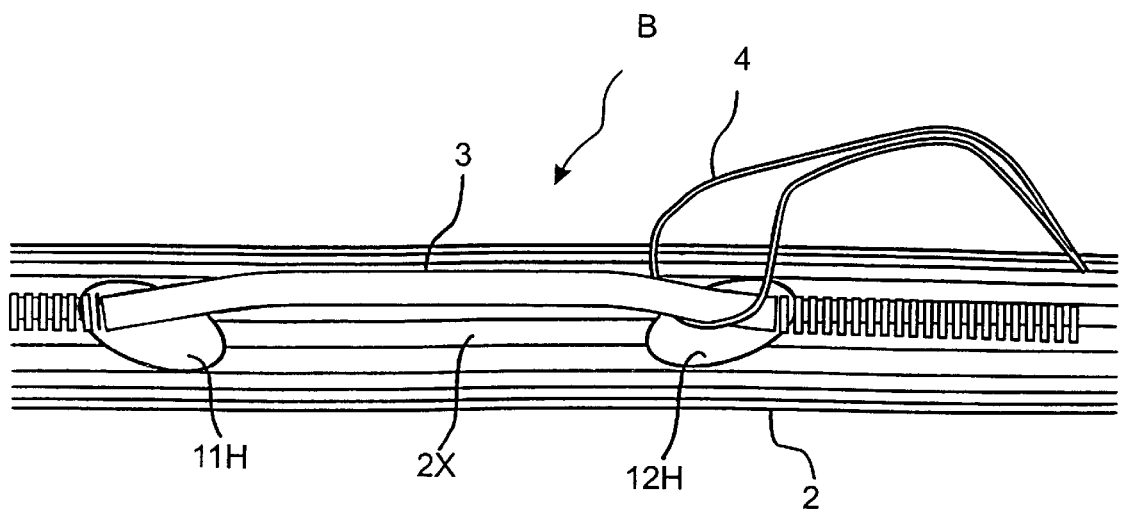
FIG. 63 is a view of the device for transporting an artificial blood vessel shown in FIG. 59 viewed from a different angle.

These devices B1, B2 and B3 are inserted into a catheter 8 through the cartridge 6 and the attachment 5 shown in FIG. 28. As mentioned above, since the devices B1 and B2 are not attached to a balloon catheter, the devices B1 and B2 are bundled together with the device B3 and inserted into the cartridge 6 with the valve 68 pushed to open. As a result of this, when the cartridge 6 is attached to the attachment as shown in FIG. 28, bleeding is likely to occur from the portion through which the devices B1, B2 and B3 are inserted. Then in this embodiment a sheath 700 to prevent leakage is provided beforehand as shown in FIG. 49 at the rear end of the cartridge 6. After the devices B1, B2 and B3 are inserted into the cartridge 6 together with the artificial blood vessel A, the sheath 700 is connected to the cartridge 6 with the valve 68 pushed to open. In FIG. 60 the cartridge 6 and the attachment 5 provided between the sheath 700 and the catheter 8 are omitted. The sheath 700 has fundamentally the same arrangement as that of the catheter 8 and is provided with a valve 701 at the rear end thereof. At the center of the valve 701 provided is a hole 711 which can be pushed to open against the elasticity of the valve 701 as shown in FIG. 51. The valve 701 is also provided with other three holes 712 each of which locates radially and equally distant from the center of the valve 701 and the distance between each adjacent hole 712 is the same. Between the hole 711 and each of the holes 712 provided is thick embankment 713 so as not to be easily connected through both of the holes 711 and 712 each other because of breakage. In this embodiment the first device B1 is inserted into and passed through the hole 711 and each of the second and third devices B2 and B3 is inserted into and passed trough two of the three holes 712 respectively. Instead of the valve 701, a valve 702 as shown in FIG. 52 may be used. The valve 702 has holes 721 and 722 at the positions corresponding to the holes 711 and 712 of FIG. 51. On the circumference of each hole 721 and 722 provided are annular projecting portions 721$a$ and 722$a$ whose inside is dent to make thin. Thus arranged valve is effective for preventing breakage between the hole 721 and the holes 722. The device B3 is inserted into and passed through the catheter 8 through a guide pipe H as shown in FIG. 49. The guide pipe H is so arranged that the base end h1 located out of the sheath 700 and the front end h2 passes through the sheath 700 and a catheter 8 and then located near a bifurcated affected portion. At the base end h1 of the guide pipe H provided is a valve 70 as shown in FIG. 53. The valve 70 is provided with two holes 70$a$ and 70$b$ which can be pushed to open against elasticity of the valve 70 and into which the front end of the device b3 is inserted.

Figure 50:
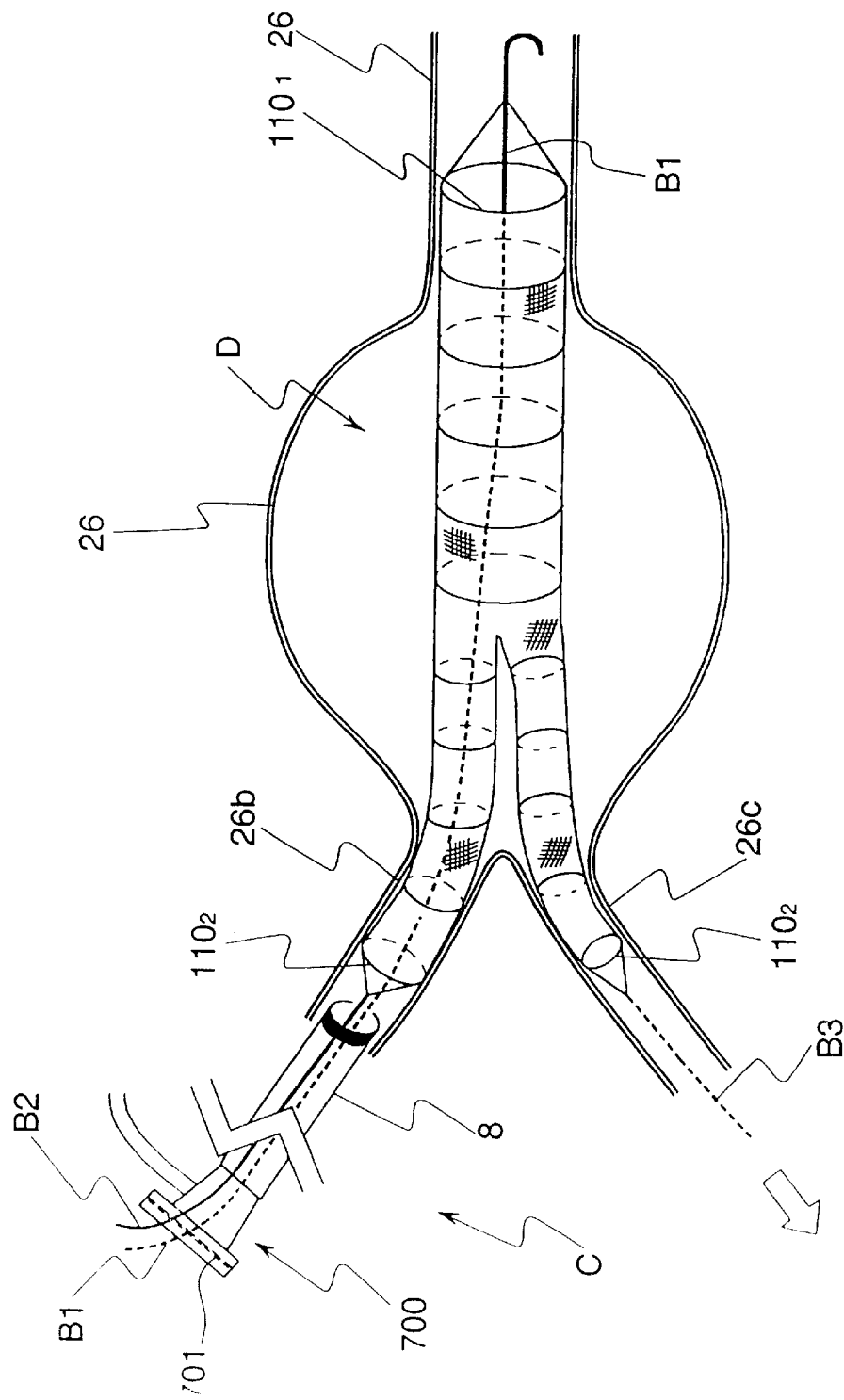
FIG. 50 is a view showing a condition just before the method of using has been finished.

Next, the process of implanting the artificial blood vessel D will be described below. Like the process shown in FIG. 25, first, the first device B1, the second device B2 and the guide pipe H are inserted into the cartridge 6 together with the collapsed artificial blood vessel D by pushing to open the hole of the valve 68. The third device B3 is inserted into the guide pipe H through the hole 70$a$ of the valve 70 provided at the base end h1 of the guide pipe H. Next, the sheath 700 is inserted into the cartridge 6 by pushing to open the valve 68 provided at the rear end of the cartridge 6. Since the devices B1, B2 and B3 are inserted into and passed through the holes 711 and 712 of the sheath 700 beforehand as mentioned above, (the third device B3 is inserted into the guide pipe H) when the front end of the sheath 700 is inserted into the cartridge 6 through the valve 68, inside the cartridge 6 is connected through inside the sheath 700 and the inner space is liquid-tightly sealed from outside of the valve 701. After the artificial blood vessel D is transported to a predetermined position beyond groin of the bifurcated affected portion by manipulating the first device B1, the artificial blood vessel D is released from the catheter 8 as shown in FIG. 49. Accompanying to the artificial blood vessel D, the second and third devices B2 and B3 are dragged and introduced into the body. The third device B3 is introduced into the body accompanying to the guide pipe H. The artificial blood vessel D is released after the main portion of the artificial blood vessel D is arranged at the predetermined position. The bifurcated portion of the artificial blood vessel D is kept in a collapsed condition by the retaining rod 1141 and 1142 shown in FIG. 38 after released. In this step, another bifurcated rear end wire zing 1102 is pushed to the bifurcated portion as shown by the arrow Z in FIG. 49 by means of the third device B3. Next, in this embodiment the base end b3a of the third device B3 is turned down and inserted into the guide pipe H. More specifically, the base end b3a of the third device B3 is pushed to open the hole 70b of the valve 70 shown in FIG. 53 so as to be inserted into the guide pipe H. After this, the guide member b3x is gripped so as to push and transport the third device B3 until the base end b3a is introduced into the body through the front end h2 of the guide pipe H. Under the condition, a catcher G for catching the device for transporting the artificial blood vessel is introduced into near the affected portion through the catheter K from another bifurcated portion of the groin. The catcher G is made of a tube g1 into which two wire members g2 and g3 are inserted and passed though with both of the front ends of the wire members g2 and g3 connected to form a loop. Concretely the catcher G is so arranged that a single wire member is inserted into and passed though the tube g1 and then the front end of the single wire member is turned down and again inserted into the tube g1 through the same end of the tube g1 from which the single wire member is out. Then when the wire members g2 and g3 are pushed against the tube g1, the loop projecting out of the tube g1 becomes bigger and when the wire members g2 and g3 are pulled from the tube g1, the loop projecting out of the tube g1 becomes smaller. Next, the base end b3a is caught by the catcher L1 by manipulating the guide member b3x of the third device B3 and the catcher G. As mentioned above, the third device B3 is curved around the base end b3a so as to make it easy for the catcher G to catch the device B3. As a result of this, it becomes easy to rotate, insert or pull the third device B3 by handling the guide member b3x which is out of the guide pipe H. After being caught by the catcher G, the base end b3a is pulled out of the body through another groin of the thigh. As the base end b3a is pulled further, the length of the third device B3 being out of the valve 70 of the guide pipe H becomes shorter and shorter and finally the third device B3 strains itself between the hole 70a and the hole 70b of the valve 70. Then the valve 70 between the hole 70a and the hole 70b is artificially broken so that the third device B3 is filly contained in the guide pipe H. The valve 70 may be broken by a surgical knife, or a stick shaped material. If the stick shaped material is left in the guide pipe H after the valve 70 is broken, it can effectively prevent bleeding from the broken part of the valve 70. Next the base end b3a of the third device B3 is further pulled out of the body through another groin of the thigh until only the front end of the third device B3 is left in the body as shown in FIG. 50. After the third device B3 is pulled out of the body, the rear end wire ring 1102 of the Y-shaped artificial blood vessel D is introduced into an a appropriate position of another branch from the trunk of the blood vessel by being pulled toward the direction shown by the arrow of FIG. 50. After the artificial blood vessel D is arranged in the appropriate position, the wires of the retaining rods 1141 and 1142 (shown in FIG. 42) each of which is attached to the second and the third devices B2 and B3 respectively are pulled so as to release the artificial blood vessel D from a collapsed condition. Then the bifurcated portions of the artificial blood vessel D are restored to the original shape and implanted into the bifurcated internal wall of the blood vessel in the affected portion. Finally, each wire 3 of the devices B1, B2 and B3 (see FIG. 15) is drawn so as to be released from the front end wire ring 1101 and the rear end wire ring 1102. Then the devices B1, B2 and B3 can be taken out of the body.

In accordance with the above-mentioned method, the third device B3 can be caught by the catcher G with accuracy without entangling in the artificial blood vessel D. More specifically, since the third device B3 is inserted into the catheter 8 through the guide pipe H in this embodiment, the third device B3 can be isolated from the artificial blood vessel D or the like while being transported in the catheter 8, thereby to avoid without fail inconvenience of the third device B3 entangling in the artificial blood vessel D or the devices B1 and B2 which may overwise occur when the third device B3 is directly inserted into the catheter 8 without using the guide pipe H. This also avoids inconvenience of dragging the artificial blood vessel D or the devices B1 and B2. As a result of this, the third device B3 can be introduced into another branch without fail. Since the guide pipe H is arranged with its front tip h2 closer to the bifurcated position of the affected portion than the front end of the catheter 8, it becomes easier to catch the base end b3a by the catcher G. As a result of this, the rate of successful implanting can drastically be improved. This effect can also be obtained by using the J-shaped guide pipe F shown in FIG. 41. However, in this embodiment since not only the front end of the device B3 but also the base end b3a thereof is turned down, the base end b3a can be caught by the catcher G when the base end b3a projects out of the front end h2 of the guide pipe H. Consequently, the position of the base end b3a can freely be adjusted by manipulating the guide member b3x. As a result of this, the device B3 can be caught with higher accuracy by the catcher G. In addition, since the front end of the catcher G is loop-shaped and smooth, there is no danger of damaging tissues of the body. Further, since the third device B3 is transported in the catheter K in a condition of being folded into a V-shape when it is to be taken after caught, the base end b3a of the third device B3 can be taken out of the body without fail.

Figure 59:
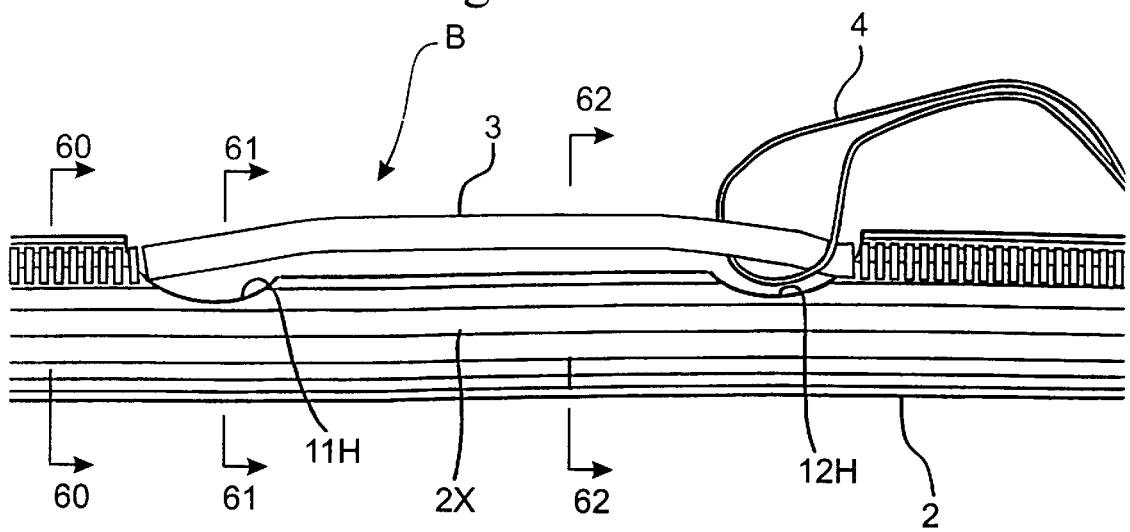
FIG. 59 is a view showing a modification of the device for transporting the artificial blood vessel.
Figure 64:
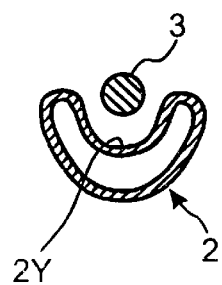
FIG. 64 is a cross-sectional view showing a modification corresponding to FIG. 62.
Figure 65:
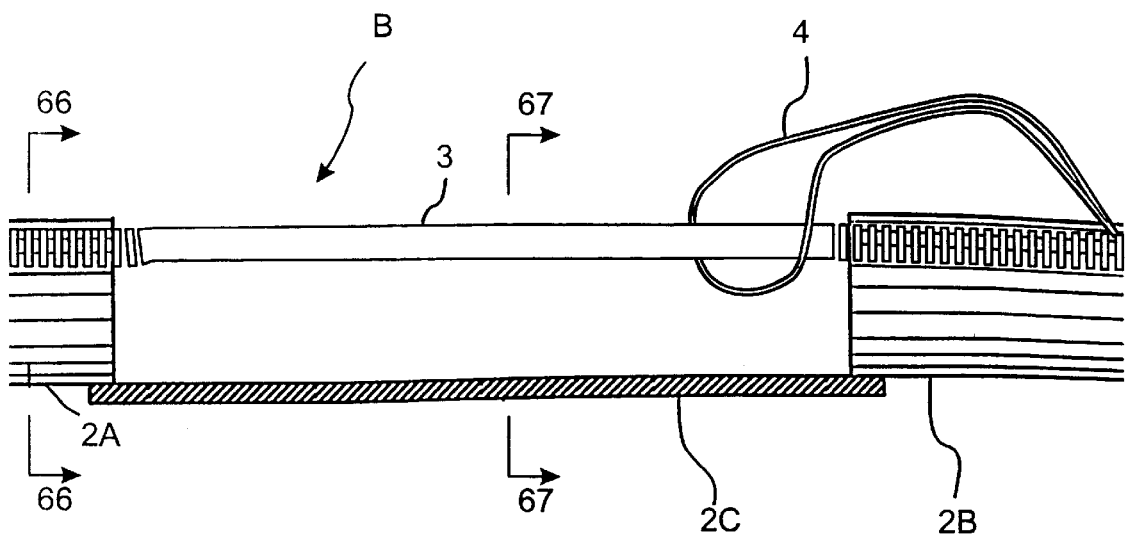
FIG. 65 is a view showing a modification different from the above of the device for transporting the artificial blood vessel.
Figure 66:
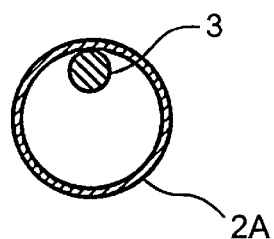
FIG. 66 is a cross-sectional view along the line X3—X3 of FIG. 65.
Figure 67:
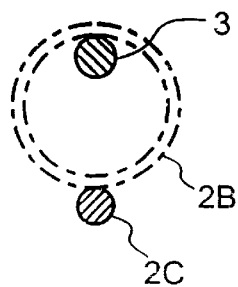
FIG. 67 is a cross-sectional view taken along the line Z3—Z3 of FIG. 65.
Figure 68:
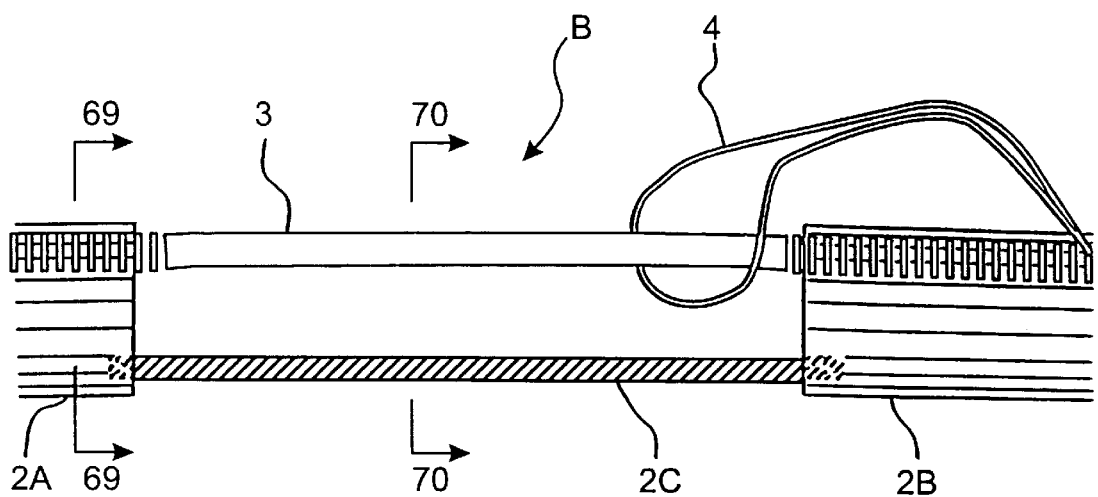
FIG. 68 is a view showing a modification different from the above of the device for transporting the artificial blood vessel.
Figure 69:
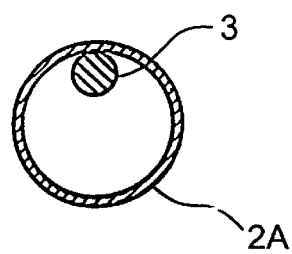
FIG. 69 is a cross-sectional view taken along the line Z4—Z4 of FIG. 68.
Figure 70:
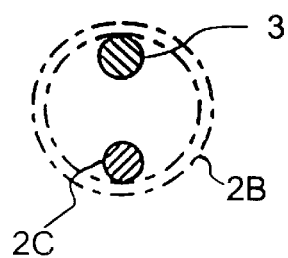
FIG. 70 is a cross-sectional view taken along the line Z3—Z3 of FIG. 68.

The device B (B1, B2 and B3) for transporting the artificial blood vessel can be modified in each of the above-mentioned embodiments. The side window formed in the tube 2, shown in FIGS. 54 through 58, comprises the first and the second opening holes 11H and 12H each spaced apart. The wire 3 pulled out of the tube 2 though the first opening hole 11H is hooked by the strings 4 and then introduced into the tube 2 through the second opening hole 12H. Thus arranged device B for transporting the artificial blood vessel does not require a big opening like the side window shown in FIG. 5. As a result of this, the tube 2 around the side window is thick enough to prevent bending, thereby effectively improving strength of the device B. In this case the cross-section of the device B may have a flat portion 2X between the opening holes 11H and 12H as shown in FIGS. 59 though 63. With the device B having the flat portion 2X, the wire 3 pulled out of the first opening hole 11H can be inserted into the second opening hole 12H with the wire 3 remaining relatively straight. Then the wire 3 can effectively be prevented from bending and it also avoids a case that the wire 3 fails to be pulled out of the tube 2. FIG. 64 shows another cross section having a concaved portion 2Y. As a further different modification shown in FIGS. 65 though 67, the tube 2 may comprise two tube elements 2A and 2B each spaced apart, and a connector 2C for connecting the outer circumferences of both tube elements 2A and 2B. No matter what arrangement the tube has, as far as the tube is strong enough as a whole, the device for transporting the artificial blood vessel can transport artificial blood vessels appropriately. The tube comprising two tube elements is especially effective for a tube having an extremely small diameter. If the tube of an extremely small diameter is provided with a side window, the window occupies most of the tube, which may weaken the strength of the tube. Consequently, the tube comprising two tube elements 2A and 2B can keep an appropriate strength as far as the material used for 2C is strong enough. The connector 2C may connect the internal circumferences of two tube elements 2A and 2B as shown in FIGS. 68 through 70. The cross-section of the tube element 2A, 2B is not limited to a circle as shown in FIG. 69, but may be flat or flat with partial circle. In addition, the device B for transporting the artificial blood vessel shown in FIGS. 54 through 70 may not have a string 4. In this case, the device B can pull the artificial blood vessel A effectively if the wire 3 is directly inserted into hooking means or a hole directly formed on the cover.

Figure 71:
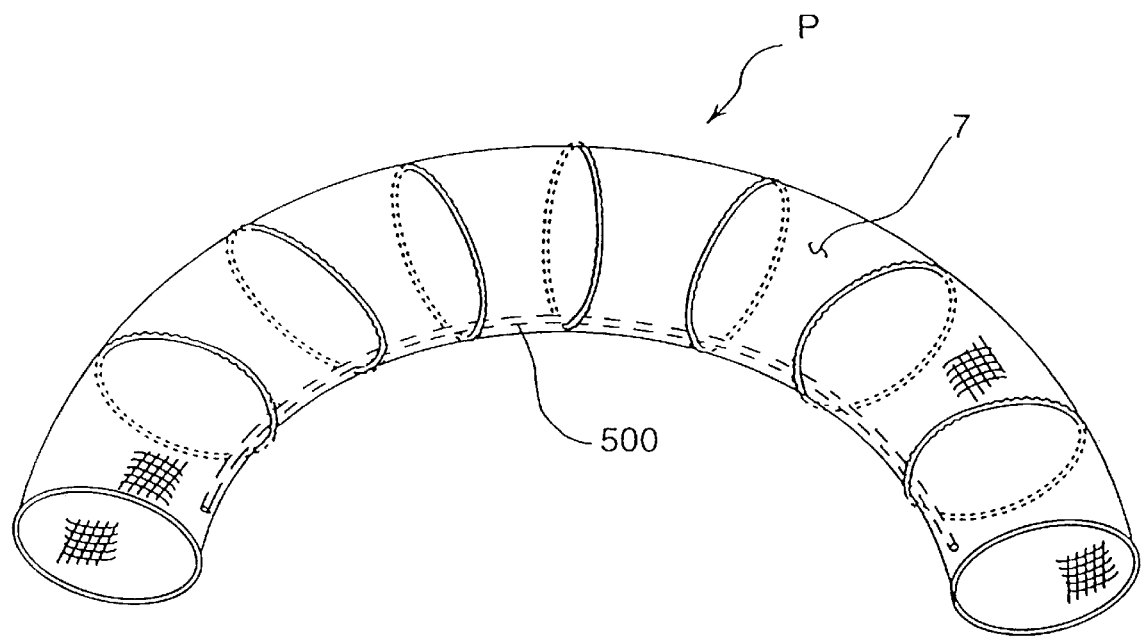
FIG. 71 is a view showing a modification of an artificial blood vessel.

On the other hand, as a modification of the artificial blood vessel, it is effective to use the artificial blood vessel shown in FIG. 71. The artificial blood vessel P has basically the same arrangement as that of the artificial blood vessel A shown in FIG. 1 except that an elastic thread 500 (for example, thread of urethane or the like) which can expand or contract so as to shrink a length of the artificial blood vessel 2 is embedded inside the tubular cover 7 along a specified generatrix. Thus arranged artificial blood vessel P can be transported in the catheter 8 in compact when folded into a small size like the above mentioned embodiment. In addition, since the artificial blood vessel P is restored into a curved shape as shown in FIG. 71 when released from the catheter 8 because the elastic thread 500 restrains a part of the artificial blood vessel P from restoring into a cylindrical shape, the artificial blood vessel P sticks to the blood vessel tightly when implanted into a curved affected portion such as a bowed portion of aorta, thereby to prevent leakage. This effect can greatly be improved if the artificial blood vessel P is used with an artificial blood vessel having a bellow portion.

It is also effective if a part or whole of the catheter 8 is made of bellow, although not shown in figures. A catheter 8 of a simple cylindrical shape is not only easy to break but also difficult to restore if once broken, which may lead to stricture in a body. While the catheter 8 made of bellow fits to a bent portion of the body easily with forming a natural curve, thereby to effectively avoid stricture in a body. Thus bellow-shaped catheter is suitable for transporting various kinds of appliances in addition to artificial blood vessels.

The device B for transporting the artificial blood vessel used in the above embodiments can be applied to pull various lands of appliances in addition to artificial blood vessels so as to introduce them into a body. The guide pipe H having valve 70 is also suitable for arranging an artificial blood vessel into a bifurcated portion having two or more branches. For example, when an artificial blood vessel having branches bifurcated from a trunk is used for the aorta of a neck, the trunk is arranged on the bowed portion of the aorta and the branch is introduced into the carotid artery or the upper arm artery. In this case the artificial blood vessel can be implanted with ease and accuracy by using the guide pipe H. Further the valve 68 shown in FIGS. 51 and 52 can be applied when a plurality of devices for transporting the artificial blood vessel are parallely introduced into a body without causing bleeding.

Further embodiments of the invention are now described with reference to FIGS. 72–74.

Figure 72:
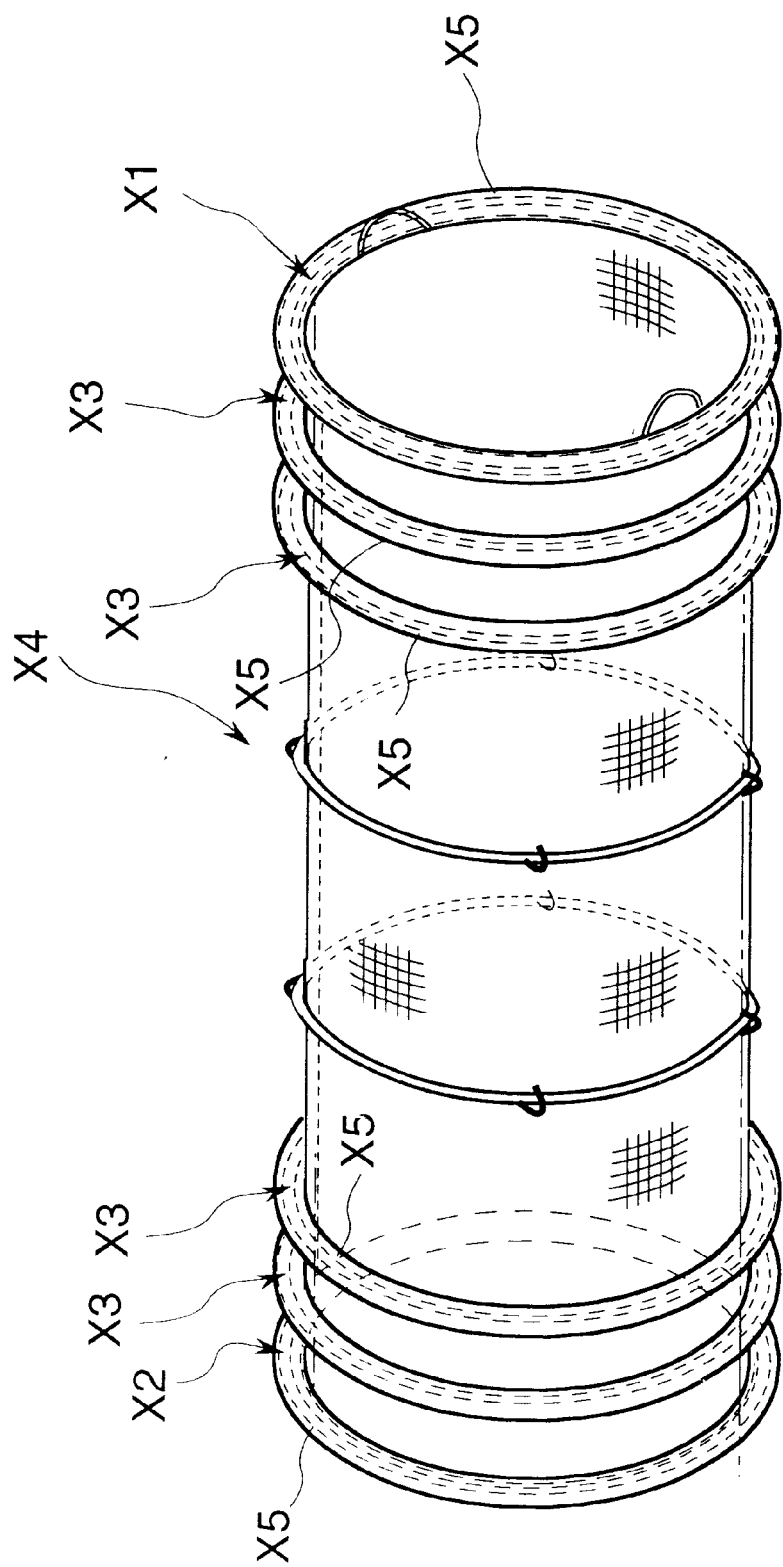
FIG. 72 is a perspective view showing a further modification of an artificial blood vessel.
Figure 73:
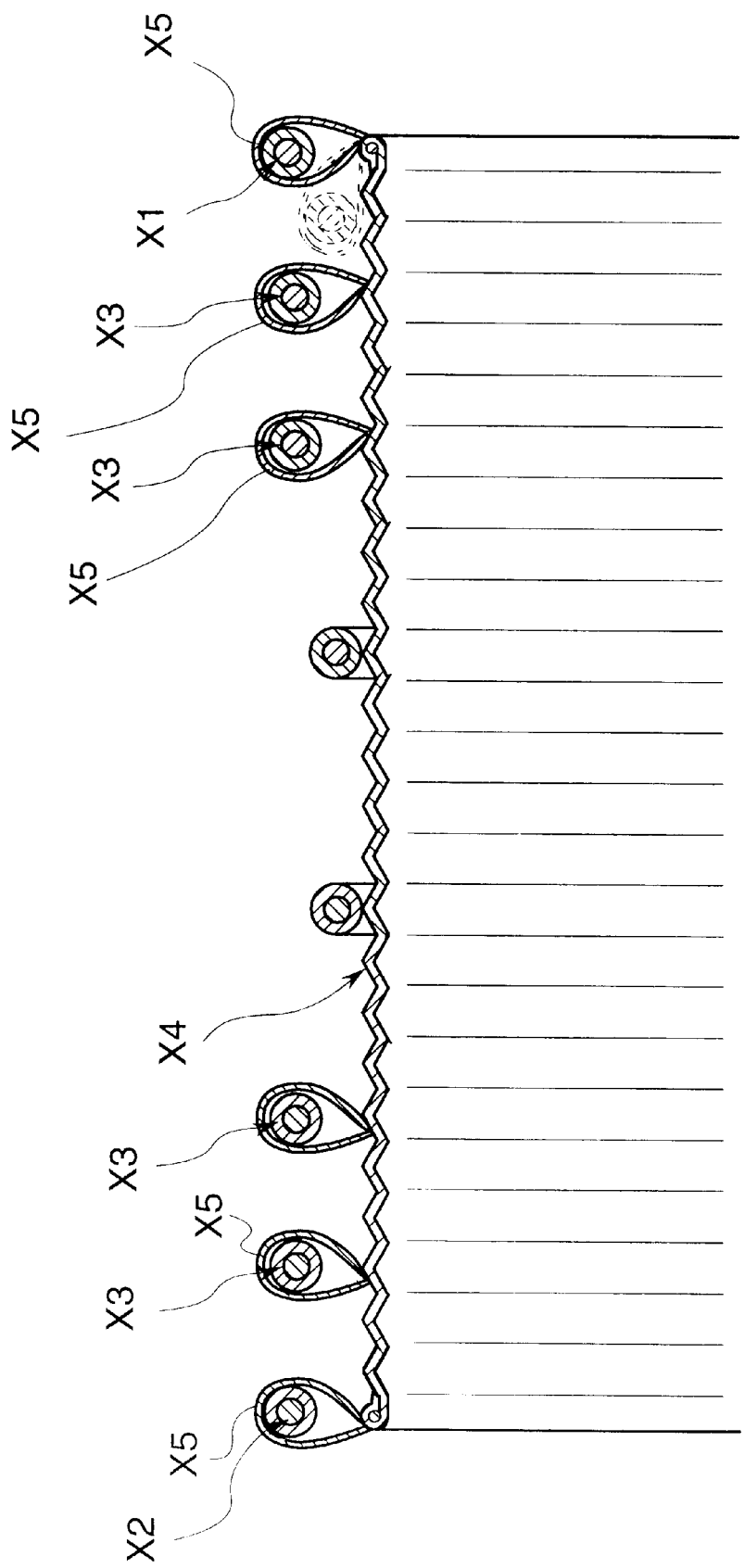
FIG. 73 is a vertical cross-sectional view of part of the artificial blood vessel shown in FIG. 72.

The method of the present claimed invention can preferably be applied to an artificial blood vessel, as shown in FIGS. 72 and 73, having an arrangement in which each of the front and rear end wire rings X1 and X2 and at least the intermediate wire rings X3 arranged adjacent to the front and rear end wire rings X1 and X2 are connected with the cover X4 through a film member X5 so that the wire rings X1, X2 and X3 can make a back and forth movement relative to the cover X4 within a certain range and a ring shaped gap formed between the wire rings and the cover is liquid-tightly sealed.

The film member X5 is a bag-shaped member in which whole of each wire rings X1, X2 and X3 is wrapped up and one end of the film member X5 is attached to the cover X4 almost to surround the outer circumference hereof so as to allow each of the wire rings X1, X2 and X3 to make a back and forth movement by making use of transformation of the film member X5.

Figure 74:
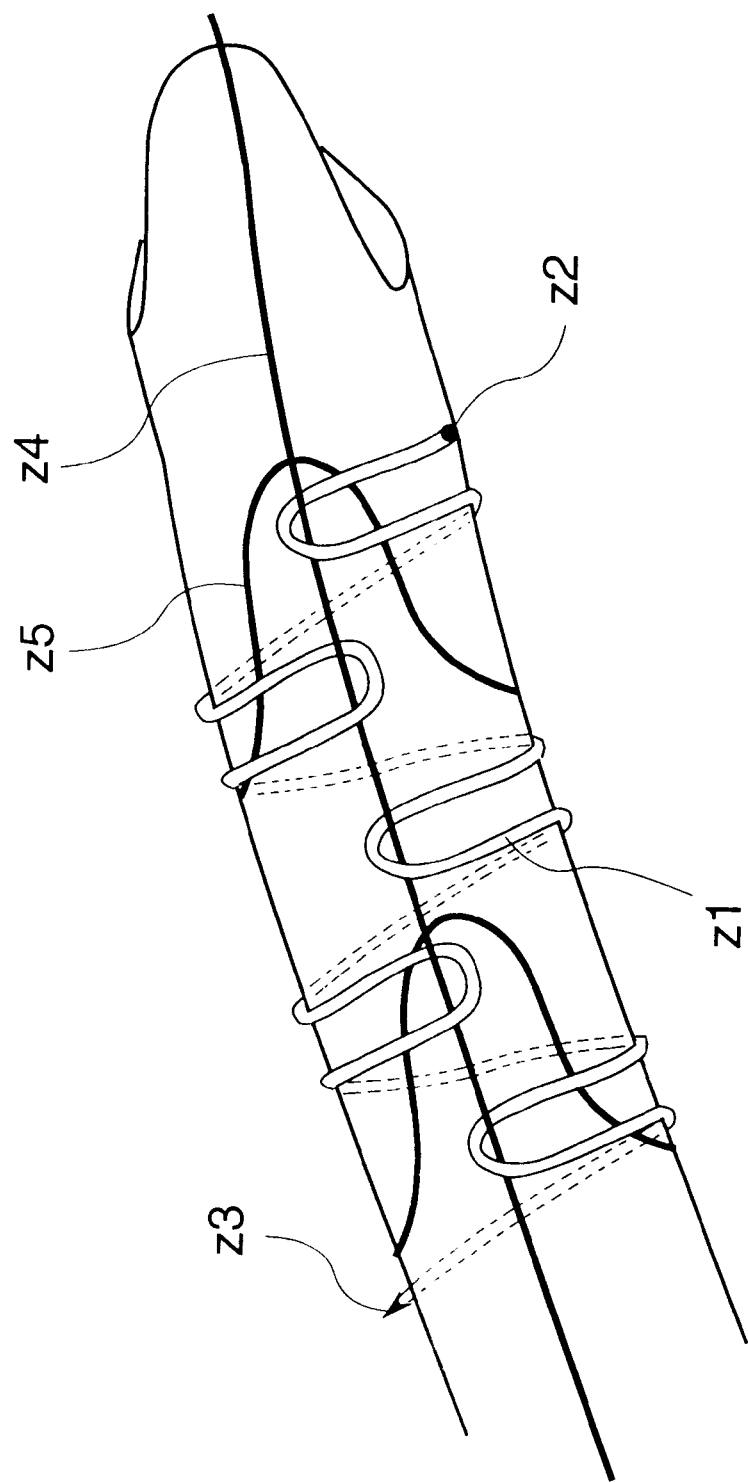
FIG. 74 is a perspective view showing a single string blood vessel tying arrangement representing a modification of the technique illustrated in FIG. 37.

Instead of a string which is provided for each of the wire rings as shown in FIG. 37, a single string element Z1 may be used, as shown in FIG. 74. One end Z2 of the string element Z1 is fixed to a part of the artificial blood vessel and the other end Z3 of the string element Z1 is wound around the retaining rod Z4 and turned clockwise and counterclockwise alternatively so as to keep each of the wire rings Z5 in a collapsed condition. The other end of the string element Z1 is fixed to another portion of the artificial blood vessel.

POSSIBLE APPLICATIONS IN INDUSTRY

As mentioned above, the appliance to be implanted in accordance with the invention is valuable as an artificial blood vessel. It also can be collapsed into a small size to take a regular wavy shape having the same phase as a whole by means of the method of collapsing the appliance to be implanted in accordance with the invention especially because of smooth movement of the intermediate wire rings. The method of using the appliance to be implanted in accordance with the invention makes it possible to implant a Y-shaped appliance to be implanted into a bifurcated portion of a human organ easily with non-operational method.

What is claimed is:

1. A method of collapsing an appliance to be implanted comprising a front end wire ring, a rear end wire ring arranged facing to the front end wire ring, a tubular cover which connects the front and rear end wire rings, and an intermediate wire ring arranged between the front and rear end wire rings, in which each of the wire rings is given flexibly foldable elasticity, said method comprising:

folding each of the wire rings into a wavy folded shape forming forwardly directed peaks and bottoms of forwardly directed valleys alternatively and repeatedly;

tying each of the wire rings by a string with a portion formed into a loop; and inserting and passing a retaining rod through said loops so as to keep each of the wire rings in a collapsed condition.

2. The method of collapsing the appliance to be implanted, described in claim 1, wherein said retaining rod comprises a tube and a wire which is inserted into and passed through the tube and that after each of the wire rings is placed in a collapsed condition the tube is pulled out so as to keep the collapsed condition by the wire alone.

3. The method of collapsing the appliance to be implanted, described in claim 2, wherein the appliance to be implanted has an arrangement in which each of the front and rear end wire rings and at least intermediate wire rings arranged adjacent to the front and rear end wire rings are connected with the cover through a film member so that said front end, rear end and intermediate wire rings can make a back and forth movement relative to the cover within a certain range and wherein a ring shaped gap formed between said front end, rear end and intermediate wire rings and the cover is liquid-tightly sealed.

4. The method of collapsing the appliance to be implanted, described in claim 1, wherein:
a pair of strings, each of which has a loop at a tip thereof, are provided for each of the wire rings respectively,
the strings are engaged with either one of a respective wire ring or the tubular cover, and one string of each pair of strings is wound around its respective wire ring clockwise until it reaches backward of the respective wire ring while the other string is wound around the respective wire ring counterclockwise until it reaches backward of the respective wire ring, h retaining rod is passed through a part at which each of the loops overlaps, and
each of the strings is tied to the other of the pair so as to keep each of the wire rings in a collapsed condition.

5. The method of collapsing the appliance to be implanted, described in claim 4, wherein the appliance to be implanted has an arrangement in which each of the front and rear end wire rings and at least intermediate wire rings arranged adjacent to the front and rear end wire rings are connected with the cover through a film member so that said front end, rear end and intermediate wire rings can make a back and forth movement relative to the cover within a certain range and wherein a ring shaped gap formed between said front end, rear end and intermediate wire rings and the cover is liquid-tightly sealed.

6. The method of collapsing the appliance to be implanted, described in claim 1 each of said strings is a continuous part of a single string element and one end of said string element is fixed to the appliance and the other end thereof is wound around the retaining rod and turned clockwise and counterclockwise alternatively so as to keep each of the wire rings in a collapsed condition and said other end of the string element is fixed to another portion of the appliance to be implanted.

7. The method of collapsing the appliance to be implanted, described in claim 6, wherein the appliance to be implanted has an arrangement in which each of the front and rear end wire rings and at least intermediate wire rings arranged adjacent to the front and rear end wire rings are connected with the cover through a film member so that said front end, rear end and intermediate wire rings can make a back and forth movement relative to the cover within a certain range and wherein a ring shaped gap formed between said front, rear and intermediate wire rings and the cover is liquid-tightly sealed.

8. The method of collapsing the appliance to be implanted, described in claim 1, wherein the appliance to be implanted has an arrangement in which each of the front and rear end wire rings and at least intermediate wire rings arranged adjacent to the front and rear end wire rings are connected with the cover through a film member so that said front end, rear end and intermediate wire rings can make a back and forth movement relative to the cover within a certain range and wherein a ring shaped gap formed between said front, rear and intermediate wire rings and the cover is liquid-tightly sealed.

9. The method of collapsing the appliance to be implanted, described in claim 8, wherein said film member is a bag-shaped member in which a whole of each wire ring is wrapped up and one end of said film member is attached to the cover almost to surround the outer circumference thereof so as to allow each of the wire rings to make a back and forth movement by making use of a transformation of the film member.

10. An appliance to be implanted comprising a front end wire ring, a rear end wire ring arranged facing to the front end wire ring, a tubular cover which connects the front and rear end wire rings, and an intermediate wire ring arranged between the front and rear end wire rings, in which each of the wire rings is given flexibly foldable elasticity, wherein:
each of the wire rings is folded into a wavy folded shape forming forwardly directed peaks and bottoms of forwardly directed valleys alternatively and repeatedly;
each of the wire rings is tied by a string with a portion formed into a loop; and
a retaining rod is inserted and passed through said loops so as to keep each of the wire rings in a collapsed condition.

11. An appliance according to claim 10 said retaining rod comprises a tube and a wire which is inserted into and passed through the tube and that after each of the wire rings is placed in a collapsed condition the tube can be pulled out so as to keep the collapsed condition by the wire alone.

12. An appliance according to claim 11, wherein the appliance to be implanted has an arrangement in which each of the front and rear end wire rings and at least intermediate wire rings arranged adjacent to the front and rear end wire rings are connected with the cover through a film member so that said front end, rear end and intermediate wire rings can make a back and forth movement relative to the cover within a certain range and wherein a ring shaped gap formed between said front ends rear end and intermediate wire rings and the cover is liquid-tightly sealed.

13. An appliance according to claim 10, wherein
a pair of strings each of which has a loop at a tip thereof are provided for each of the wire rings respectively,
the strings are engaged with either one of a respective wire ring or the tubular cover, and one string of each pair of strings is wound around its respective wire ring clockwise until it reaches backward of the respective wire ring while the other string is wound around the respective wire ring counterclockwise until it reaches backward of the respective wire ring,
the retaining rod is passed through a part at which each of the loops overlaps, and
each of the strings is tied to the other of the pair so as to keep each of the wire rings in a collapsed condition.

14. An appliance according to claim 13, wherein the appliance to be implanted has an arrangement in which each of the front and rear end wire rings and at least intermediate wire rings arranged adjacent to the front and rear end wire rings are connected with the cover through a film member so that said front end, rear end and intermediate wire rings can make a back and forth movement relative to the cover within a certain range and wherein a ring shaped gap formed between said front end, rear end and intermediate wire rings and the cover is liquid-tightly sealed.

15. An appliance according to claim 10 each of said strings is a continuous part of a single string element and one end of said string element is fixed to the appliance and the other end thereof is wound around the retaining rod and turned clockwise and counterclockwise alternatively so as to keep each of the wire rings in a collapsed condition and said other end of the string element is fixed to another portion of the appliance to be implanted.

16. An appliance according to claim 15, wherein the appliance to be implanted has an arrangement in which each of the front and rear end wire rings and at least interdediate wire rings adjacent to the front and rear end wire rings are connected with the cover through a film member so that said front end, rear end and intermediate wire rings can make a back and forth movement relative to the cover within a certain range and wherein a ring shaped gap formed between said front end, rear end and intermediate wire rings and the cover is liquid-tightly sealed.

17. An appliance according to claim 10, wherein the appliance to be implanted has an arrangement in which each of the front and rear end wire rings and at least intermediate wire rings arranged adjacent to the front and rear end wire rings are connected with the cover through a film member so that said front end, rear end and intermediate wire rings can make a back and forth movement relative to the cover within a certain range and wherein a ring shaped gap formed between said front end, rear end and intermediate wire rings and the cover is liquid-tightly sealed.

18. An appliance according to claim 10, wherein said film member is a bag-shaped member in which a whole of each wire ring is wrapped up and one end of said film member is attached to the cover almost to surround the outer circumference thereof so as to allow each of the wire rings to make a back and forth movement by making use of a transformation of the film member.

* * * * *

UNITED STATES PATENT AND TRADEMARK OFFICE
CERTIFICATE OF CORRECTION

PATENT NO.    : 6,270,520 B1
DATED         : August 7, 2001
INVENTOR(S)   : Kanji Inoue It is certified that error appears in the above-identified patent and that said Letters Patent is hereby corrected as shown below:

<u>Title page,</u>
Item [30], "Foreign Application Priority Data," change "May 19, 1995 (JP)"
to -- May 19, 1995 (WO) --.

<u>Column 29,</u>
Line 28, "h" has been replaced with -- the --.
Line 45, -- wherein -- has been inserted after "Claim 1".

<u>Column 30,</u>
Line 30, after "An appliance according to claim 10", -- wherein -- has been inserted.
Line 43, "front ends" has been replaced with -- front end --.

<u>Column 31,</u>
Line 3, after "An appliance according to claim 10", -- wherein -- has been inserted.
Line 13, "interdediate" has been replaced with -- intermediate --.
Line 14, -- arranged -- has been inserted between wire rings and adjacent.

Signed and Sealed this

Second Day of July, 2002

Attest:

Attesting Officer

JAMES E. ROGAN
*Director of the United States Patent and Trademark Office*